United States Patent
Debenham et al.

(10) Patent No.: US 7,728,141 B2
(45) Date of Patent: Jun. 1, 2010

(54) SUBSTITUTED NAPHTHYRIDINONE DERIVATIVES

(75) Inventors: John S. Debenham, Scotch Plains, NJ (US); George A. Doss, Westfield, NJ (US); Christina B. Madsen-Duggan, Scotch Plains, NJ (US); Thomas F. Walsh, Watchung, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1008 days.

(21) Appl. No.: 10/576,796

(22) PCT Filed: Oct. 29, 2004

(86) PCT No.: PCT/US2004/036102

§ 371 (c)(1),
(2), (4) Date: Apr. 21, 2006

(87) PCT Pub. No.: WO2005/047285

PCT Pub. Date: May 26, 2005

(65) Prior Publication Data

US 2007/0032517 A1    Feb. 8, 2007

Related U.S. Application Data

(60) Provisional application No. 60/517,060, filed on Nov. 4, 2003.

(51) Int. Cl.
C07D 471/04 (2006.01)
A61K 31/4375 (2006.01)

(52) U.S. Cl. .................................. 546/123; 514/300

(58) Field of Classification Search ............... 546/123; 514/300
See application file for complete search history.

(56) References Cited

U.S. PATENT DOCUMENTS

| | | |
|---|---|---|
| 6,344,474 B1 | 2/2002 | Maruani et al. |
| 2004/0214838 A1 | 10/2004 | Carpino et al. |
| 2004/0214855 A1 | 10/2004 | Carpino et al. |
| 2004/0214856 A1 | 10/2004 | Carpino et al. |
| 2004/0248881 A1 | 12/2004 | Carpino et al. |
| 2005/0085493 A1 | 4/2005 | Brain et al. |
| 2005/0143381 A1 | 6/2005 | Yu et al. |
| 2005/0203112 A1 | 9/2005 | Castonguay et al. |
| 2005/0272763 A1 | 12/2005 | Toupence et al. |
| 2006/0094714 A1 | 5/2006 | Bullock et al. |

FOREIGN PATENT DOCUMENTS

| | | |
|---|---|---|
| EP | 1 142 877 | 10/2001 |
| WO | WO 99/02499 | 1/1999 |
| WO | WO 03/086394 | 10/2003 |
| WO | WO 2004/060882 | 7/2004 |
| WO | WO 2004/087704 | 10/2004 |
| WO | WO 2005/103052 | 1/2005 |
| WO | WO 2005/021547 | 3/2005 |
| WO | WO 2005/035532 | 4/2005 |
| WO | WO 2005/049615 | 6/2005 |
| WO | WO 2005/061504 | 7/2005 |
| WO | WO 2005/061505 | 7/2005 |
| WO | WO 2005/061507 | 7/2005 |

OTHER PUBLICATIONS

Dorwald F. A. Side Reactions in Organic Synthesis, 2005, Wiley: VCH, Weinheim p. IX of Preface.*
Ferrarini et al., Bioorg. & Medicinal Chem., vol. 12 (2004), pp. 1921-1933, "Synthesis and biological evaluation of 1,8-naphthyridin-4(1H)-on-3-carboxamide derivatives as new ligands of cannabinoid receptors".
Lange et al., Current Opin. in Drug Discovery & Develop., vol. 7 (2004), pp. 498-506, "Recent advances in CB1 cannabinoid receptor antagonists".
Pertwee, Exp. Opin. Invest. Drugs, vol. 9 (2000), pp. 1553-1571, "Cannabinoid receptor ligands: clinical and neuropharmacological considerations, relevant to future drug discovery and development".
Pertwee, Addiction Biology, vol. 5 (2000), pp. 37-46, "Neuropharmacology and therapeutic potential of cannabinoids".
Evens et al., American Chem. Society, vol. 12 (1979), Poly(1,8-naphthyridines) and 1,9,10-anthyridines: Model systems for "Black Orlon".

* cited by examiner

*Primary Examiner*—Rita J Desai
(74) *Attorney, Agent, or Firm*—Baerbel R. Brown; Catherine D. Fitch

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver.

8 Claims, No Drawings

SUBSTITUTED NAPHTHYRIDINONE DERIVATIVES

CROSS-REFERENCE TO RELATED APPLICATIONS

This application is a U.S. National Phase application under 35 U.S.C. §371 of PCT Application No. PCT/US2004/036102, filed Oct. 29, 2004, which claims priority under 35 U.S.C. §119 from U.S. provisional application No. 60/517,060, filed Nov. 4, 2003.

BACKGROUND OF THE INVENTION

Marijuana (*Cannabis sativa* L.) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

There is at least one CB1 modulator characterized as an inverse agonist or an antagonist, N-(1-piperidinyl)-5-(4-chlorophenyl)-(2,4-dichlorophenyl)-4-methylpyrazole-3-carboxamide (SR1141716A, rimonabant, ACOMPLIA), in clinical trials for treatment of eating disorders at this time. There still remains a need for potent low molecular weight CB1 modulators that have pharmacokinetic and pharmacodynamic properties suitable for use as human pharmaceuticals.

Other cannabinoid receptor modulating compounds are disclosed in U.S. Pat. Nos. 4,973,587, 5,013,837, 5,081,122, 5,112,820, 5,292,736, 5,532,237, 6,355,631, 6,479,479 and PCT publications WO 97/29079, 98/37061, 99/02499, 00/10967, 00/10968, 01/58869, 01/64632, 01/64633, 01/64634, 01/70700, 02/076949, 03/026647, 03/026648, 03/027069, 03/027076, 03/027114, and 03/077847. WO 04/087880 is directed to antidiabetic naphthyridinone compounds.

The compounds of the present invention are modulators of the Cannabinoid-1 (CB1) receptor and are useful in the treatment, prevention and suppression of diseases mediated by the CB1 receptor. In particular, compounds of the present invention are antagonists or inverse agonists of the CB1 receptor. The invention is concerned with the use of these compounds to modulate the CB1 receptor.

SUMMARY OF THE INVENTION

The present invention is concerned with novel substituted naphthyridinone derivatives of general Formula I:

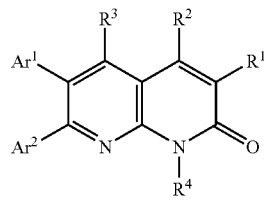

and pharmaceutically acceptable salts thereof which are antagonists and/or inverse agonists of the Cannabinoid-1 (CB1) receptor and are useful in the treatment, prevention or suppression of diseases mediated by the CB1 receptor. The invention is concerned with the use of these novel compounds to selectively antagonize the CB1 receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith, including left ventricular hypertrophy, as well as treating obesity in other mammalian species, including companion animals such dogs and cats. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds of the present invention are represented by structural formula I:

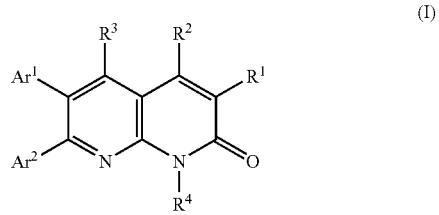

and pharmaceutically acceptable salts thereof.

In one embodiment of the present invention, $R^1$ is selected from: hydrogen, halogen, $C_{1-10}$alkyl, $C_{2-10}$ alkenyl, $C_{2-10}$alkynyl, —CN, —C(O)$R^7$, —O$R^d$, —N$R^5R^6$, —S(O)$_m$$R^7$, cycloalkyl, cycloheteroalkyl, aryl, and heteroaryl; wherein: alkyl, alkenyl, and alkynyl moieties are optionally substituted with one, two, or three substituents independently selected from $R^a$, and cycloalkyl, cycloheteroalkyl, aryl and heteroaryl moieties are optionally substituted with one, two, or three substituents independently selected from $R^b$;

or $R^1$, together with $R^2$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from $R^b$, wherein one or two of the carbon substituents may also be oxo, and wherein the ring is saturated or has one or two degrees of unsaturation.

In one class of this embodiment, $R^1$ is selected from: hydrogen, halogen, $C_{1-6}$alkyl, —CN, —C(O)$R^7$, —O$R^d$, —N$R^5R^6$, —S(O)$_2$$R^7$, cycloalkyl, cycloheteroalkyl, aryl, and heteroaryl; wherein: allyl moieties are unsubstituted or substituted with one, two, or three substituents independently selected from $R^a$, and cycloalkyl, cycloheteroalkyl, aryl and heteroaryl moieties are unsubstituted or substituted with one, two, or three substituents independently selected from $R^b$;

or $R^1$ together with $R^2$ forms a 4 to 7 membered ring, containing 1, or 2 heteroatoms independently selected from nitrogen and oxygen; unsubstituted or substituted on carbon or nitrogen with one, two or three substituents independently selected from $R^b$, wherein one or two of the carbon substituents may also be oxo, and wherein the ring is saturated or has one degree of unsaturation.

In one subclass of this class, $R^1$ is selected from: hydrogen, halogen, $C_{1-4}$alkyl, —CN, —C(O)$R^7$, —O$R^d$, —N$R^5R^6$, and cycloheteroalkyl; wherein: alkyl moieties are unsubstituted or substituted with one, two, or three substituents independently selected from $R^a$, and cycloheteroalkyl moieties are unsubstituted or substituted with one, two, or three substituents independently selected from $R^b$; or $R^1$ together with $R^2$ forms a 4 to 7 membered ring, containing 1 or 2 heteroatoms independently selected from nitrogen and oxygen; unsubstituted or substituted on carbon or nitrogen with one, two or three substituents independently selected from $R^b$, wherein one or two of the carbon substituents may also be oxo, and wherein the ring is saturated or has one degree of unsaturation.

In one subclass of this class, $R^1$ is selected from: hydrogen; halogen; $C_{1-3}$alkyl, unsubstituted or substituted with hydroxy or methoxy; —CN; methyloxycarbonyl-; methylcarbonyl-; isopropyloxy-carbonyl-; bromomethylcarbonyl-; —C(O)NH$_2$; methoxy; —N$R^5R^6$, wherein $R^5$ is methyl and $R^6$ is $C_{1-3}$alkyl, or $R^5$ and $R^6$, together with the nitrogen to which they are attached, form a 5-membered cycloheteroalkyl ring; and cycloheteroalkyl;

or $R^1$ together with $R^2$ forms a 4 to 7 membered ring, containing 1 or 2 heteroatoms independently selected from nitrogen and oxygen; substituted on carbon or nitrogen with one, two or three substituents independently selected from methyl, isopropyl, methylcarbonyl, benzyl, hydroxyl, and oxo, wherein one or two of the carbon substituents may also be oxo, and wherein the ring is has one degree of unsaturation.

In another subclass of this class, $R^1$ is selected from: hydrogen; halogen; $C_{1-3}$alkyl, unsubstituted or substituted with hydroxy or methoxy; —CN; methyloxycarbonyl-; methylcarbonyl-; isopropyloxycarbonyl-; bromomethylcarbonyl-; —C(O)NH$_2$; methoxy-; —N$R^5R^6$, wherein $R^5$ is methyl and $R^6$ is $C_{1-3}$alkyl, or $R^5$ and $R^6$, together with the nitrogen to which they are attached, form a 5-membered cycloheteroalkyl ring; and cycloheteroalkyl;

or $R^1$ together with $R^2$ forms a 4 to 7 membered substituted heteroalkyl ring, selected from:

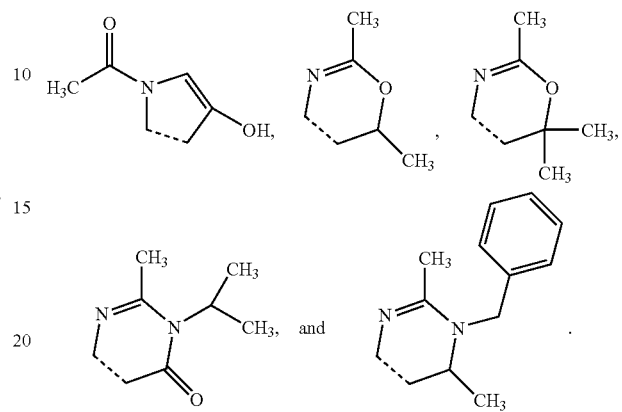

In one embodiment of the present invention, $R^1$ is selected from: halogen, $C_{1-10}$alkyl, $C_{2-10}$ alkenyl, $C_{2-10}$alkynyl, —CN, —C(O)$R^7$, —O$R^d$, —N$R^5R^6$, —S(O)$_m$$R^7$, cycloalkyl, cycloheteroalkyl, aryl, and heteroaryl; wherein: alkyl, alkenyl, and alkynyl moieties are optionally substituted with one, two, or three substituents independently selected from $R^a$, and cycloalkyl, cycloheteroalkyl, aryl and heteroaryl moieties are optionally substituted with one, two, or three substituents independently selected from $R^b$; or $R^1$, together with $R^2$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from $R^b$, wherein one or two of the carbon substituents may also be oxo, and wherein the ring is saturated or has one or two degrees of unsaturation.

In one class of this embodiment, $R^1$ is selected from: halogen, $C_{1-6}$alkyl, —CN, —C(O)$R^7$, —O$R^d$, —N$R^5R^6$, —S(O)$_2$$R^7$, cycloalkyl, cycloheteroalkyl, aryl, and heteroaryl; wherein: alkyl moieties are unsubstituted or substituted with one, two, or three substituents independently selected from $R^a$, and cycloalkyl, cycloheteroalkyl, aryl and heteroaryl moieties are unsubstituted or substituted with one, two, or three substituents independently selected from $R^b$;

or $R^1$ together with $R^2$ forms a 4 to 7 membered ring, containing 1, or 2 heteroatoms independently selected from nitrogen and oxygen; unsubstituted or substituted on carbon or nitrogen with one, two or three substituents independently selected from $R^b$, wherein one or two of the carbon substituents may also be oxo, and wherein the ring is saturated or has one degree of unsaturation.

In one subclass of this class, $R^1$ is selected from: halogen, $C_{1-4}$alkyl, —CN, —C(O)$R^7$, —O$R^d$, —N$R^5R^6$, and cycloheteroalkyl; wherein: alkyl moieties are unsubstituted or substituted with one, two, or three substituents independently selected from $R^a$, and cycloheteroalkyl moieties are unsubstituted or substituted with one, two, or three substituents independently selected from $R^b$;

or $R^1$ together with $R^2$ forms a 4 to 7 membered ring, containing 1 or 2 heteroatoms independently selected from nitrogen and oxygen; unsubstituted or substituted on carbon or nitrogen with one, two or three substituents independently selected from $R^b$, wherein one or two of the carbon substituents may also be oxo, and wherein the ring is saturated or has one degree of unsaturation.

In one subclass of this class, $R^1$ is selected from: halogen; $C_{1-3}$alkyl, unsubstituted or substituted with hydroxy or methoxy; —CN; methyloxycarbonyl-; methylcarbonyl-; isopropyloxy-carbonyl-; bromomethylcarbonyl-; —C(O)NH$_2$; methoxy; —NR$^5$R$^6$, wherein R$^5$ is methyl and R$^6$ is $C_{1-3}$alkyl, or R$^5$ and R$^6$, together with the nitrogen to which they are attached, form a 5-membered cycloheteroalkyl ring; and cycloheteroalkyl;

or R$^1$ together with R$^2$ forms a 4 to 7 membered ring, containing 1 or 2 heteroatoms independently selected from nitrogen and oxygen; substituted on carbon or nitrogen with one, two or three substituents independently selected from methyl, isopropyl, methylcarbonyl, benzyl, hydroxyl, and oxo, wherein one or two of the carbon substituents may also be oxo, and wherein the ring is has one degree of unsaturation.

In another subclass of this class, $R^1$ is selected from: halogen; $C_{1-3}$alkyl, unsubstituted or substituted with hydroxy or methoxy; —CN; methyloxycarbonyl-; methylcarbonyl-; isopropyloxycarbonyl-; bromomethylcarbonyl-; —C(O)NH$_2$; methoxy-; —NR$^5$R$^6$, wherein R$^5$ is methyl and R$^6$ is $C_{1-3}$alkyl, or R$^5$ and R$^6$, together with the nitrogen to which they are attached, form a 5-membered cycloheteroalkyl ring; and cycloheteroalkyl;

or R$^1$ together with R$^2$ forms a 4 to 7 membered substituted heteroalkyl ring, selected from:

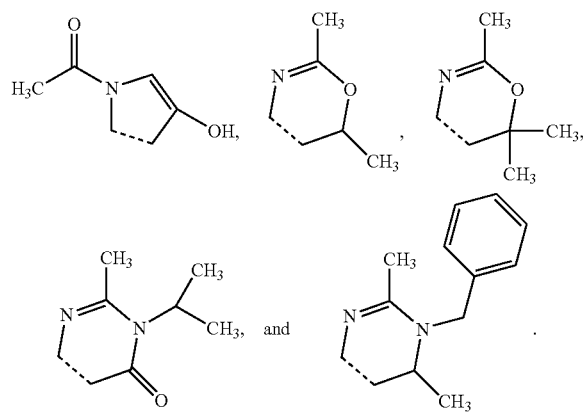

In still another subclass of this class, $R^1$ is selected from: —C(O)CH$_3$, —CH(OH)CH$_3$, —CH$_3$, —CH$_2$CH$_3$, —CH(CH$_3$)$_2$, —CH(OCH$_3$)(CH$_3$), —C(O)—OCH$_3$, —C(O)OCH(CH$_3$)$_2$, —CN, —C(O)NH$_2$, —C(O)N(CH$_3$)$_2$, —Cl, —N(CH$_3$)$_2$, —N(CH$_3$)(CH(CH$_3$)$_2$), and pyrrolidinyl.

In yet another subclass, $R^1$ is selected from: —C(O)CH$_3$, —CH$_3$, —OCH$_3$, and —Cl.

In one embodiment of the present invention, $R^2$ is selected from: hydrogen, —NR$^5$R$^6$, —COR$^7$, $C_{1-6}$alkyl, $C_{2-6}$ alkenyl, $C_{2-6}$alkynyl, aryl, arylC$_{1-6}$alkyl-, arylC$_{2-6}$alkenyl-, heteroaryl, heteroarylC$_{1-6}$alkyl-, heteroarylC$_{2-6}$alkenyl-, cycloalkyl, cycloheteroalkyl, and —OR$^d$; wherein alkyl, alkenyl, and alkynyl moieties are unsubstituted or substituted with one, two, or three substituents independently selected from R$^a$; and aryl and heteroaryl moieties are unsubstituted or substituted with one, two, or three substituents independently selected from R$^b$; and the cycloalkyl and cycloheteroalkyl moieties are unsubstituted or substituted with one, two, three or four substituents independently selected from R$^b$ and oxo;

or R$^2$, together with R$^1$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from R$^b$, wherein one or two of the carbon substituents may also be oxo, and wherein the ring is saturated or has one or two degrees of unsaturation.

In one class of this embodiment, $R^2$ is selected from: hydrogen, —NR$^5$R$^6$, —COR$^7$, $C_{1-6}$alkyl, phenyl, pyridyl, cycloheteroalkyl, —OR$^d$; wherein alkyl moieties are unsubstituted or substituted with one, two, or three substituents independently selected from R$^a$; and phenyl and pyridyl moieties are unsubstituted or substituted with one, two, or three substituents independently selected from R$^b$; and the cycloheteroalkyl moiety is unsubstituted or substituted with one, two, three or four substituents independently selected from R$^b$ and oxo;

or R$^2$, together with R$^1$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from R$^b$, wherein one or two of the carbon substituents may also be oxo, and wherein the ring is saturated or has one degree of unsaturation.

In one subclass of this class, $R^2$ is selected from: —NR$^5$R$^6$, and $C_{1-6}$alkyl; wherein alkyl moieties are unsubstituted or substituted with one, two, or three substituents independently selected from R$^a$;

or R$^2$, together with R$^1$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from R$^b$, wherein one or two of the carbon substituents may be oxo, and wherein the ring is saturated or has one degree of unsaturation.

In another subclass of this class, $R^2$ is —NR$^5$R$^6$, or $C_{1-6}$alkyl, or R$^2$, together with R$^1$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from R$^b$, wherein one or two of the carbon substituents may be oxo, and wherein the ring is saturated or has one degree of unsaturation.

In still another subclass of this class, $R^2$ is —NR$^5$R$^6$, or $C_{1-6}$alkyl; wherein R$^5$ is selected from: hydrogen, methyl, and methlcarbonyl-, and R$^6$ is selected from, hydrogen, methyl benzyl, C(=O)R$^c$, and SO$_2$CH$_3$;

or R$^2$, together with R$^1$, forms a 4 to 7 membered ring, containing 0, 1, or 2 heteroatoms independently selected from nitrogen, oxygen, and sulfur; unsubstituted or substituted on carbon or nitrogen with one, two or three substituents independently selected from R$^b$, wherein one or two of the carbon substituents may be oxo, and wherein the ring has one degree of unsaturation.

In another embodiment of the present invention, $R^3$ is selected from: hydrogen, $C_{1-6}$alkyl, $C_{1-6}$alkyloxy-, trifluoromethyl, trifluoromethoxy-, halo, and $C_{3-7}$cycloalkyl; wherein the alkyl moiety is unsubstituted or substituted with one, two, or three substituents independently selected from R$^a$, and the cycloalkyl moiety is unsubstituted or substituted with one to three substituents selected from R$^b$ and oxo.

In one class of this embodiment, $R^3$ is selected from: hydrogen, $C_{1-4}$alkyl, methyloxy-, trifluoromethyl, trifluoromethoxy-, halo, and cyclopropyl; wherein the alkyl moiety is unsubstituted or substituted with one, or two independently selected from R$^a$.

In one subclass of this class, $R^3$ is selected from: hydrogen, and methyl.

In one embodiment of the present invention, $R^4$ is selected from: hydrogen, and —$CH_2$—$R^8$.

In one class of this embodiment, $R^4$ is selected from: hydrogen, $C_{1-5}$alkyl, benzyl, pyridylmethyl-, cycloalkyl-methyl-, cycloheteroalky-methyl-; wherein alkyl moieties are unsubstituted or substituted with one, two, three or four substituents independently selected from $R^a$, and the cycloalkyl, cycloheteroalkyl, phenyl and pyridyl moieties are unsubstituted or substituted with one, two, or three substituents independently selected from $R^b$.

In one embodiment of the present invention, $R^5$ and $R^6$ are each independently selected from: hydrogen, $C_{1-10}$alkyl, $C_{2-10}$ alkenyl, $C_{2-10}$alkynyl, aryl, aryl$C_{1-4}$alkyl-, heteroaryl, heteroaryl$C_{1-4}$alkyl-, cycloalkyl, cycloalkyl$C_{1-4}$alkyl-, trifluoromethyl, —C(O)—$R^c$, —$CO_2R^c$, —C(O)C(O)$OR^e$, —C(O)C(O)$NR^eR^f$, —S(O)$_m R^c$, and —C(O)N($R^d$)S(O)$_m R^c$; wherein the alkyl, alkenyl, alkynyl moieties are unsubstituted or substituted with one or two $R^a$ substituents, and the cycloalkyl, heteroaryl and aryl moieties are unsubstituted or substituted with one or two $R^b$ substituents;
or $R^5$ and $R^6$ together form =CH—N($R^e$)($R^f$).

In one class of this embodiment, $R^5$ is selected from: hydrogen, $C_{1-6}$alkyl, trifluoromethyl, and methylcarbonyl-, wherein the alkyl moieties are unsubstituted or substituted with one or two $R^a$ substituents; and $R^6$ is each selected from: hydrogen, $C_{1-6}$alkyl, phenyl, benzyl, trifluoromethyl, —C(O)—$R^c$, —$CO_2R^c$, and —S(O)$_2CH_3$; wherein the alkyl moieties are unsubstituted or substituted with one or two $R^a$ substituents, and the phenyl moieties are unsubstituted or substituted with one or two $R^b$ substituents;
or $R^5$ and $R^6$ together form =CH—N($CH_3$)$_2$.

In one subclass of this class, $R^5$ is selected from: hydrogen, methyl, and methlcarbonyl-, and $R^6$ is hydrogen, $C_{1-3}$alkyl, methyl benzyl, —C(=O)$R^c$, and —SO$_2CH_3$, or $R^5$ and $R^6$, together with the nitrogen to which they are attached, form a 5-membered cycloheteroalkyl ring.

In another subclass of this class, $R^5$ is selected from: hydrogen, methyl, and methlcarbonyl-, and $R^6$ is hydrogen, $C_{1-3}$alkyl, methyl benzyl, and —C(=O)$R^c$, or $R^5$ and $R^6$, together with the nitrogen to which they are attached, form a 5-membered cycloheteroalkyl ring.

In one embodiment of the present invention, $R^7$ is selected from: hydrogen, $C_{1-10}$alkyl, $C_{2-10}$alkenyl, $C_{2-10}$alkynyl, cycloalkyl, cycloalkyl-$C_{1-10}$alkyl-, cycloheteroalkyl, cycloheteroalkyl-$C_{1-10}$alkyl-, aryl, heteroaryl, aryl-$C_{1-10}$alkyl-, heteroaryl-$C_{1-10}$alkyl-, —$OR^e$, —$NR^dR^e$, —NH(C=O)$OR^e$, and —$NR^dSO_2R^e$; wherein the alkyl, alkenyl, and alkynyl moieties are unsubstituted or substituted with one, two, three or four substituents independently selected from $R^a$, and the cycloalkyl, cycloheteroalkyl, aryl and heteroaryl moieties are unsubstituted or substituted with one, two, three or four substituents independently selected from $R^b$.

In one class of this embodiment, $R^7$ is selected from: hydrogen, $C_{1-6}$alkyl, cycloalkyl, cycloheteroalkyl, aryl, heteroaryl, heteroaryl-$C_{1-10}$alkyl-, —$OR^e$, —$NR^dR^e$, and —NH(C=O)$OR^e$; wherein the alkyl moieties are unsubstituted or substituted with one, two, or three substituents independently selected from $R^a$, and the cycloalkyl, cycloheteroalkyl, aryl and heteroaryl moieties are unsubstituted or substituted with an $R^b$ substituent.

In one subclass of this class, $R^7$ is selected from: hydrogen, $C_{1-3}$alkyl, —$OR^e$, and —$NR^dR^e$; wherein the alkyl moieties are unsubstituted or substituted with one, two, or three substituents independently selected from $R^a$.

In another subclass of this class, $R^7$ is selected from: $C_{1-3}$alkyl, unsubstituted or substituted with halogen; —$OR^e$; and —$NR^dR^e$; wherein $R^d$ is selected from hydrogen and methyl, and $R^e$ is selected from hydrogen and $C_{1-3}$alkyl.

In one embodiment of the present invention, $R^8$ is selected from: hydrogen, —(CH$_2$)$_n$OC(O)$R^e$, $C_{1-8}$alkyl, $C_{2-8}$ alkenyl, $C_{2-8}$alkynyl, cycloalkyl, cycloalkyl-$C_{1-8}$alkyl-, cycloheteroalkyl, cycloheteroalkyl-$C_{1-8}$ alkyl-, aryl, heteroaryl, aryl-$C_{1-8}$alkyl-, and heteroaryl-$C_{1-8}$alkyl-; wherein the alkyl, alkenyl, and alkynyl moieties are unsubstituted or substituted with one, two, three or four substituents independently selected from $R^a$, and the cycloalkyl, cycloheteroalkyl, aryl and heteroaryl moieties are unsubstituted or substituted with one, two, three or four substituents independently selected from $R^b$.

In one class of this embodiment, $R^8$ is selected from: hydrogen, —(CH$_2$)$_n$OC(O)$R^e$, $C_{1-6}$alkyl, cycloalkyl, cycloheteroalkyl, phenyl, and heteroaryl; wherein the alkyl moieties are unsubstituted or substituted with one, two, three or four substituents independently selected from $R^a$, and the cycloalkyl, cycloheteroalkyl, phenyl and heteroaryl moieties are unsubstituted or substituted with one, two, or three substituents independently selected from $R^b$.

In one subclass of this class, $R^8$ is selected from: hydrogen, —(CH$_2$)$_n$OC(O)$CH_3$, $C_{1-6}$alkyl, $C_{3-6}$cycloalkyl, tetrahydrofuranyl, phenyl, and pyridyl; wherein the alkyl moieties are unsubstituted or substituted with one, or two substituents independently selected from —$OR^e$, and the tetrahydrofuranyl, phenyl and pyridyl moieties are unsubstituted or substituted with one, two, or three substituents independently selected from $OR^e$, halogen, —$NR^eR^f$, —$COCH_3$, —C(O)$OCH_3$, —CN, and $C_{1-3}$ alkyl.

In one embodiment of the present invention, $Ar^1$ and $Ar^2$ are independently selected from: aryl, and heteroaryl; wherein aryl and heteroaryl are unsubstituted or substituted with one, two, three or four substituents independently selected from $R^b$.

In one class of this embodiment, $Ar^1$ and $Ar^2$ are independently selected from: phenyl, and pyridyl; wherein phenyl and heteroaryl are unsubstituted or substituted with one, two, or three substituents independently selected from $R^b$.

In one subclass of this class, $Ar^1$ and $Ar^2$ are each phenyl, either unsubstituted or substituted with one or two substituents independently selected from $R^b$.

In yet another subclass, $Ar^1$ is phenyl, substituted with one or two substituents independently selected from halogen and methyl. In another subclass, the substituents are selected from chloro and methyl.

In yet another subclass, $Ar^2$ is phenyl, either unsubstituted or substituted with one or two halogen substituents. In another subclass, the substituents are selected from fluoro and chloro.

In one embodiment of the present invention, each $R^a$ is independently selected from: —$OR^e$, —$NR^dS(O)_m R^c$, —$NO_2$, halogen, —$S(O)_m R^c$, —$SR^e$, —$S(O)_2OR^e$, —$S(O)_m NR^eR^f$, —$NR^eR^f$, —O(C$R^eR^f$)$_n NR^eR^f$, —C(O)$R^c$, —$CO_2R^c$, —$CO_2$(C$R^eR^f$)$_n CONR^eR^f$, —OC(O)$R^c$, —CN, —C(O)$NR^eR^f$, —$NR^dC(O)R^c$, —$NR^dC(O)OR^e$, —$NR^dC(O)NR^dR^e$, —$CR^d$(N—$OR^e$), $CF_3$, —$OCF_3$, $C_{3-8}$cycloalkyl, and cycloheteroalkyl; wherein cycloalkyl and cycloheteroalkyl moieties are unsubstituted or substituted with one, two or three substituents independently selected from $R^h$.

In one class of this embodiment, each $R^a$ is independently selected from: —$OR^e$, —$NHS(O)_2R^c$, —$NO_2$, halogen, —$S(O)_2R^c$, methylthio, —$S(O)_2OR^e$, —$S(O)_2NR^eR^f$, —$NR^eR^f$, —O(CH$_2$)$_n NR^eR^f$, —C(O)$R^c$, —$CO_2R^c$, —$CO_2$(CH$_2$)$_n CONR^eR^f$, —OC(O)$R^c$, —CN, —C(O)$NR^eR^f$, —NHC(O)$R^c$, —NHC(O)O$R^e$, —NHC(O)N$R^d R^e$, —C$R^d$(N—O$R^e$), CF$_3$, —OCF$_3$, and cyclopropyl; wherein cyclopropyl is unsubstituted or substituted with one or two substituents independently selected from $R^h$.

In one subclass of this class, each $R^a$ is independently selected from: —O$R^e$, halogen, —N$R^e R^f$, —C(O)$R^c$, —CO$_2 R^c$, —OC(O)$R^c$, —CN, CF$_3$, and —OCF$_3$.

In another subclass of this class, each $R^a$ is independently selected from: hydroxy, methoxy-, halogen, methylcarbonyl-, —CO$_2 R^c$, —OC(O)$R^c$, —CN, CF$_3$, and —OCF$_3$.

In one embodiment of the present invention, each $R^b$ is independently selected from: $R^a$, $C_{1-10}$alkyl, cycloalkyl $C_{1-4}$alkyl-, cycloheteroalkyl$C_{1-4}$alkyl-, aryl, aryl$C_{1-4}$alkyl-, heteroaryl, and heteroaryl$C_{1-4}$alkyl-; wherein cycloalkyl, cycloheteroalkyl, aryl and heteroaryl moieties are unsubstituted or substituted with one, two or three substituents independently selected from $R^h$.

In one class of this embodiment, each $R^b$ is independently selected from: $R^a$, $C_{1-6}$alkyl, cycloalkylmethyl-, cycloheteroalkylmethyl-, phenyl, benzyl, pyridyl, and pyridylmethyl-; wherein cycloalkyl, cycloheteroalkyl, phenyl and pyridyl moieties are unsubstituted or substituted with one, two or three substituents independently selected from $R^h$.

In one subclass of this class, each $R^b$ is independently selected from: —O$R^e$, —NHS(O)$_2 R^c$, —NO$_2$, halogen, —S(O)$_2 R^c$, methylthio-, —S(O)$_2$O$R^e$, —S(O)$_2$N$R^e R^f$, —N$R^e R^f$, —O(CH$_2$)$_n$N$R^e R^f$, —C(O)$R^c$, —CO$_2 R^c$, —CO$_2$(CH$_2$)$_n$CON$R^e R^f$, —OC(O)$R^c$, —CN, —C(O)N$R^e R^f$, —NHC(O)$R^c$, —NHC(O)O$R^e$, —NHC(O)N$R^d R^e$, —C$R^d$(N—O$R^e$), —CF$_3$, —OCF$_3$, cyclopropyl, $C_{1-6}$alkyl, cycloalkylmethyl-, cycloheteroalkylmethyl-, phenyl, benzyl, pyridyl, and pyridylmethyl-; wherein cycloalkyl, cycloheteroalkyl, phenyl and pyridyl moieties are unsubstituted or substituted with one, two or three substituents independently selected from $R^h$.

In yet another subclass of this class, each $R^b$ is independently selected from —O$R^e$, halogen, —C(O)$R^c$, —CO$_2 R^c$, —CN, —CF$_3$, —OCF$_3$, $C_{1-6}$alkyl, and benzyl; wherein phenyl moieties are unsubstituted or substituted with one or two substituents independently selected from $R^h$.

In one embodiment of the present invention, each $R^c$ is independently selected from: hydrogen, $C_{1-10}$alkyl, $C_{2-10}$alkenyl, $C_{2-10}$alkynyl, $C_{1-8}$ perfluoroalkyl, cycloalkyl, cycloalkyl-$C_{1-10}$alkyl, cycloheteroalkyl, cycloheteroalkyl-$C_{1-10}$alkyl, aryl, heteroaryl, aryl-$C_{1-10}$alkyl, heteroaryl-$C_{1-10}$alkyl, and —N$R^d R^d$; wherein each alkyl, cycloalkyl, cycloheteroalkyl, aryl, and heteroaryl moiety may be substituted with one or two $R^h$ substituents, and alkyl, cycloalkyl, cycloheteroalkyl may be substituted on a carbon or sulfur atom with one or two oxo substituents.

In one class of this embodiment, each $R^c$ is independently selected from: hydrogen, $C_{1-6}$alkyl, trifluoromethyl, $C_{3-7}$cycloalkyl, $C_{3-7}$cycloalkyl-methyl-, cycloheteroalkyl, cycloheteroalkyl-methyl-, phenyl, pyridyl, benzyl, pyridylmethyl-, and —N$R^d R^d$; wherein each alkyl, cycloalkyl, cycloheteroalkyl, aryl, and heteroaryl moiety may be substituted with one or two $R^h$ substituents, and alkyl, cycloalkyl, cycloheteroalkyl may be substituted on a carbon or sulfur atom with one or two oxo substituents.

In one subclass of this class, each $R^c$ is independently selected from: hydrogen, $C_{1-6}$alkyl, and —N$R^d R^d$; wherein each alkyl moiety may be substituted with one or two substituents selected from $R^h$ and oxo.

In one embodiment of the present invention, each $R^d$ is independently selected from hydrogen, $C_{1-10}$alkyl, $C_{1-10}$alkylcarbonyl-, aryl, arylcarbonyl-, arylsulfonyl-, and $C_{1-10}$alkylsulfonyl-; wherein the alkyl and aryl groups may be unsubstituted or substituted with one, two or three substituents independently selected from $R^h$.

In one class of this embodiment, each $R^d$ is independently selected from hydrogen, $C_{1-6}$alkyl, $C_{1-6}$alkylcarbonyl-, phenyl, phenylcarbonyl-, phenylsulfonyl-, and $C_{1-6}$alkylsulfonyl-, wherein the alkyl and phenyl groups may be unsubstituted or substituted with one, two or three substituents independently selected from $R^h$.

In one subclass of this class, each $R^d$ is independently selected from hydrogen, and $C_{1-6}$alkyl; wherein the alkyl group may be unsubstituted or substituted with one or two substituents independently selected from $R^h$.

In another subclass of this class, each $R^d$ is independently selected from hydrogen, methyl, and ethyl.

In one embodiment of the present invention, $R^e$ and $R^f$ are independently selected from hydrogen, $C_{1-10}$alkyl, $C_{2-10}$alkenyl, $C_{2-10}$alkynyl, trifluoromethyl, cycloalkyl, cycloalkyl-$C_{1-10}$ alkyl-, cycloheteroalkyl, cycloheteroalkyl-$C_{1-10}$alkyl-, aryl, heteroaryl, aryl-$C_{1-10}$ alkyl-, and heteroaryl-$C_{1-10}$ alkyl- at each occurrence; or when bonded to the same atom, $R^e$ and $R^f$ together with the atom to which they are attached form a ring of 5 to 7 members containing 0, 1, or 2 heteroatoms independently selected from oxygen, sulfur and nitrogen; and each $R^e$ and $R^f$ moiety may be unsubstituted or substituted on a carbon or nitrogen atom with one, two or three substituents selected from $R^h$.

In one class of this embodiment, $R^e$ and $R^f$ are independently selected from hydrogen, $C_{1-6}$alkyl, trifluoromethyl, cycloalkyl, cycloalkyl-methyl-, cycloheteroalkyl, cycloheteroalkylmethyl-, phenyl, pyridyl, benzyl, and pyridylmethyl- at each occurrence; or when bonded to the same atom, $R^e$ and $R^f$ together with the atom to which they are attached form a ring of 5 to 7 members containing 0, 1, or 2 heteroatoms independently selected from oxygen, sulfur and nitrogen; and each $R^e$ and $R^f$ moiety may be unsubstituted or substituted on a carbon or nitrogen atom with one, two or three substituents selected from $R^h$.

In one subclass of this class, $R^e$ and $R^f$ are independently selected from hydrogen and $C_{1-6}$alkyl, wherein alkyl is unsubstituted or substituted on a carbon or nitrogen atom with one or two substituents selected from $R^h$.

In another subclass, $R^e$ and $R^f$ are independently selected from hydrogen and $C_{1-3}$alkyl.

In one embodiment of the present invention, each $R^h$ is independently selected from: halogen, $C_{1-10}$alkyl, $C_{3-8}$cycloalkyl, cycloheteroalkyl, aryl, aryl$C_{1-4}$alkyl-, heteroaryl, heteroaryl$C_{1-4}$alkyl-, —O$R^i$, —N$R^k$S(O)$_m R^i$, —S(O)$_m R^i$, —S$R^i$, —S(O)$_2$O$R^i$, —N$R^i R^i$, —O(C$R^k R^k$)$_n$N$R^i R^i$, —C(O)$R^i$, —CO$_2 R^i$, —CO$_2$(C$R^k R^k$)$_n$CON$R^i R^i$, —OC(O)$R^i$, —CN, —C(O)N$R^i R^i$, —N$R^k$C(O)$R^i$, —OC(O)N$R^i R^i$, —N$R^k$C(O)O$R^i$, —N$R^k$C(O)N$R^i R^i$, —CF$_3$, and —OCF$_3$.

In one class of this embodiment, each $R^h$ is independently selected from: halogen, $C_{1-6}$alkyl, $C_{3-6}$cycloalkyl, cycloheteroalkyl, phenyl, benzyl, pyridyl, pyridylmethyl-, —O$R^i$, —NHS(O)$_2 R^i$, —S(O)$_2 R^i$, —S$R^i$, —S(O)$_2$O$R^i$, —N$R^i R^i$, —O(CH$_2$)$_n$N$R^i R^i$, —C(O)$R^i$, —CO$_2 R^i$, —CO$_2$(CH$_2$)$_n$CON$R^i R^i$, —OC(O)$R^i$, —CN, —C(O)N$R^i R^i$, —NHC(O)$R^i$, —OC(O)N$R^i R^i$, —NHC(O)O$R^i$, —NHC(O)N$R^i R^i$, —CF$_3$, and —OCF$_3$.

In one subclass of this class, each $R^h$ is independently selected from: halogen; $C_{1-3}$alkyl; hydroxy; methoxy-; —N$R^i R^i$, wherein $R^i$ is selected from hydrogen and methyl; methylcarbonyloxy-; —CF$_3$; and —OCF$_3$.

In one embodiment of the present invention, each $R^i$ is independently selected from: hydrogen, $C_{1-8}$alkyl, $C_{2-8}$ alkenyl, $C_{2-8}$alkynyl, $C_{1-6}$ perfluoroalkyl, cycloalkyl, cycloalkyl-$C_{1-6}$alkyl-, cycloheteroalkyl, cycloheteroalkyl-$C_{1-6}$alkyl-, aryl, heteroaryl, aryl-$C_{1-6}$alkyl-, and heteroaryl-$C_{1-6}$alkyl-;

wherein each alkyl, cycloalkyl, cycloheteroalkyl, aryl, and heteroaryl moiety is unsubstituted or substituted with one or two substituents selected from hydroxy, methoxy, acetoxy, halogen, cyano, and trifluoromethyl;

and each alkyl, cycloalkyl, cycloheteroalkyl moiety may be substituted on a carbon or sulfur atom with one or two oxo substituents; and cycloalkyl, cycloheteroalkyl, aryl and heteroaryl may be substituted with methyl.

In one class of this embodiment, each $R^i$ is independently selected from: hydrogen, $C_{1-3}$alkyl, trifluoromethyl, and cyclopropyl;

wherein each alkyl and cycloalkyl moiety is unsubstituted or substituted with one or two substituents selected from oxo, hydroxy, methoxy, acetoxy, halogen, cyano, and trifluoromethyl.

In one subclass of this class, each $R^i$ is independently selected from: hydrogen, and methyl.

In one embodiment of the present invention, each $R^k$ is independently selected from hydrogen, $C_{1-10}$alkyl, $C_{1-10}$alkylcarbonyl-, aryl $C_{1-3}$alkyl, and arylcarbonyl, wherein the each alkyl and aryl moeity is unsubstituted or substituted with one, two or three substituents independently selected from hydroxy, methoxy, acetoxy, halogen, trifluoromethyl, cyano, and aryl may also be substituted with methyl.

In one class of this embodiment, each $R^k$ is independently selected from hydrogen, and $C_{1-3}$alkyl, wherein alkyl may be unsubstituted or substituted with one, two or three substituents independently selected from hydroxy, methoxy, acetoxy, halogen, and trifluoromethyl.

In one subclass of this class, each $R^k$ is independently selected from hydrogen, and methyl.

In one embodiment of the present invention, m is selected from 1 and 2. In one class of the present invention, m is 1. In another class of the present invention, m is 2.

In one embodiment of the present invention, n is selected from 1, 2, and 3. In one class of this embodiment, n is 1.

Still another embodiment of the present invention comprises compounds of structural formula IA:

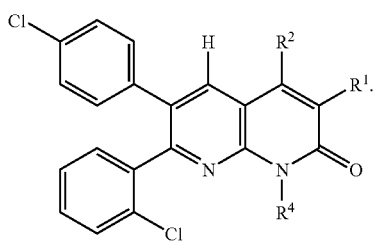

IA

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec-, iso- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, 1,3-benzodioxol-5-yl, and the like. A preferred aryl substituent is phenyl.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzothiazolyl, furo(2,3-b)pyridyl, quinolyl, indolyl, isoquinolyl, oxazolidinyl, and the like. The heteroaryl ring may be substituted on one or more carbon atoms. In one embodiment of the present invention, heteroaryl is pyridinyl, pyrazinyl, benzimidazolyl, imidazolyl, and furanyl. In one class of this embodiment, heteroaryl is pyridinyl, pyrazinyl, and furanyl.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also refers to bridged rings, and also includes monocyclic heterocycle fused to an aryl or heteroaryl group in which the point of attachment is on the non-aromatic portion. The term also includes partially unsaturated monocyclic rings that are not aromatic, such as 2- or 4-pyridones attached through the nitrogen or N-substituted-(1H,3H)-pyrimidine-2,4-diones (N-substituted uracils). The cycloheteroalkyl ring may be substituted on the ring carbons and/or the ring nitrogens. Examples of "cycloheteroalkyl" include: azetidinyl, pyrrolidinyl, piperidinyl, piperazinyl, imidazolidinyl, morpholinyl, dihydroisoindolyl, pyranyl, perhydroazepinyl, tetrahydrofuranyl, dioxanyl, oxanyl, 1-thia-4-aza-cyclohexane (thiomorpholinyl), 2,5-diazabicyclo[2.2.2]octanyl, benzoxazinyl, tetrahydroquinolinyl, tetrahydroisoquinolinyl, dihydroindolyl, dihydroisoindolyl, indolyl, indolinyl, isoindolinyl, isothiazolindinyl, 1,3-dihydro-2-benzofuranyl, benzodioxolyl, hexahydrothienopyridinyl, thienopyridinyl, azacycloheptyl, azabicyclo[3.1.0]hexyl, 2-oxa-5-azabicyclo[2.2.1]heptyl, 2,5-diazabicyclo[2.2.1]heptyl, 2-azabicyclo[2.2.1]heptyl, 7-azabicyclo[2.2.1.]heptyl, 2,4-dizaobicyclo[2.2.2]octyl, 2-azabicyclo[2.2.2]octyl, 3-azabicyclo[3,2,2]nonyl, 2H-pyrrolyl, 4,4-spiro[2,3-dihydrobenzothiophen-3,3-yl]piperidinyl, 4,4-spiro[indoli-3,3-yl]piperidinyl, and the like. In one embodiment of the present invention, cycloheteroalkyl is: azetindinyl, pyrrolidinyl, piperidinyl, piperazinyl, imidazolidinyl, morpholinyl, 1-thia-4-aza-cyclohexane (thiomorpholinyl), isothiazolidinyl, andazabicyclo[3.1.0]hexyl.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

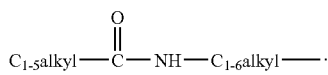

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

It is generally preferable to administer compounds of the present invention as enantiomerically pure formulations.

Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor and mimics the effects of the endogenous regulatory compound, such as contraction, relaxation, secretion, change in enzyme activity, etc. An "antagonist" is a compound, devoid of intrinsic regulatory activity, which produces effects by interfering with the binding of the endogenous agonist or inhibiting the action of an agonist An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith, including left ventricular hypertrophy, as well as treating or preventing obesity in other mammalian species, including canines and felines. The compounds are also useful for the treatment of constipation and chronic intestinal pseudo-obstruction. The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the guinea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lies within the range of from about 0.001 mg to about 100 mg per kg body weight of a mammal, in one embodiment, the ranges is from 0.01 mg to about 50 mg per kg, and in another embodiment, the range is from 0.1 to 10 mg per kg, each of which may be administered in single or divided doses. On the other hand, it may be necessary to use dosages outside these limits in some cases.

For use where a composition for intravenous administration is employed, a suitable dosage range is from about 0.001 mg to about 100 mg in one embodiment from 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day, in one embodiment, the range is from about 0.1 mg to about 10 mg per day. For oral administration, the compositions are preferably provided in the form of tablets containing from 0.01 to 1,000 mg, such as, for example, 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

Ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human or companion animal such as a dog or cat, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course, be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet, cachet, or capsule contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Capsule | mg/capsule |
|---|---|
| Compound of Formula I | 25 |
| Lactose Powder | 573.5 |
| Magnesium Stearate | 1.5 |
| | 600 |

-continued

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, and other anti-obesity agents, as well as antidiabetic agents, lipid lowering agents, and antihypertensive agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related conditions, such that together they give effective relief.

Suitable agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone; rosiglitazone; troglitazone; BRL49653; CLX-0921; 5-BTZD, and GW-0207, LG-100641, and LY-300512, and the like and compounds disclosed in WO97/10813, 97/27857, 97/28115, 97/28137, 97/27847, 03/000685, 03/027112, 03/035602, 03/048130, 03/055867, and the like; (2) biguanides such as buformin; metformin; and phenformin, and the like; (3) protein tyrosine phosphatase-1B (PTP-1B) inhibitors, such as ISIS 113715, and those disclosed in WO 03/032916, WO 03/032982, WO 03/041729, WO 03/055883; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride; and A4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$), and the like; (12) non-thiazolidinediones such as JT-501, and farglitazar (GW-2570/GI-262579), and the like; (13) PPARα/γ dual agonists such as BVT-142, CLX-0940, GW-1536, GW1929, GW-2433, KRP-297, L-796449, LR-90, MK-0767, SB 219994, muraglitazar and reglitazar (JTT-501) and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/004458, WO 03/016265, WO 03/018010, WO 03/033481, WO 03/033450, WO 03/033453, WO 03/043985, WO 03/053976; and (14) other insulin sensitizing drugs; (15) VPAC2 receptor agonists; (16) GLK modulators, such as those disclosed in WO 03/015774; (17) retinoid modulators such as those disclosed in WO 03/000249; (18) GSK 3beta/GSK 3 inhibitors such as 4-[2-(2-bromophenyl)-4-(4-fluorophenyl)-1H-imidazol-5-yl]pyridine and those compounds disclosed in WO 03/024447, WO 03/037869, WO 03/037877, WO 03/037891, WO 03/068773, EP 1295884, EP 1295885, and the like; (19) glycogen phosphorylase (HGLPa) inhibitors, such as those disclosed in WO 03/037864; (20) ATP consumption promotors such as those disclosed in WO 03/007990; (21) TRB3 inhibitors, (22) vanilloid receptor ligands such as those disclosed in WO 03/049702, (23) hypoglycemic agents such as those disclosed in WO 03/015781, WO 03/040114, (24) glycogen synthase kinase 3 inhibitors such as those disclosed in WO 03/035663, (25) and agents such as those disclosed in WO 99/51225 and US 20030134890; and WO 01/24786, WO 03/059870; (26) Insulin-responsive DNA binding protein-1 (IRDBP-1) as disclosed in WO 03/057827, and the like; (27) Adenosine A2 antagonists such as those disclosed in WO 03/035639, WO 03/035640, and the like; and (b) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, fluvastatin, lovastatin, pravastatin, rivastatin, rosuvastatin, simvastatin, and ZD4522, and the like and compounds disclosed in WO 03/033481, particularly simvastatin; (3) HMG-CoA synthase inhibitors; (4) cholesterol absorption inhibitors such as stanol esters, beta-sitosterol, sterol glycosides such as tiqueside; and azetidinones such as ezetimibe, and the like; (5) acyl coenzyme A-cholesterol acyl transferase (ACAT) inhibitors such as avasimibe, eflucimibe, KY505, SMP 797, and the like; (6) CETP inhibitors such as mT 705, torcetrapib, CP 532,632, BAY63-2149, SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gernfibrozil, GW 7647, BM 170744, LY518674; and other fibric acid derivatives, such as Atromid®, Lopid® and Tricor®, and those disclosed in WO 03033456, WO 03/033481, WO 03/043997, WO 03/048116, WO 03/053974, WO 03/059864, WO 03/05875, and the like; (10) FXR receptor modulators such as GW 4064, SR 103912, and the like; (11) LXR receptor modulators such as GW 3965, T9013137, and XTC0179628, and those disclosed in US 20030125357, WO 03/045382, WO 03/053352, WO 03/059874, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; (16) PPARδ agonists such as GW 501516, and GW 590735, and the like, such as those disclosed in WO97/28149, WO 01/79197, WO 02/14291, WO 02/46154, WO 02/46176, WO 02/076957, WO 03/016291, WO 03/033493; (17) triglyceride synthesis inhibitors; (18) microsomal triglyceride transport (MTTP) inhibitors, such as inplitapide, LAB687, and CP346086, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists; (25) PPAR modulators such as those disclosed in WO 99/07357, WO 99/11255, WO 99/2534, WO 99/15520, WO 99/46232, WO 00/12491, WO 00/23442, WO 00/236331, WO 00/236332, WO 00/218355, WO 00/238553, WO 01/25181, WO 01/79150, WO 02/79162, WO 02/100403, WO 02/102780, WO 02/081428, WO 03/016265, WO 03/033453, WO 03/042194, WO 03/043997, WO 03/066581, and the like; (26) niacin-bound chromium, as disclosed in WO 03/039535; (27) substituted acid derivatives disclosed in WO 03/040114; (28) apolipoprotein B inhibitors such as those disclosed in WO 02/090347, WO 02/28835, WO 03/045921, WO 03/047575; (29) Factor Xa modulators such as those disclosed in WO 03/047517, WO 03/047520, WO 03/048081, and the like; and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lernildipine, lercanidipine, nicardipine, nifedipine, nilvadipine, nimodepine, nisoldipine, nitrendipine, manidipine, pranidipine, and vaparnil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sarnpatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin f receptor antagonists such as candesartan, eprosartan, irbesartan, losartan, pratosartan, tasosartan, telmisartan, valsartan, and EXP-3137, F16828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine, tizanidine, and guanobenz, and the like; and (12) aldosterone inhibitors, and the like; (13) angiopoietin-2 binding agents such as those disclosed in WO 03/030833, and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663; (2) NE (norepinephrine) transporter inhibitors, such as GW 320659, despiramine, talsupram, and nomifensine; (3) CB1 (cannabinoid-1 receptor) antagonist/inverse agonists, such as rimonabant (Sanofi Synthelabo), SR-147778 (Sanofi Synthelabo), BAY 65-2520 (Bayer), and SLV 319 (Solvay), and those disclosed in U.S. Pat. Nos. 4,973,587, 5,013,837, 5,081,122, 5,112,820, 5,292, 736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 03/042174, WO 03/51850, WO 03/051851, WO 03/063781, WO03/077847, WO 03/086940, WO 03/084943; and U.S. Pat. No. 6,509,367, EPO No. EP-658546; (4) ghrelin antagonists, such as those disclosed in WO 01/87335, and WO 02/08250; (5) H3 (histamine H3) antagonist/inverse agonists, such as thioperamide, 3-(1H-imidazol-4-yl)propyl N-(4-pentenyl) carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:333-543 (2000)) and histamine H3 receptor modulators such as those disclosed in US 2003/0134835, U.S. Pat. No. 6,316,475, WO 02/074758, WO 02/40461, WO 03/024928, WO 03/024929, WO 03/031432, WO 03/044059, WO 03/059341, WO 03/066604; (6) melanin-concentrating hormone 1 receptor (MCH1R) antagonists, such as T-226296 (Takeda), SNP-7941 (Synaptic), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 03/35055, WO 03/035624, WO 03/045313, WO 03/045920, WO 03/047568, WO 03/045918, WO 03/059289, WO 03/060475; U.S. Pat. No. 6,569,861, and Japanese Patent Application Nos. JP 13226269, and JP 1437059; (7) $MCH_2R$ (melanin concentrating hormone 2R) agonist/antagonists; (8) NPY1 (neuropeptide Y Y1) antagonists, such as BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/23389, WO 01/85690, WO 01/85098, WO 01/85173, WO 01/89528, WO 03/062209, and the like; (9) NPY5 (neuropeptide Y Y5) antagonists, such as 152,804, GW-569180A, GW-594884A, GW-587081x, GW-548118x; FR 235,208; FR226928, FR 240662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; European Patent Nos. EP-01010691, EP-01044970, EP 1306085; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 03/059905, WO 03/066055; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509, WO 03/064375; (13) orexin antagonists, such as SB-334867-A; and those disclosed in WO 99/09024, WO 99/58533, WO 01/96302, WO 01/68609, WO 02/44172, WO 02/51232, WO 02/51838, WO 02/089800, WO 02/090355, WO 03/023561, WO 03/032991, WO 03/037847, WO 03/041711; (14) BRS3 (bombesin receptor subtype 3) agonists; (15) CCK-A (cholecystokinin-A) agonists, such as AR-R 15849, GI 181771, JMV-180, A-71378, A-71623 and SR146131, and those disclosed in U.S. Pat. No. 5,739,106; (16) CNTE (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP424,391, L-692,429 and L-163, 255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) modulators, such as BVT933, DPCA37215, IK264; PNU 22394; WAY161503, R-1065, and YM 348; and those disclosed in U.S. Pat. No. 3,914,250; and WO 01/66548, WO 02/10169, WO 02/36596, WO 02/40456, and WO 02/40457. WO 02/44152, WO 02/48124, WO 02/51844, WO 03/033479, WO 03/057161, WO 03/057213, WO 03/057673, WO 03/057674, WO 03/0153576, and the like; (20) Mc3r (melanocortin 3 receptor) agonists; (21) Mc4r (melanocortin 4 receptor) agonists, such as CHIR86036 (Chiron); ME-10142, ME-10145, and HS-131 (Melacure), and those disclosed in WO 99/64002, WO 00/74679, WO 01/991752, WO 01/0125192, WO 01/52880, WO 01/74844, WO 01/70708, WO 01/70337, WO 01/91752, WO 02/059095, WO 02/059107, WO 02/059108, WO 02/059117, WO 02/06276, WO 02/12166, WO 02/11715, WO 02/12178, WO 02/15909, WO 02/18327, WO 02/38544, WO 02/068387, WO 02/068388, WO 02/067869, WO 02/081430, WO 03/06604, WO 03/007949, WO 03/009847, WO 03/009850, WO 03/013509, WO 03/031410, WO 03/040117, WO 03/040118, WO 03/053927, WO 03/057671, WO 03/061660, WO 03/066597, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365, 633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors, such as those disclosed in WO 02/02101, WO 03/057255, WO 03/059871, and the like; (28) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), and SR 59119A, and those disclosed in U.S. Pat. No. 5,705,515, U.S. Pat. No. 5,451,677; and WO94/18161, WO95/29159, WO97/46556, WO98/04526 and WO98/32753, WO 01/74782, WO 02/32897, WO 03/014113, WO 03/016276, WO 03/016307, WO 03/024948, WO 03/024953, WO 03/035620, WO 03/037881, WO 03/0946, WO 03/044016, WO 03/044017, WO 03/059348; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid antagonists; (37) 11β HSD-1 (11-beta hydroxy steroid dehydrogenase type 1) inhibitors, such as BVT 3498, BVT 2733, 3-(1-adamantyl)-4-ethyl-5-(ethylthio)$_4$H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, WO 01/90090, WO 01/90092, WO 02/072084, WO 03/043999, WO 03/044000, WO 03/044009, WO 03/065983, and the like; (38) SCD-1 (stearoyl-CoA desaturase-1) inhibitors; (39) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444; and the compounds disclosed in WO 01/35988, WO 01/62266, WO 02/083128, WO 02/062764, WO 03/000180, WO 03/000181, WO 03/000250, WO 03/002530, WO 03/002531, WO 03/002553, WO 03/002593, WO 03/004498, WO 03/004496, WO 03/017936, WO 03/024942, WO 03/024965, WO 03/033524, WO 03/035057, WO 03/03567, WO 03/037327, WO 03/055881, WO 03/057144, WO 03/057200, WO 03/057666, WO 03/068748, WO 03/06757, and EP 1 258 476; (40) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, ATL-962, and RHC 80267, and those disclosed in WO 01/77094, and U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as those disclosed in WO 03/026591 and PYY 3-36; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, (50) appetite suppressants such as those disclosed in WO 03/040107, (51) 5HT 6 receptor modulators, such as those disclosed in WO 03/030901, WO 03/035061, WO 03/039547, and the like; (52) 5HT1a modulators such as those disclosed in WO 03/031439, and the like; (53) mGluR5 modulators such as those disclosed in WO 03/029210, WO 03/047581, WO 03/048137, WO 03/051315, WO 03/051833, WO 03/053922, WO 03/059904, and the like; (54) 5HT antagonists such as those disclosed in WO 03/037871, WO 03/037887, and the like; (55) fat resporption inhibitors such as those disclosed in WO 03/053451, and the like; (56) interleukin-6 (IL-6) and modulators thereof as disclosed in WO 03/057237, and the like.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1' (3'H)-isobenzofuran]-4-carboxamide, trans-3'-oxo-N-[1-(3-quinolyl)-4-imidazolyl]spiro[cyclohexane-1,1' (3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]4'-carboxamide, trans-N-[1-(3,5-difluorophenyl)-4-imidazolyl]-3-oxospiro[7-azaisobenzofuran-1(3H),1'-cyclohexane]4'-carboxamide, trans-3-oxo-N-(1-phenyl-4-pyrazolyl)spiro[4-azaisobenzofuran-1(3H), 1'-cyclohexane]4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H), 1'-cyclohexane]4'-carboxamide, and pharmaceutically acceptable salts and esters thereof.

Specific DP-IV inhibitors of use in combination with a compound of the present invention are selected from:

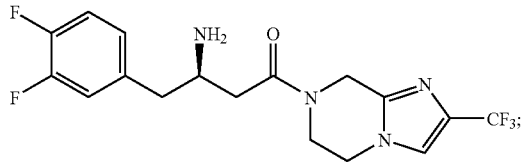

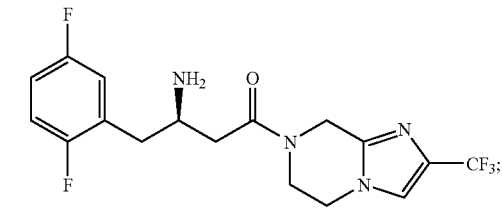

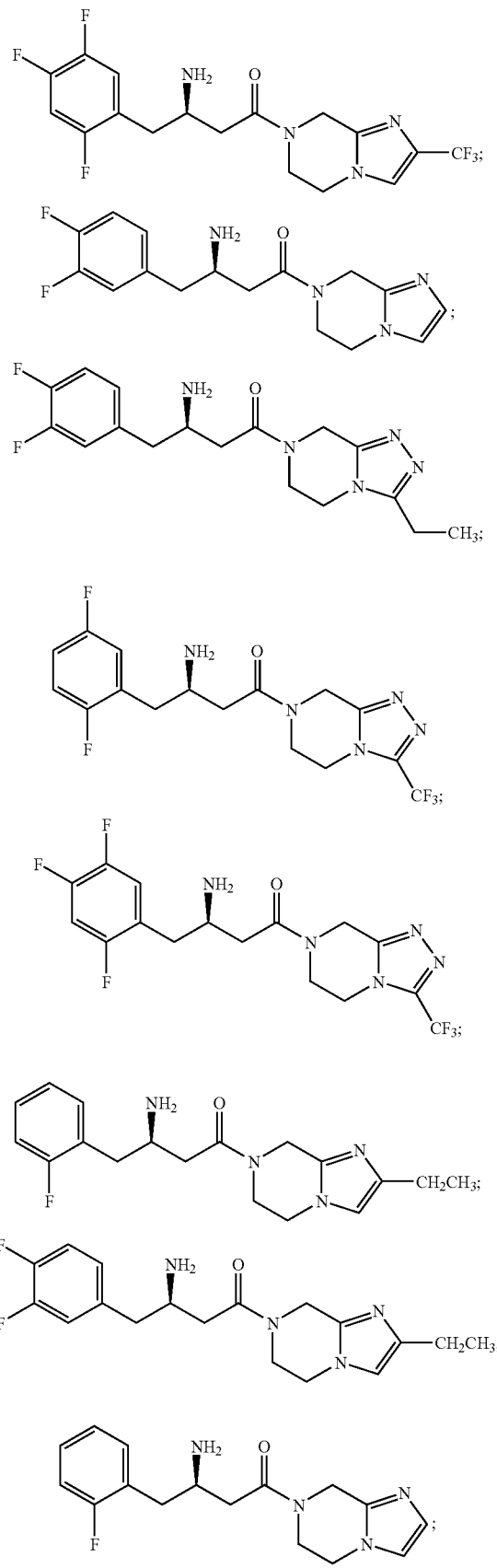
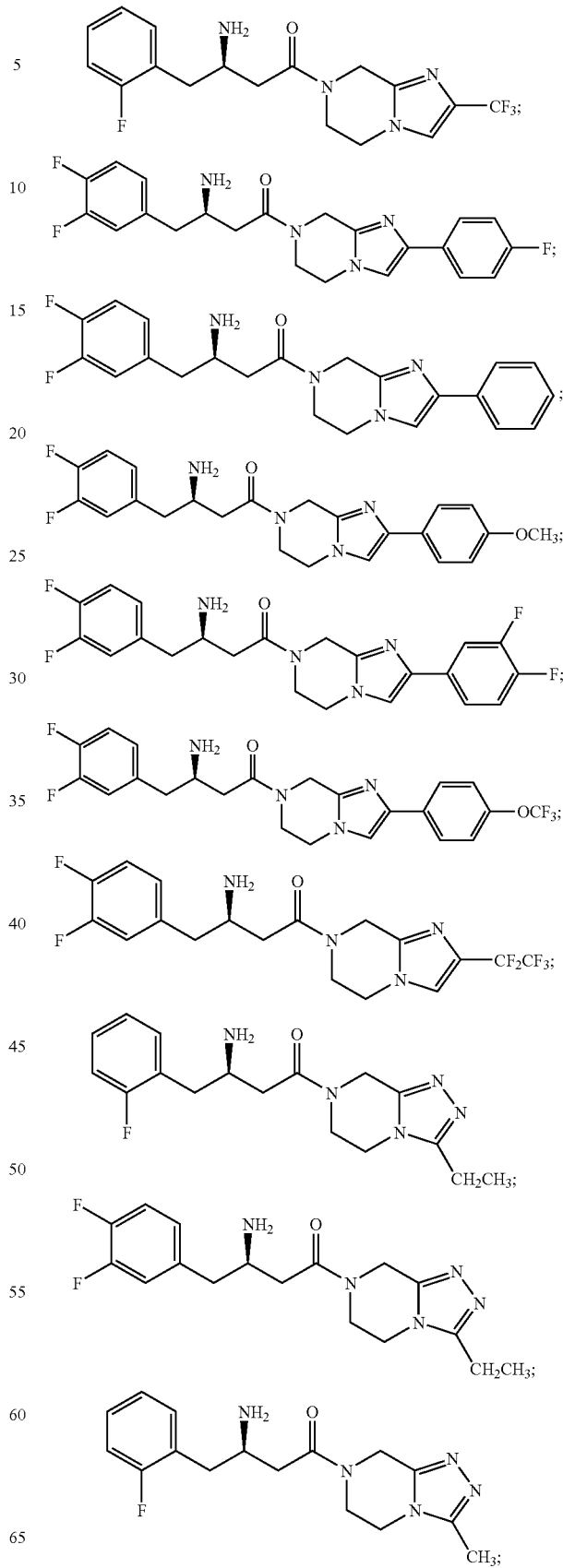

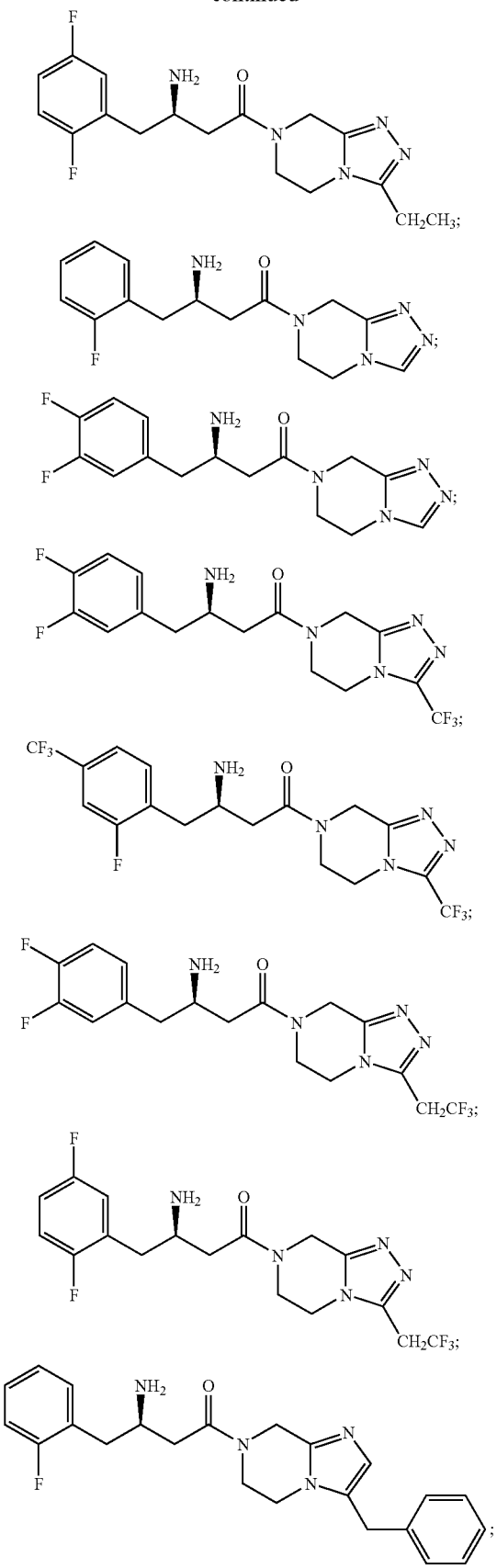
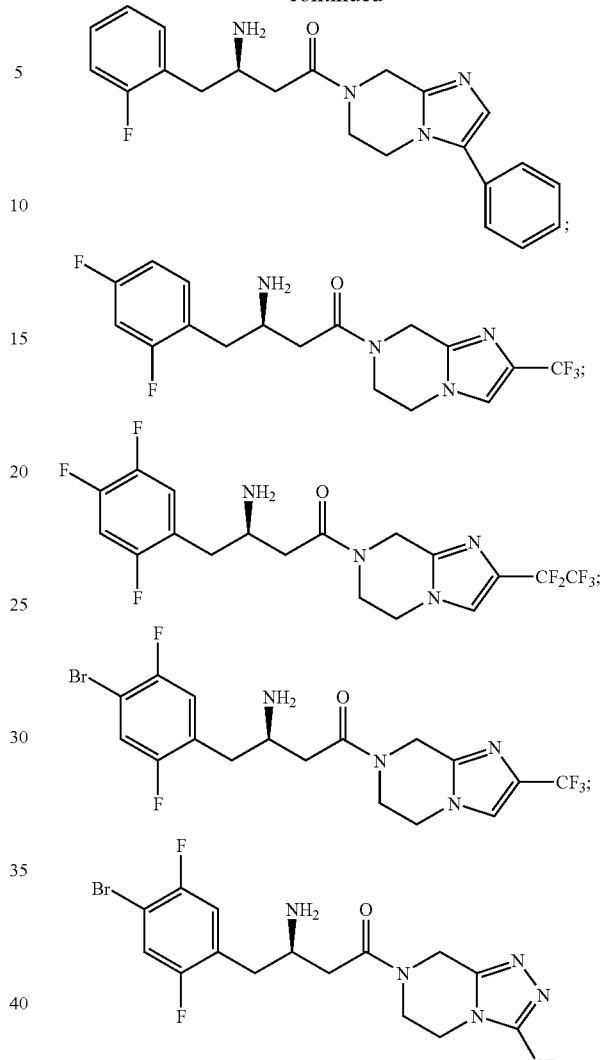

and pharmaceutically acceptable salts thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m². In Asian countries, including Japan, an "obese subject" refers to a subject with at least one obesity-induced or obesity-related co-morbidity that requires weight reduction or that would be improved by weight reduction, with a BMI greater than or equal to 25 kg/m². In Asian countries, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term mammals includes companion animals such as cats and dogs."

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It win be appreciated that for the treatment or prevention of migraine, a compound of the present invention may be used in conjunction with other anti-migraine agents, such as ergotamines or 5-HT agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and those disclosed in WO 03/037905, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Still further, neurokinin-1 (NK-1) receptor antagonists may be favorably employed with the CB1 receptor modulators of the present invention. NK-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 4284 34, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98124441, 98/24442-98124445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include: (±)-(2R3R,2S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ 17493; GW597599; GW679769; R673; R067319; R1124; R1204; SSR146977; SSR240600; T-2328; and T2763; or a pharmaceutically acceptable salt thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and $5\text{-HT}_{1A}$ agonists or antagonists, especially $5\text{-HT}_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-HT}_{1A}$ receptor agonists or antagonists include, in particular, the $5\text{-HT}_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

In particular, compounds of structural formula I are useful for aiding in stopping consumption of tobacco and are useful in treating nicotine dependence and nicotine withdrawal. The compounds of formula I produce in consumers of nicotine, such as tobacco smokers, a total or partial abstinence from smoking. Further, withdrawal symptoms are lessened and the weight gain that generally accompanies quitting tobacco consumption is reduced or nonexistent. For smoking cessation, the compound of form I may be used in combination with a nicotine agonist or a partial nicotine agonist, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-$HT_{2A}$ receptor antagonists, examples of which include MDL100907, SB-247853 and fananserin. Also of use in combination with a CB1 receptor modulator are the serotonin dopamine antagonists (SDAs) which are believed to combine 5-$HT_2A$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described previously.

It will be appreciated that a combination of a conventional anti-asthmatic drug with a CB1 receptor modulator may provide an enhanced effect in the treatment or prevention of asthma and may be used for the manufacture of a medicament for the treatment or prevention of asthma.

The present invention also provides a method for the treatment or prevention of asthma, comprising administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including, β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3, such as those disclosed in WO 03/068759, and the like; and pharmaceutically acceptable salts thereof.

It will be appreciated that a combination of a conventional anti-constipation drug with a CB1 receptor modulator may provide an enhanced effect in the treatment or prevention of constipation or chronic intestinal pseudo-obstruction, and for use for the manufacture of a medicament for the treatment or prevention of constipation or chronic intestinal pseudo-obstruction.

The present invention also provides a method for the treatment or prevention of constipation or chronic intestinal pseudo-obstruction, comprising administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof. A particularly suitable class of osmotic agents include, but are not limited to sorbitol, lactulose, polyethylene glycol, magnesium, phosphate, and sulfate; and pharmaceutically acceptable salts thereof. A particularly suitable class of laxatives and detergent laxatives, include, but are not limited to, magnesium, and docusate sodium; and pharmaceutically acceptable salts thereof. A particularly suitable class of bulking agents include, but are not limited to, psyllium, methylcellulose, and calcium polycarbophil; andpharmaceutically acceptable salts thereof. A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment or prevention of cirrhosis of the liver, and for use for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans and companion animals such as dogs or cats.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples: Ac: acyl; brine: saturated sodium chloride solution; DMAP: 4-dimethylaminopyridine; DMF: dimethyl-formamide; DMSO: dimethylsulfoxide; EDC: 1-ethyl-3-(3-dimethylaminopropyl)-carbodiimide hydrochloride; Et: ethyl; EtOAc: ethyl acetate; g or gm: gram; h or hr: hours; HOAc: acetic acid; HOBt: 1-hydroxybenzotriazole; HPLC: high pressure liquid chromatography; HPLC/MS: high pressure liquid chromatography/mass spectroscopy; in vacuo: rotoevaporation; LC-MS or LCMS: liquid chromatography-mass spectrum; Me: methyl; MeMgBr: methyl magnesium bromide; mg: milligram; MHz: megahertz; min: minutes; mL: milliliter; MPLC: medium pressure liquid chromatography; MS or ms: mass spectrum; N/A: Not applicable; Ph: phenyl; rb: round bottom; rt or RT: room temperature; Rt: retention time; TFA: trifluoroacetic acid; THF: tetrahydrofuran; TLC: thin layer chromatography; uL, ul, μL or μl: microliter; UV: ultra-violet.

The following reaction schemes illustrate methods which may be employed for the synthesis of the novel 1,8-naphthyridin-2(1H)-ones of structural formula I described in this invention. All substituents are as defined above unless indicated otherwise. Several strategies based upon synthetic transformations known in the literature of organic synthesis may be employed for the preparation of the title compounds of general formula I. A preferred synthetic process which is shown retrosynthetically in reaction Scheme 1 proceeds through a suitably substituted 2-pyridone of general formula 2 wherein the substituent labeled X is a functional group as described below. The 2-pyridone of general formula 2 is in turn derived from a 1,2-diarylethanone of general formula 1. Reaction Schemes 2-11 illustrate in detail the preferred methods for the synthesis of the title compounds of general formula I in the forward sense.

Scheme I

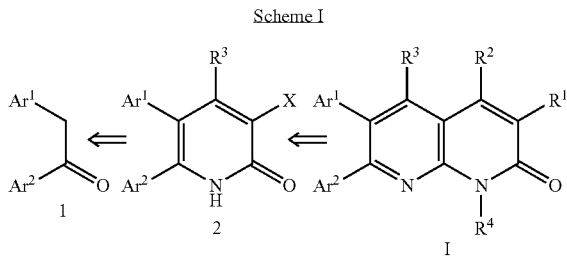

1,2-Diarylethanones of general formula 1 may be available commercially or they can be synthesized using one of several methods known in the art of organic synthesis. Scheme 2 illustrates two methods for the synthesis of the 1,2-diarylethanones of general formula 1. In the first example (equation 1), a substituted arylmethyl bromide of general formula 3 is converted to a Grignard reagent with magnesium metal in a solvent such as THF at a temperature between room temperature and the refluxing temperature of the solvent. The resulting Grignard reagent is then added to a substituted arylnitrile of general formula 4. Acidic hydrolysis of the reaction mixture followed by extraction of the organic product affords a 1,2-diarylethanone of general formula 1 as shown. An alternative synthesis of 1,2-diarylethanones 1 which is preferred when either of the aryl groups $Ar^1$ or $Ar^2$ are optionally substituted with functional groups that are reactive with Grignard reagents is shown at the bottom of reaction Scheme 2 (equation 2). Here a substituted arylacetic acid of general formula 5 is reacted at low temperature (−78° to −50° C.) with two equivalents of a strong base such as lithium bis(trimethylsilylamide) in an aprotic solvent such as THF. This doubly deprotonates the arylacetic acid 5 and generates a dianion which undergoes a Dieckmann reaction when the substituted arylcarboxylate ester of general formula 6 is added. In this modification of the Dieckmann reaction, the intermediate β-keto acid smoothly decarboxylates and a 1,2-diarylethanone of general formula 1 is produced.

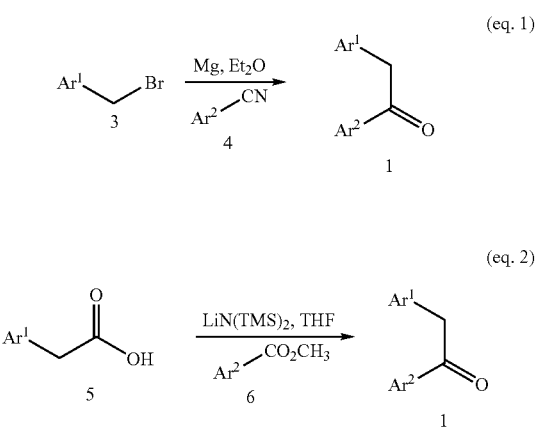

Reaction Scheme 3 illustrates two methods for the conversion of the 1,2-diarylethanone of general formula 1 into the 2-pyridones of general formula 2 where the position-3 substituent (X in formula 2, Scheme 1) is a cyano group. This transformation is conducted using one of the two methods illustrated in reaction Scheme 3, and the preferred method depends upon the selection of the substituent $R^3$ in the resulting 2-pyridone (2). When it is desired that the $R^3$ substituent be a hydrogen atom, then the 1,2-diarylethanone of general formula 1 is first converted to a vinylogous amide of general formula 7 by reaction with an N,N-methylformamide dimethylacetal as shown in equation 1. The condensation reaction is conducted using the DMF acetal as the reaction solvent at an elevated temperature, typically between room temperature and 150° C., and the vinylogous amide 7 is produced as a mixture of E and Z diastereoisomers. In the second step of this sequence, the vinylogous amide 7 is condensed with cyanoacetamide to afford the 2-pyridone of general formula 2 (X=CN). The reaction is usually conducted in a polar aprotic solvent such as DMF in the presence of a strong base such as an alkali metal hydride or alkoxide.

Equation 2 at the bottom of reaction Scheme 3 illustrates an alternative procedure for the preparation of 2-pyridones of general formula 2 which may afford a superior overall yield in cases where the $R^3$ substituent is chosen to be a group other than a hydrogen atom. In this sequence, the 1,2-diarylethanone 1 is first condensed with an ortho-ester of general formula 8 to afford vinylogous esters of general formula 9 as a mixture of E and Z diastereoisomers. The vinylogous esters of general formula 9 may then be condensed with cyanoacetamide as described above to afford 2-pyridones of general formula 2.

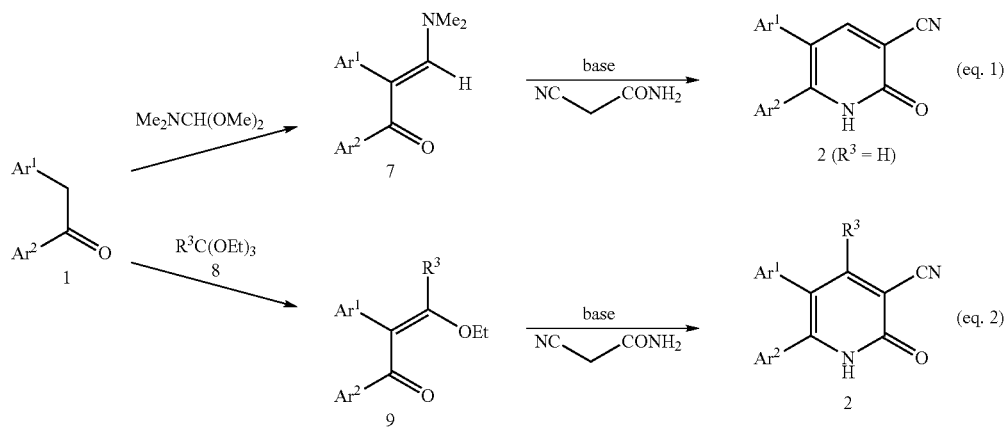

Several methods for the final stage of the synthesis of the novel compounds of general formula I are illustrated in reaction Schemes 4 through 11.

Reaction Scheme 4 illustrates a method for the conversion of compounds of general formula 2 to the title compounds of general formula I. In this sequence the 2-pyridone of general formula 2 is first chlorinated to afford a 2-chloropyridine derivative of general formula 10. The chlorination reaction can be accomplished using several chlorination reagents. For instance, treatment of 2 with oxalyl chloride in an inert solvent such as methylene chloride produces the 2-chloropyridine 10. This chlorination is typically conducted at temperatures between room temperature and the reflux temperature of the solvent being used for periods of 1-24 hours. Alternatively, heating the 2-pyridone 2 with phosphorus oxychloride in the absence of a solvent at a temperature between room temperature and 105° C. also affords the 2-chloropyridine of general formula 10. The resulting 2-chloropyridine (10) is then subjected to a nucleophilic aromatic substitution reaction using an amine of general formula 11 bearing the $R^4$ substituent and the 2-substituted pyridine of general formula 12 is produced. This reaction is conducted in a suitable aprotic solvent such as THF, toluene, DMF or a halocarbon solvent at temperatures between room temperature and the reflux temperature of the solvent. Acylation of amines of general structure 12 is often quite difficult due to the lack reactivity of the amino group at the 2-position. However, deprotonation of the 2-amino group prior to acylation can improve yields and allow for the use of mild reaction conditions (lower reaction temperatures for example). The deprotonation can be accomplished with a variety of bases such as NaH or MeMgBr at room temperatures or below. Treatment of the amine anion with an acylating agent of general formula 13 yields the desired amide 14. The amide may be isolated and purified or treated directly with additional base such as NaH to carry out the cyclization. Once the methylene adjacent to the carbonyl is deprotonated it can undergo intramolecular nucleophilic attack on the adjacent nitrile and the title compound of general formula I where $R^2$ is an amino group is produced 15. This process is carried out in a suitable aprotic solvent such as THF, toluene, DMF, halocarbon or a mixture thereof at a temperature suitable to prevent amide cleavage typically room temperature or below.

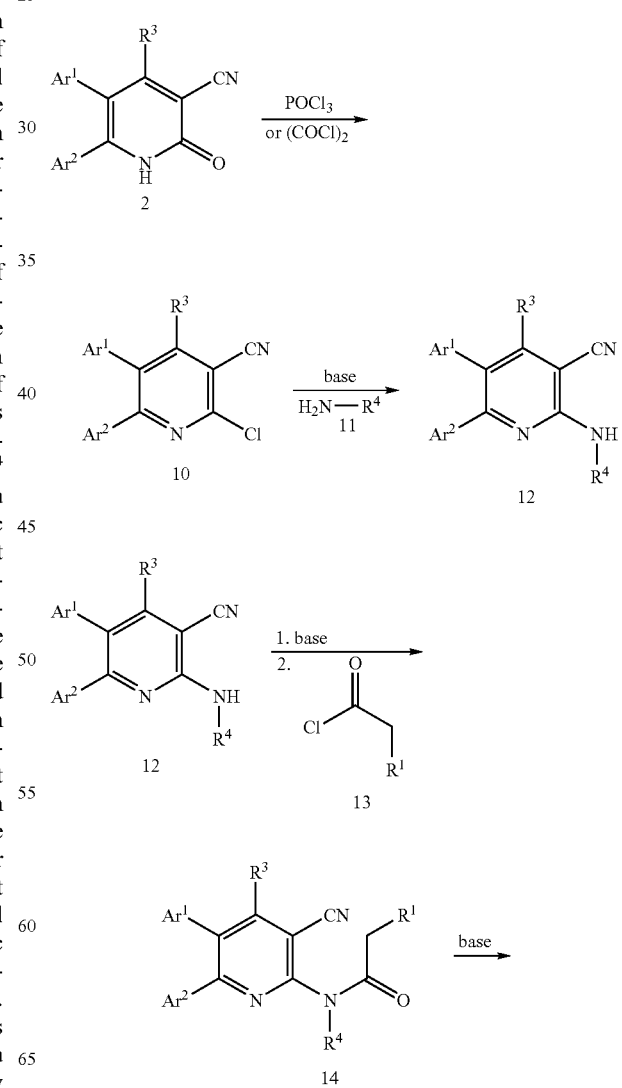

-continued

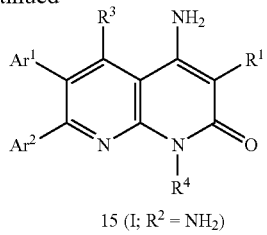

15 (I; $R^2 = NH_2$)

When the acylating agent 13 bears a suitable leaving group for $R^1$ such as chloride, nucleophilic displacement can be carried out with a variety of nucleophiles including but not limited to amines or sodium cyanide. These reactions are carried out in a suitable aprotic solvent such as THF or DNF. The reactions can be aided by the use of a phase transfer catalyst such as tetraethylammonium bromide or by generating a better leaving group by addition of KI to first displace the chloride when X happens to be chloride. If the reaction matrix is sufficiently basic the amide 14 may spontaneously cyclize to afford 15 or the intermediate 14 may be isolated and then subjected to base treatment as described previously for Scheme 4.

Scheme 5

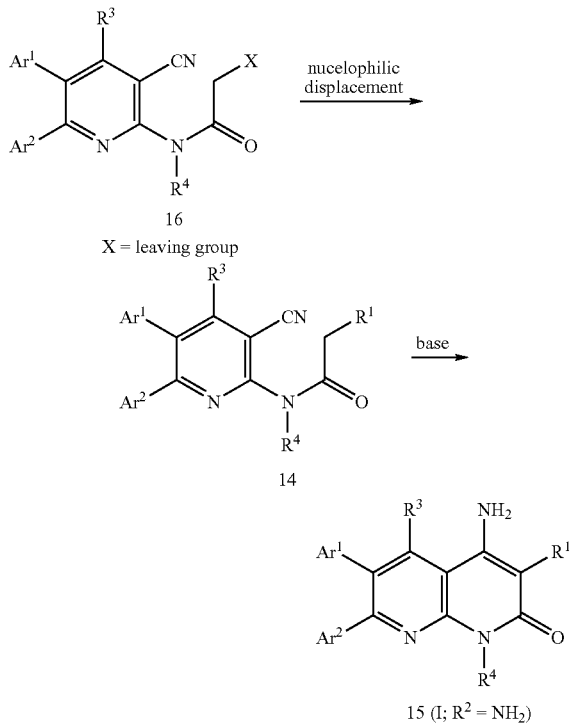

A novel alternative approach to generate substituted naphthyridinones of general formula 17 from 12 is shown in Scheme 6. To our knowledge this transformation has not previously been reported in the literature and greatly facilitates the preparation of the N-(3-acetyl-2-oxo-1,2-dihydro-1,8-naphthyridin-4-yl)acetamide core structure (e.g. 17). In the course of this one pot process the 2-aminopyridine is treated with greater than 3 equivalents of acetic anhydride either neat or with an appropriate solvent such as pyridine. A base such as DMAP is also employed sometimes but not always in conjunction with sodium acetate and the reaction is heated to between 50° C. and 150° C., but more preferably between 80°-110° C. The reaction conditions required will depend in part on the substituents $Ar^2$, $Ar^1$, $R^3$ and particularly $R^4$. Small $R^4$ groups such as methyl will require lower temperatures to affect acylation/cyclization. As $R^4$ becomes more sterically hindered higher temperatures and longer reaction times will be required to affect the same transformation. Typical reaction times of between 4 and 12 hours are common but times of greater than 12 hours are sometimes required. Those skilled in the art of organic synthesis will realize that this is a complex process as the normally expected product of an amine and these acylating conditions would be the acetamide product and not 17.

Scheme 6

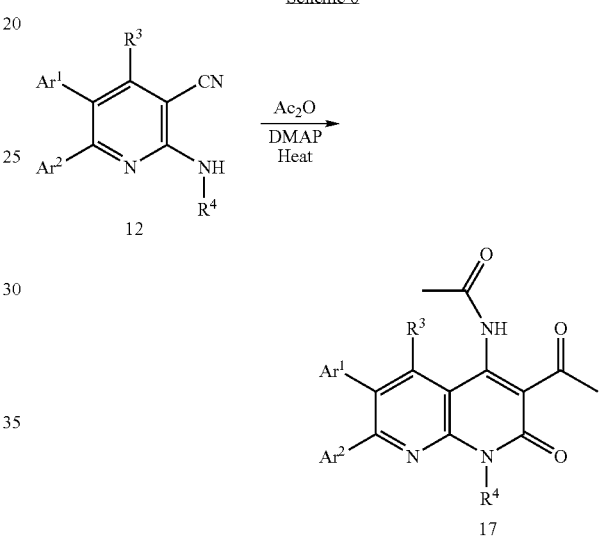

Scheme 7 depicts several alternative approaches to the preparation of novel compounds of general formula 17. Each of these approaches however requires at least two steps in contrast to one step as shown in Scheme 6. Additionally the reagents employed in Scheme 7 can be highly reactive, toxic, expensive, hard to make or have stability issues as compared to the inexpensive and relatively innocuous acetic anhydride. Diketene (18), 2,2,6-trimethyl-4H-1,3-dioxin-4-one (19), 5-acetyl-"Meldrums acid" (20), and acetoacetyl chloride (21) each provide a slightly different approach to get to the same key acetoacetamide intermediate 22. Clemens and Hyatt (J. Org. Chem. 1985, 50, 2431-2435; the references therein provide information regarding the use of each of the reagents 18-21) discuss the use of 19 which provides for a conveniently handled diketene substitute. Compound 19 may prove the most practical reagent to use as they claim it has the ability to acetoacetylate hindered and aromatic amines without the use of catalysts generating only volatile by-products. When 19 is heated to a temperature of greater than 100° C. it decomposes giving off acetone and acetylketene the active acetoacetylating species. In the presence of 12 intermediate 22 should be formed which in the presence of base undergoes cyclization to afford compounds of general formula 15 ($R^1$=acetyl). Exposure of 15 to acetic anhydride generates the desired compounds of general formula 17.

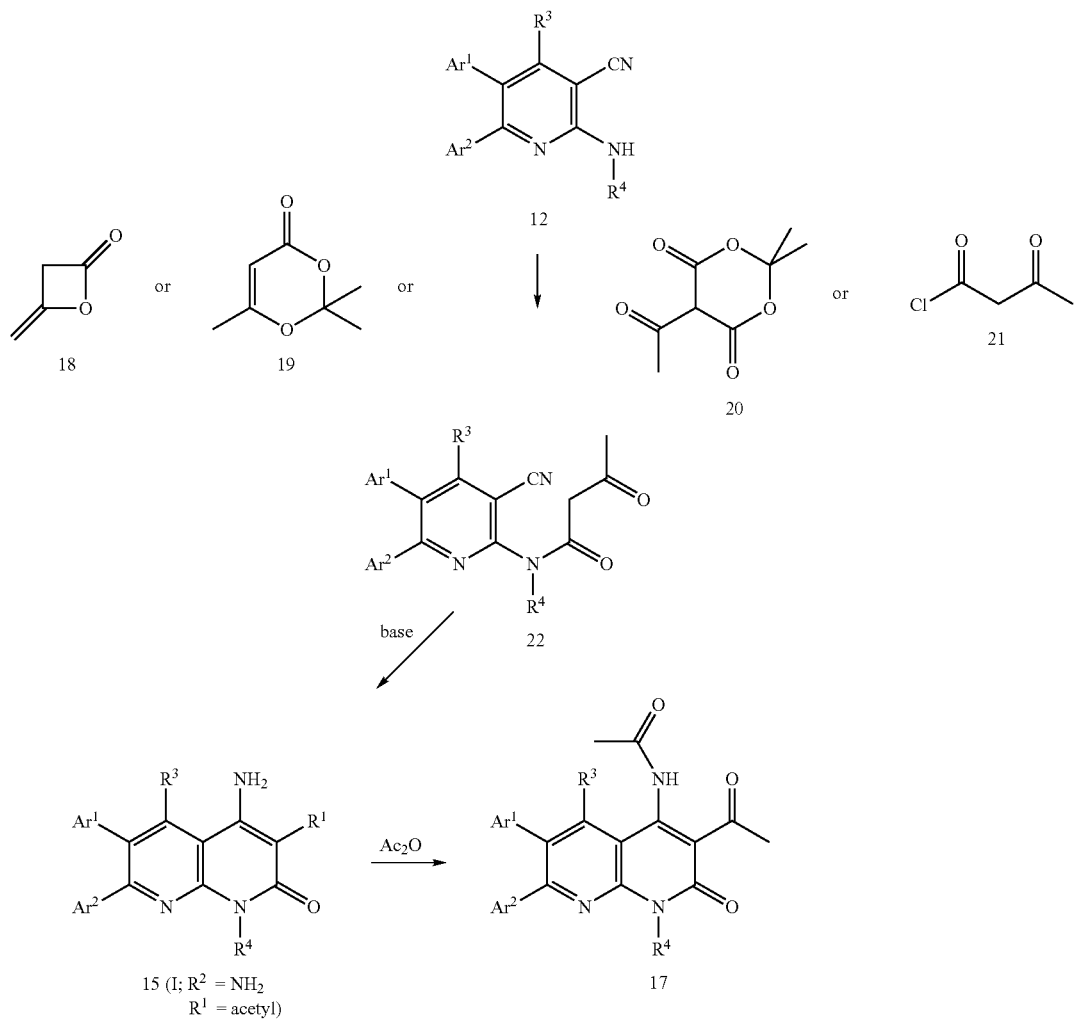

Scheme 8

In light of the chemistry depicted in Scheme 6 it was of interest to see how other anhydrides of general formula 23 would behave under similar conditions. In this case, compounds of general formula 24 were produced. For example when propionic anhydride is reacted with 12 using the conditions of Scheme 6, the 4-di-N-propionimide is formed. Treatment of the imide with methoxide allows for formation of the 4-N-propionamide.

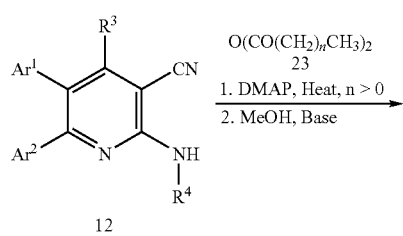

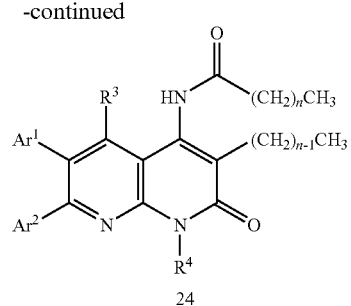

From the discussion above it is seen that when the position-3 substituent in compounds of general formula 2 is a cyano group, as illustrated in reaction Schemes 4 and 5, then the resulting substituent $R^2$ in the title compound of general formula I becomes a primary amino group ($R^2$=$NH_2$). Furthermore when $R^2$ bears an amide functionality ($R^2$=$NHCOR^c$), Schemes 6-8, the amide may be hydrolyzed back to a primary amine using standard methods such as acid hydrolysis with aqueous hydrochloric acid or trifluoroacetic acid at elevated temperature for example. The primary amino group of compounds of general formula 15 derived using these procedures may be converted to a variety of alternative functional groups that are within the scope of the definition of the substituent $R^2$ defined above using methods known in the art of organic synthesis. For instance the amino group in compounds of general formula 15 may be converted to amides, carbamates, or ureas (25), and sulfonamides or sulfonylureas (26) by reaction with the appropriate acylating (e.g. $R^cCOCl$) or sulfonylating (e.g. $R^cSO_2Cl$) reagents respectively, as outlined in reaction Scheme 9. When a compound of general formula 15 is reacted with an excess of the acylating or sulfonylating reagents shown in reaction Scheme 6, the amino group may be acylated or sulfonylated twice resulting in the carboximide (27) or sulfonimide (28) derivatives as shown.

the presence of a base affords the mono- or di-alkylated derivatives of general formula 30 as shown in equation 1 of reaction Scheme 10. It is also recognized that it is possible to employ the compounds of general formula 15 in a sequence that combines the acylation or sulfonylation reactions shown in reaction Scheme 9 with the alkylation reaction illustrated in reaction Scheme 10. For instance when a compound of general formula 25 is subjected to the N-alkylation reaction, an N-alkylcarboxamide of general formula 32 is the product as shown in equation 2 of reaction Scheme 10. Similarly, the alkylation of a compound of general formula 26 affords an N-alkylsulfonamide of general formula 33 (eq. 3). The compounds of general formulae 25 and 26 are also useful substrates for a Mitsunobu reaction sequence. Thus, the reaction of these compounds (25 & 26) with an alcohol of general

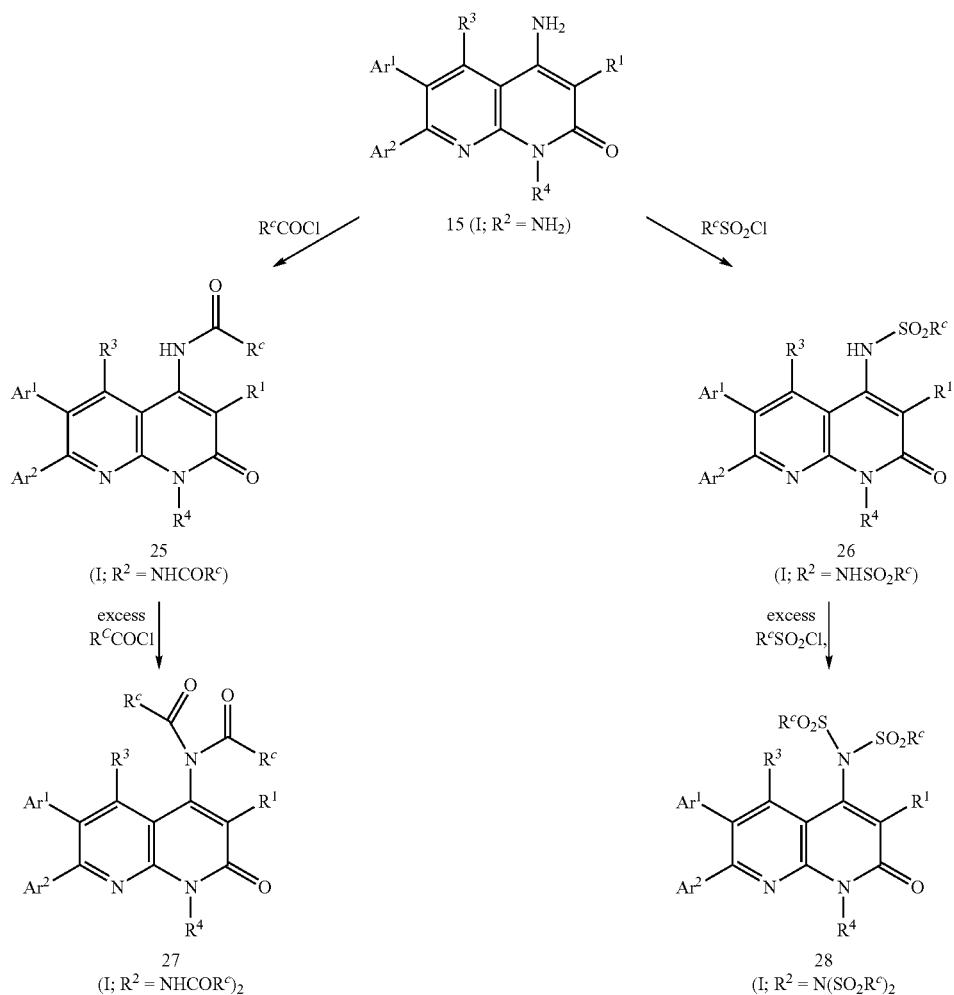

The primary amino group in compounds of general formula 15 may also be elaborated into other groups that are within the scope of the definition of the substituent $R^2$ using alkylation reactions, reductive aminations, Michael additions, etc. For example, alkylation of compounds of general formula 15 using an alkylating agent of general formula 29 in formula 31 in the presence of triphenylphosphine and diethyl or diisopropylazodicarboxylate also affords the N-alkylation products 32 and 33.

Finally, when a compound of general formula 25 or 26 contains a suitable leaving group or a hydroxyl group in its $R^c$ substituent it is possible to conduct either an intramolecular alkylation or intramolecular Mitsunobu reaction using the conditions described in equation 2 and 3 of reaction Scheme 10. In these cases the alkylating reagent 29 or the alcohol 31 are omitted from the reaction mixtures and a heterocyclic compound of general formula 32 or 33 wherein the substituents $R^5$ and $R^c$ are closed to form a ring is the product.

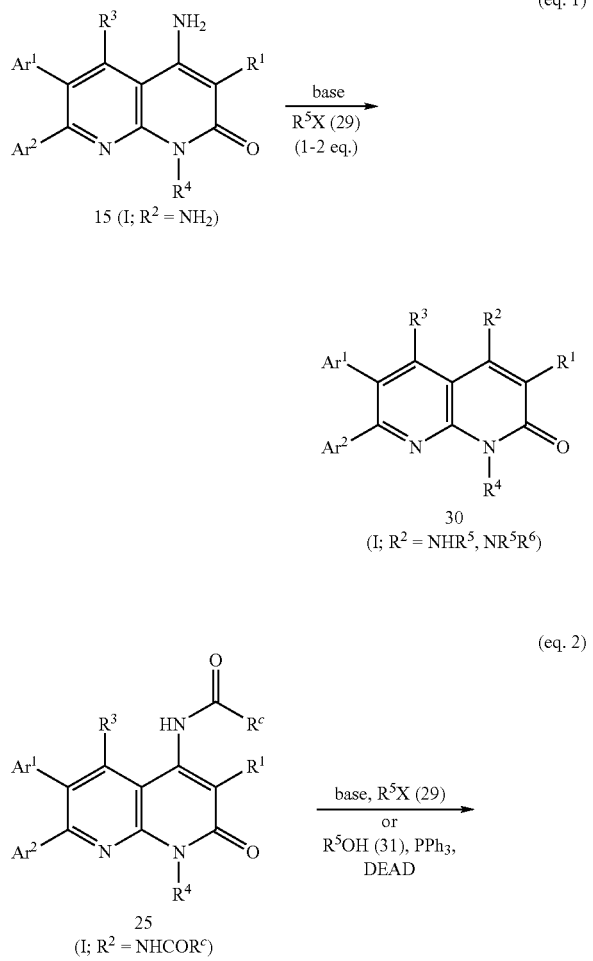
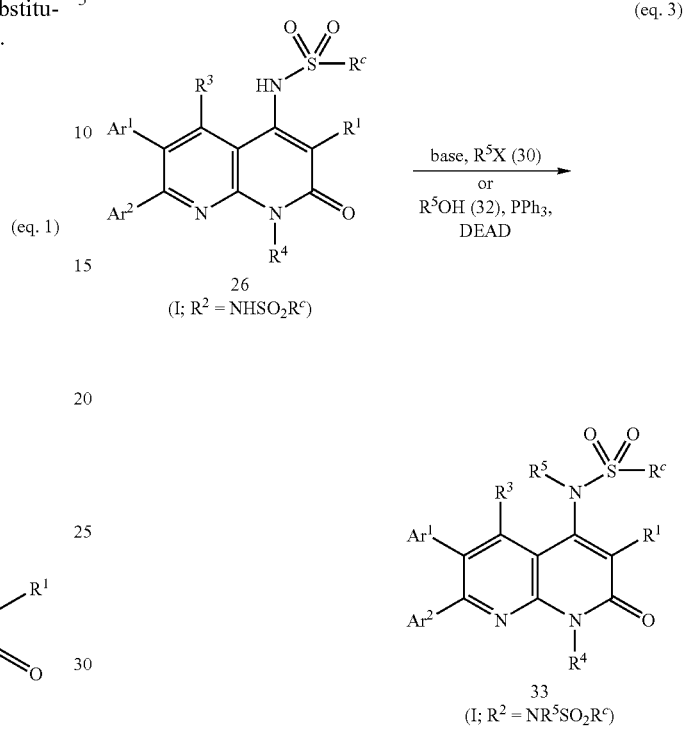

In addition to the methods illustrated in reaction Schemes 9 and 10, the primary amino group of compounds of general formula 15 may be further modified using a variety of methods known in organic synthesis. The amino group of compounds of general formula 15 may be N-arylated using methods such as the copper-mediated coupling of arylboronic acids (Chan, D. M. T.; Monaco, K. L.; Wang, R.-P.; Winters, M. P. *Tetrahedron Lett.* 1998, 39, 2933-2936) or the palladium-mediated coupling of aryl halides (see Muci, A. R. Buchwald, S. L. *Topics in Current Chemistry* 2002, 219 (Cross-Coupling reactions), 131-209). When the amino group of compounds of general formula 15 is modified using one of these methods, a compound of general formula 34 wherein $R^5$ is an aromatic or heteroaromatic ring is produced as shown at the top of reaction Scheme 11. Compounds of general formula 15 may also be diazotized to afford a diazonium salt of general formula 35. Diazonium salts such as 35 may then be converted to additional examples of compounds of general formula I wherein $R^2$ is defined above as shown at the bottom of reaction Scheme 11. For example, the diazonium salts (35) may be utilized in Sandmeyer reactions or in various palladium(0)-catalyzed cross coupling reactions such as Suzuki cross-couplings, Heck reactions, Stille reactions and palladium-mediated alkoxy- or aminocarbonylation reactions.

Scheme 11

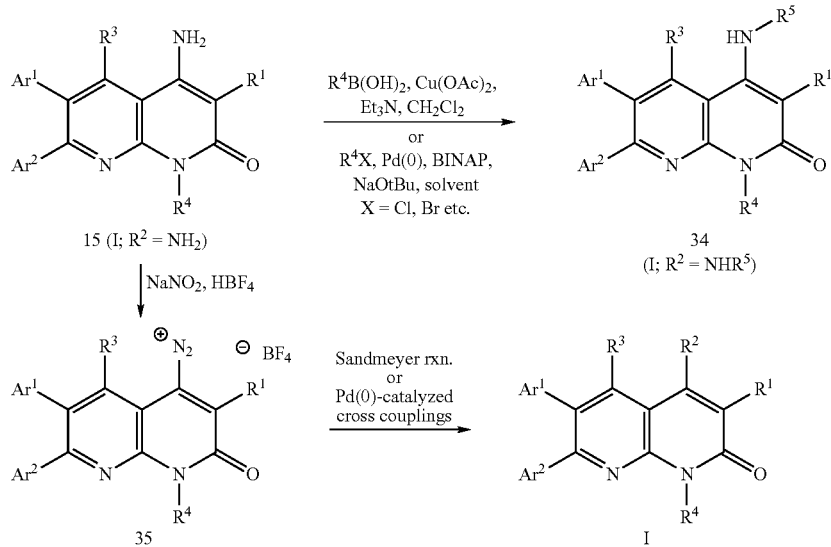

EXAMPLE 1

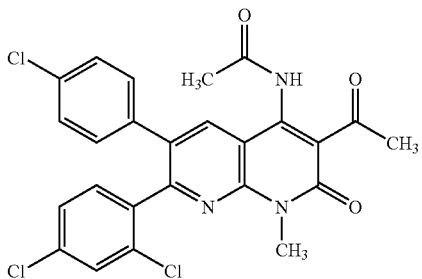

N-[3-Acetyl-6-(4-chlorophenyl)-7-(2,4-dichlorophenyl)-1-methyl-2-oxo-1,2-dihydro-1,8-naphthyridin-4-yl]acetamide Step A: 3-Dimethylamino-1-(2,4-dichlorophenyl)-2-(4-chlorophenyl)prop-2-en-1-one A solution of 4-chlorobenzyl 2,4-dichlorophenyl ketone (4.5 g, 14.4 mmol) and dimethyl-formamide dimethylacetal (7.7 mL, 58 mmol) in DMF (60 mL) was heated at 75° C. for 20 h. The volatiles were removed in vacuo to provide the crude product which was used directly in the next step. HPLC/MS: 354 (M+1), 356 (M+3); $R_t$=3.47 min.

Step B: 6-(2,4-Dichlorophenyl)-5-(4-chlorophenyl)-2-oxo-1,2-dihydropyridine-3-nitrile A solution of 3-dimethylamino-1-(2,4-dichlorophenyl)-2-(4-chlorophenyl)prop-2-en-1-one (14.4 mmol assumed) from Step A, cyanoacetamide (1.33 g, 15.8 mmol), and methanol (1.3 mL, 32 mmol) in DMF (35 mL) was added drop wise to a suspension of sodium hydride (60% in mineral oil) (1.45 g, 36 mmol) in DMF (16 mL) at rt. After the slow addition was complete, the reaction was heated to 95° C. for 2.5 h. Most of the DMF was then removed in vacuo before the reaction was diluted with aqueous 18% citric acid solution. The mixture was extracted twice with methylene chloride and the organic layers were washed with a portion of brine. The combined organic layers were dried over anhydrous sodium sulfate and concentrated in vacuo. The solid residue was triturated with ether, filtered, and air dried to afford the product. HPLC/MS: 375 (M+1), 377 (M+3); $R_t$=3.47 min.

Step C: 2-chloro-6-(2,4-dichlorophenyl)-5-(4-chlorophenyl)pyridine-3-carbonitrile To 6-(2,4-Dichlorophenyl)-5-(4-chlorophenyl)-2-oxo-1,2-dihydropyridine-3-nitrile (40.75g) was added POCl$_3$ (20 mL). The reaction was heated to 100° C. for 13 hours. After cooling to room temperature the excess POCl$_3$ was removed in vacuo before the residue was dissolved in CH$_2$Cl$_2$ and washed with saturated aqueous NaHCO$_3$ solution. The solution was concentrated and purified via flash chromatography on silica gel with a gradient elution of 30% to 100% CH$_2$Cl$_2$ in hexane affording the title compound. HPLC/MS: 392.9 (M+1), 394.9 (M+3); $R_t$=4.45 min.

Step D: 6-(2,4-dichlorophenyl)-5-(4-chlorophenyl)-2-(methylamino)pyridine-3-carbonitrile To 2-chloro-6-(2,4-dichlorophenyl)-5-(4-chlorophenyl)pyridine-3-carbonitrile (2.03 g) in THF (14 mL) was added H$_2$NCH$_3$ (13 mL, 2 M solution in THF). The reaction was heated to 67° C. in a closed vessel for 9 hours before concentrating. The product was dissolved in EtOAc and washed with saturated aqueous NaHCO$_3$ solution. The solution was concentrated and purified via flash chromatography on silica gel with a gradient elution of 0% to 10% EtOAc in hexane affording the title compound. HPLC/MS: 387.8(M+1), 389.8 (M+3); $R_t$=4.26 min.

Step E: N-[3-Acetyl-6-(4-chlorophenyl)-7-(2,4-dichlorophenyl)-1-methyl-2-oxo-1,2-dihydro-1,8-naphthyridin-4-yl]acetamide To 355 mg of the product of step D in pyridine (7.2 mL) was added DMAP (135 mg) and acetic anhydride (2.67 mL). The reaction was heated to 90° C. for 3 hours 45 minutes before concentrating and dissolving the residue in CH$_2$Cl$_2$. The solution was washed with 1 M aqueous HCl and then saturated aqueous NaHCO₃ solution before drying with Na₂SO₄. The concentrated residue was purified by flash chromatography on silica gel with a gradient elution of 0-20% EtOAc in CH₂Cl₂ affording the title compound. HPLC/MS: 513.9 (M+1), 515.9 (M+3); $R_t$=3.87 ml.

EXAMPLE 2

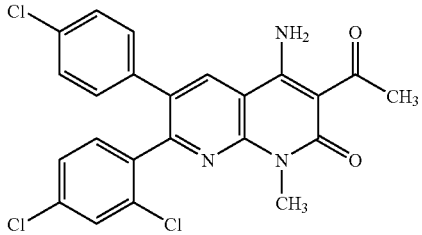

3-Acetyl-4-amino-6-(4-chlorophenyl)-7-(2,4-dichlorophenyl)-1-methyl-1,8-naphthyridin-2(1H)-one To 16 mg of the product of Example 1 in 1,4-dioxane (1 mL) was added 0.5 mL of 1 M aqueous HCl solution. The reaction stirred at 50° C. for 5 hours. LC/MS indicated little product forming and an additional 0.2 mL of concentrated HCl solution was added. The temperature was increased to 90° C. for 4.5 hours at which point the reaction was cooled to room temperature and diluted with EtOAc. The solution was washed with saturated aqueous NaHCO₃ solution before drying with Na₂SO₄ and concentrating. The residue was purified by preparative TLC (silica gel) eluted with 20% EtOAc in CH₂Cl₂ affording the title compound. HPLC/MS: 471.9 (M+1), 473.9 (M+3); $R_t$=4.32 min.

EXAMPLE 3

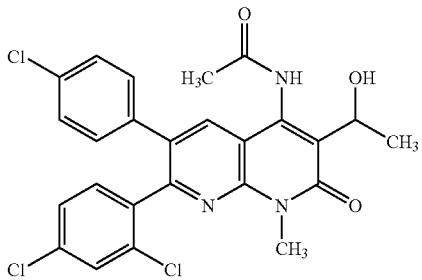

N-[6-(4-Chlorophenyl)-7-(2,4-dichlorophenyl)-3-(1-hydroxyethyl)-1-methyl-2-oxo-1,2-dihydro-1,8-naphthyridin-4-yl]acetamide The product of Example 1 (65 mg), THF (3 mL), MeOH (0.33 mL) and NaBH₄ (9.6 mg) were combined at room temperature. After 7 minutes the reaction was concentrated and then dissolved in EtOAc before washing with water and drying (Na₂SO₄). The concentrated residue was purified by preparative TLC (silica gel) eluted with EtOAc affording the title compound. HPLC/MS: 515.9 (M+1), 517.9 (M+3); $R_t$=3.68 min.

EXAMPLE 4

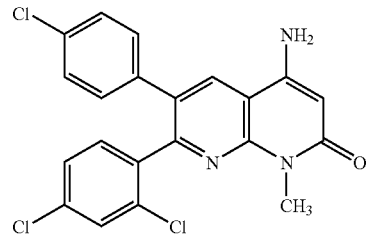

4-Amino-6-(4-chlorophenyl)-7-(2,4-dichlorophenyl)-1-methyl-1,8-naphthyridin-2(1H)-one The product of Example 3 (21 mg) was combined with 2.8 mL of 1,4-dioxane and 1 mL 1M aqueous HCl. After 15 hours at room temperature the reaction was diluted with EtOAc and washed with water followed by saturated aqueous NaHCO₃ solution before drying (Na₂SO₄). The concentrated residue was purified by preparative TLC (silica gel) eluted with EtOAc affording the title compound. HPLC/MS: 430.0 (M+1), 432.0 (M+3); $R_t$=3.77 min.

EXAMPLE 5

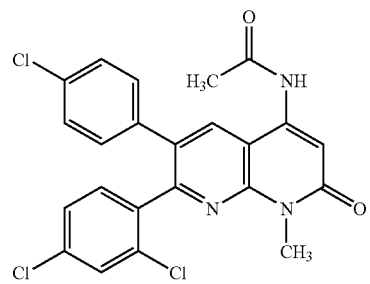

N-[6-(4-Chlorophenyl)-7-(2,4-dichlorophenyl)-1-methyl-2-oxo-1,2-dihydro-1,8-naphthyridin-4-yl]acetamide The product of Example 4 (18 mg) was combined with pyridine (2 mL), acetic anhydride (0.2 mL), and DMAP (5 mg). The reaction was heated to 85° C. for 1 hr at which point LC/MS indicated significant imide formation. The reaction was concentrated and redissolved in 1,4-dioxane before adding aqueous 1 M NaOH (1 mL). After 15 hours at room temperature the reaction was diluted with EtOAc and washed with brine before drying (Na₂SO₄). The concentrated residue was purified by preparative TLC (silica gel) eluted with EtOAc affording the title compound. HPLC/MS: 471.9 (M+1), 473.9 (M+3); $R_t$=3.79 inn.

EXAMPLE 6

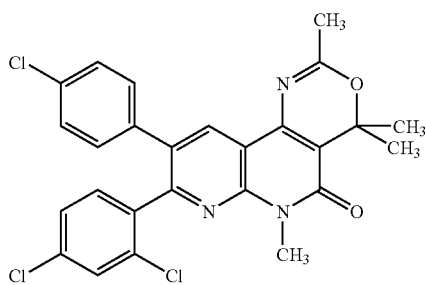

9-(4-Chlorophenyl)-8-(2,4-dichlorophenyl)-2,4,4,6-tetramethyl-4,6-dihydro-5H-[1,3]oxazino[5,4-c]-1,8-naphthyridin-5-one To the product of Example 1 (59.5 mg) in THF (2 mL) at 0° C. was added 0.52 mL MeMgBr solution (1.4 M, 75% toluene/25% THF). After 10 min the reaction was quenched with saturated aqueous NH$_4$Cl and then diluted with EtOAc. The solution was washed with 10% aqueous NaHSO$_4$ followed by aqueous NaHCO$_3$/NaOH (4:1) before drying (Na$_2$SO$_4$). The concentrated residue was purified by preparative TLC (silica gel) eluted with 15% EtOAc in hexane affording the title compound. HPLC/MS: 512.0 (M+1), 514.0 (M+3); $R_t$=5.14 min.

EXAMPLE 7

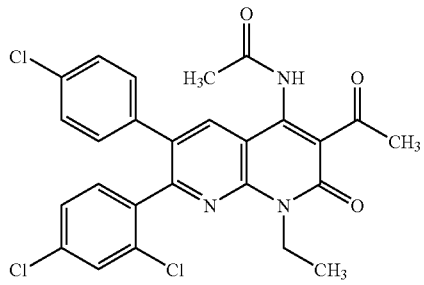

N-[3-Acetyl-6-(4-chlorophenyl)-7-(2,4-dichlorophenyl)-1-ethyl-2-oxo-1,2-dihydro-1,8-naphthyridin-4-yl]acetamide The title compound was prepared using a similar procedure to that described in Example 1 but substituting 6-(2-chlorophenyl)-5-(4-chlorophenyl)-2-ethylamino)pyridine-3-carbonitrile (0.19 g), acetic anhydride (0.89 mL), DMAP (69.2 mg) and pyridine (4 mL). The reaction was heated at 90° C. for 4 hours and 100° C. for 3.5 hours. Flash chromatography on silica gel gradient eluted with 25-60% EtOAc in hexane afforded the title compound. HPLC/MS: 527.9 (M+1), 529.9 (M+3); $R_t$=4.19 min.

EXAMPLE 8

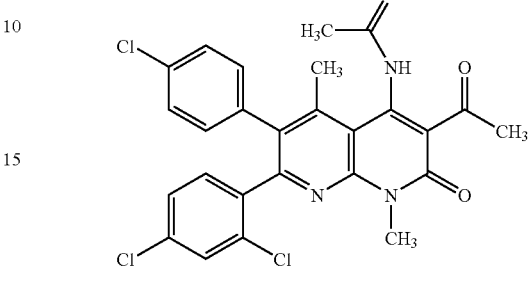

N-[3-Acetyl-6-(4-chlorophenyl)-7-(2,4-dichlorophenyl)-1,5-dimethyl-2-oxo-1,2-dihydro-1,8-naphthyridin-4-yl]acetamide The title compound was prepared using a similar procedure to that described in Example 1 but substituting 6-(2-chlorophenyl)-5-(4-chlorophenyl)-4-methyl-2-methylamino)pyridine-3-carbonitrile (0.13 g), acetic anhydride (1.1 g), DMAP (50 mg) and pyridine (2.6 mL). The reaction was heated at 90° C. for 6 hours. Purification was by preparative TLC (silica gel) eluted with 20% EtOAc in CH$_2$Cl$_2$ followed by another preparative TLC (silica gel) eluted with 50% EtOAc in hexane afforded the title compound. HPLC/MS: 527.9 (M+1), 529.9 (M+3); $R_t$=3.90 min.

EXAMPLE 9

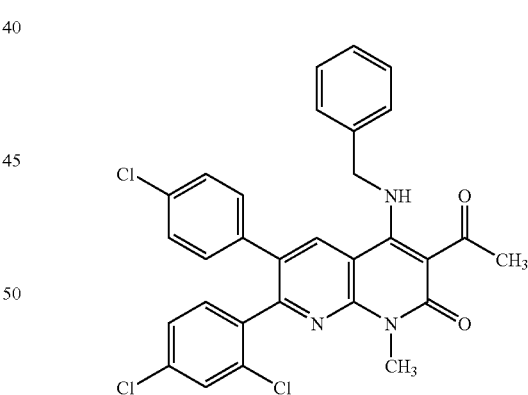

3-Acetyl-4-(benzylamino)-6-(4-chlorophenyl)-7-(2,4-dichlorophenyl)-1-methyl-1,8-naphthyridin-2(1H)-one A solution of the product from Example 2 (50 mg), potassium carbonate (14 mg) and benzyl bromide (12 μL) in THF (2 mL) was stirred overnight. No progress of the reaction was observed. The reaction mixture was cooled to 0° C., followed by addition of sodium hydride (60% in mineral oil) (4 mg). The reaction was stirred for 10 min and benzyl bromide (12 μL) was added. The suspension was allowed to come to room temperature and stirred overnight. The reaction was quenched with water and extracted twice with ethyl acetate. The organic layer was washed with brine, dried (MgSO₄), filtered and concentrated in vacuo. Purification on a preparative silica TLC plate eluted with 45% ethyl acetate in hexane afforded the title compound. HPLC/MS: 561.9 (M+1), 563.9 (M+3); $R_t$=5.09 min.

EXAMPLE 10

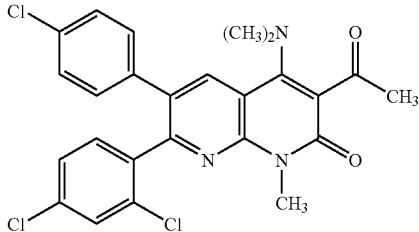

3-Acetyl-6-(4-chlorophenyl)-7-(2,4-dichlorophenyl)4 (dimethylamino)-1-methyl-1,8-naphthyridin-2(1H)-one A solution of the product from Example 2 (60 mg) in THF (2 mL) was cooled to 0° C. and treated with sodium hydride (60% in mineral oil) (5 mg). The suspension was stirred for 10 min were upon methyl iodine (15 uL) was added. The reaction was allowed to warm to room temperature and was stirred for 7 hours. The reaction mixture was quenched with water and extracted twice with methylene chloride. The organic layer was dried (MgSO₄), filtered and concentrated in vacuo. Purification on a preparative silica TLC plate eluted with 20% ethyl acetate in hexane afforded the title compound. HPLC/MS: 500.0 (M+1), 502.0 (M+3); $R_t$=4.67 min.

EXAMPLE 11

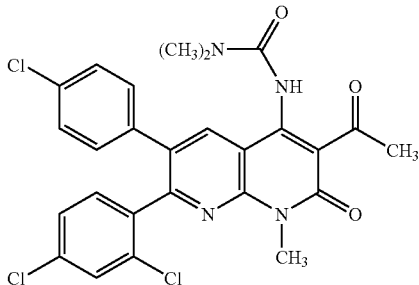

N'-[3-Acetyl-6-(4-chlorophenyl)-7-(2,4-dichlorophenyl)-1-methyl-2-oxo-1,2-dihydro-1,8-naphthyridin-4-yl]-N,N-dimethylurea A solution of the product from Example 2 (70 mg) in THF (1 mL), under nitrogen, was cooled to 0° C. and treated with sodium hydride (60% in mineral oil) (7 mg). The suspension was stirred for 10 min were upon dimethylcarbamyl chloride (15 uL) was added. The reaction was allowed to warm to room temperature and was stirred overnight. The reaction mixture was quenched with water and extracted twice with ethyl acetate. The organic layer was dried (MgSO₄), filtered and concentrated in vacuo. Purification on a preparative silica TLC plate eluted with 50% EtOAc in hexane afforded the title compound. HPLC/MS: 543.0 (M+1), 545.0 (M+3); $R_t$=4.27 min.

EXAMPLE 12

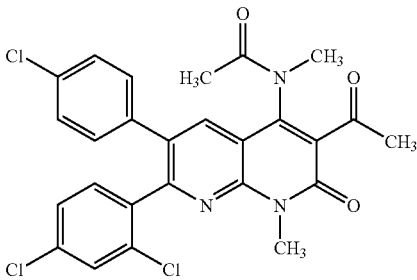

N-[3-acetyl-6-(4-chlorophenyl)-7-(2,4-dichlorophenyl)-1-methyl-2-oxo-1,2-dihydro-1,8-naphthyridin-4-yl]-N-methylacetamide A solution of the product from Example 2 (60 mg) in THF (1 mL), under nitrogen, was treated with iodomethane (73 uL) and Cs₂CO₃ (58 mg). The suspension was stirred overnight. The reaction mixture was quenched with water and extracted with ethyl acetate. The organic layer was dried (MgSO₄), filtered and concentrated in vacuo. Purification on a preparative silica TLC plate eluted with 25% EtOAc in hexane afforded the title compound. HPLC/MS: 528.1 (M+1), 530.1 (M+3); $R_t$=4.08 min.

EXAMPLE 13

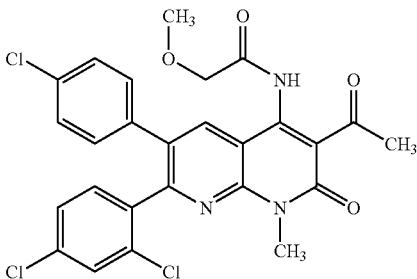

N-[3-acetyl-6-(4-chlorophenyl)-7-(2,4-dichlorophenyl)-1-methyl-2-oxo-1,2-dihydro-1,8-naphthyridin-4-yl]-2-methoxyacetamide A solution of the product from Example 2 (100 mg) in THF (3 mL), under nitrogen, was treated with sodium hydride (60% in mineral oil) (10 mg). The suspension was stirred for 5 min were upon methoxyacetyl chloride (40 uL) was added. The reaction was allowed to warm to room temperature and was stirred 30 min. The reaction mixture was quenched with aqueous NaHCO₃ (saturated) and extracted with ethyl acetate. The organic layer was dried (MgSO₄), filtered and concentrated in vacuo. Purification by flash chromatography on silica eluted with 0-30% EtOAc in hexane afforded the title compound. HPLC/MS: 543.8 (M+1), 545.8 (M+3); R$_t$=4.19 min.

Starting with the product of Step C Example 1 and treating with the appropriate amine the following examples were prepared using similar procedures described in reaction Schemes 1 to 11 and in the preceding examples.

EXAMPLE 14-EXAMPLE 25

| | Name | HPLC/MS m/z (M + 1) m/z (M + 3) R$_t$ (min) | |
|---|---|---|---|
| EXAMPLE 14 | N-[3-acetyl-1-benzyl-6-(4-chlorophenyl)-7-(2,4-dichlorophenyl)-2-oxo-1,2-dihydro-1,8-naphthyridin-4-yl]acetamide | 589.9 591.9 4.53 | 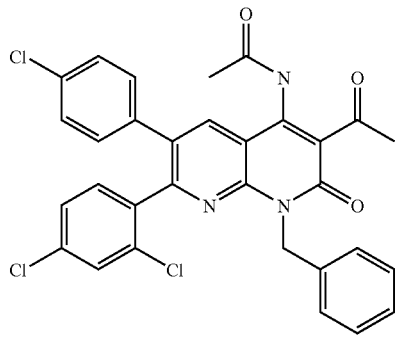 |
| EXAMPLE 15 | N-[3-acetyl-6-(4-chlorophenyl)-1-(cyclopropylmethyl)-7-(2,4-dichlorophenyl)-2-oxo-1,2-dihydro-1,8-naphthyridin-4-yl]acetamide | 554.0 556.0 4.43 | 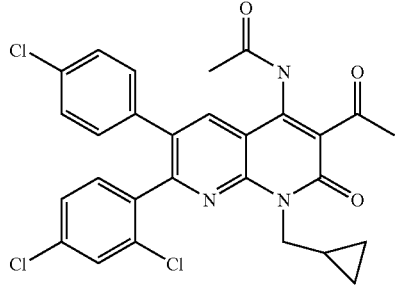 |
| EXAMPLE 16 | N-[3-acetyl-1-butyl-6-(4-chlorophenyl)-7-(2,4-dichlorophenyl)-2-oxo-1,2-dihydro-1,8-naphthyridin-4-yl]acetamide | 555.9 557.9 4.61 | 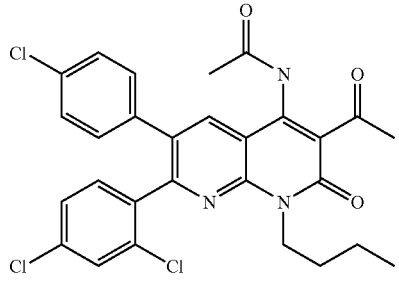 |
| EXAMPLE 17 | N-[3-acetyl-6-(4-chlorophenyl)-7-(2,4-dichlorophenyl)-1-isobutyl-2-oxo-1,2-dihydro-1,8-naphthyridin-4-yl]acetamide | 556.1 558.1 4.56 | 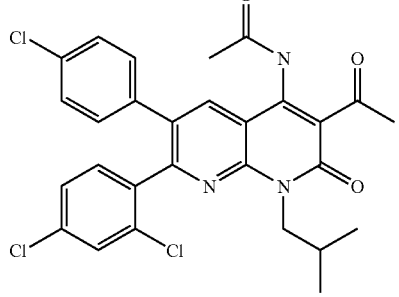 |

-continued

| | Name | HPLC/MS m/z (M + 1) m/z (M + 3) R_t (min) | |
|---|---|---|---|
| EXAMPLE 18 | N-[3-acetyl-6-(4-chlorophenyl)-7-(2,4-dichlorophenyl)-1-(2-methoxyethyl)-2-oxo-1,2-dihydro-1,8-naphthyridin-4-yl]acetamide | 557.9 559.9 3.95 | |
| EXAMPLE 19 | N-[3-acetyl-6-(4-chlorophenyl)-7-(2,4-dichlorophenyl)-2-oxo-1-(tetrahydrofuran-2-ylmethyl)-1,2-dihydro-1,8-naphthyridin-4-yl]acetamide | 584.1 586.1 4.19 | |
| EXAMPLE 20 | 2-{[3-acetyl-4-(acetylamino)-6-(4-chlorophenyl)-7-(2,4-dichlorophenyl)-2-oxo-1,8-naphthyridin-1(2H)-yl]methyl}pyridinium trifluoroacetate | 591.0 593.0 2.99 | |
| EXAMPLE 21 | 3-{[3-acetyl-4-(acetylamino)-6-(4-chlorophenyl)-7-(2,4-dichlorophenyl)-2-oxo-1,8-naphthyridin-1(2H)-yl]methyl}pyridinium trifluoroacetate | 591.0 593.0 2.83 | |

-continued

| | Name | HPLC/MS m/z (M + 1) m/z (M + 3) R$_t$ (min) | |
|---|---|---|---|
| EXAMPLE 22 | 2-[3-acetyl-4-(acetylamino)-6-(4-chlorophenyl)-7-(2,4-dichlorophenyl)-2-oxo-1,8-naphthyridin-1(2H)-yl]ethyl acetate | 586.0 588.0 4.31 | |
| EXAMPLE 23 | N-[3-acetyl-6-(4-chlorophenyl)-7-(2,4-dichlorophenyl)-1-(2,4-dimethoxybenzyl)-2-oxo-1,2-dihydro-1,8-naphthyridin-4-yl]acetamide | 650.0 652.0 4.35 | |
| EXAMPLE 24 | 4-{[3-acetyl-4-(acetylamino)-6-(4-chlorophenyl)-7-(2,4-dichlorophenyl)-2-oxo-1,8-naphthyridin-1(2H)-yl]methyl}pyridinium trifluoroacetate | 591.0 593.0 3.55 | |
| EXAMPLE 25 | N-[3-acetyl-6-(4-chlorophenyl)-7-(2,4-dichlorophenyl)-2-oxo-1-propyl-1,2-dihydro-1,8-naphthyridin-4-yl]acetamide | 542.0 544.0 4.37 | |

EXAMPLE 26

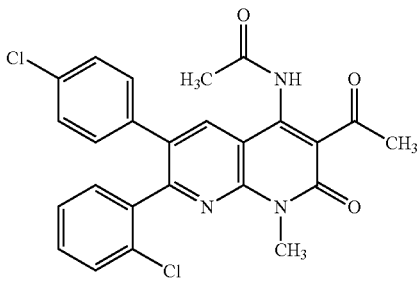

N-[3-Acetyl-7-(2-chlorophenyl)-6-(4-chlorophenyl)-1-methyl-2-oxo-1,2-dihydro-1,8-naphthyridin-4-yl]acetamide Step A: 1-(2-Chlorophenyl)-2-(4-chlorophenyl)-3-(dimethylamino)prop-2-en-1-one To 13.2 g of 1-(2-chlorophenyl)-2-(4-chlorophenyl)ethanone in 100 mL of DMF was added 23.8 g of N,N-dimethylformamide dimethyl acetal. The mixture was stirred at 75° C. for 16 hours. The solution was then concentrated and used without further purification in the next step.

Step B: 6-(2-Chlorophenyl)-5-(4-chlorophenyl)-2-oxo-1,2-dihydropyridine-3-carbonitrile A solution of the crude product from step A dissolved in 80 mL of DMF containing 4.4 mL methanol and 4.61 g cyanoacetamide was transferred by cannula into a flask containing a suspension of NaH (4.98 g, 60% dispersion in mineral oil, freed of excess oil by washing with hexane just prior to use) in DMF (40 mL). The solution was heated to 95° C. for 2.5 hours then concentrated. The residue was dissolved in ethyl acetate, washed twice with 10% aqueous NaHSO$_4$, and twice with water before concentrating to a solid. The solid was suspended in warm ethanol and then cooled, and the title compound was subsequently isolated by filtration and dried in vacuo.

Step C: 2-chloro-6-(2-chlorophenyl)-5-(4-chlorophenyl)pyridine-3-carbonitrile

To the product of Step B (1.5 g) was added POCl$_3$ (5 mL). The reaction was heated to 100° C. for 17 hours. After cooling to room temperature the excess POCl$_3$ was removed in vacuo before the residue was dissolved in EtOAc and washed with saturated aqueous NaHCO$_3$ solution. The solution was concentrated and purified via flash chromatography on silica gel eluted with 10% EtOAc in hexane affording the title compound. HPLC/MS: 358.9 (M+1), 360.9 (M+3); R$_t$=4.07 min.

Step D: 6-(2-chlorophenyl)-5-(4-chlorophenyl)-2-(methylamino)pyridine-3-carbonitrile To the product of Step C (300 mg) was added H$_2$NCH$_3$ (3.34 mL, 2 M solution in THF). The reaction stirred at room temperature overnight before concentrating. The product was dissolved in EtOAc and washed with saturated aqueous NaHCO$_3$ solution. The solution was concentrated and purified via flash chromatography on silica gel with a gradient elution of 0% to 20% EtOAc in hexane affording the title compound. HPLC/MS: 353.9 (M+1), 355.9 (M+3); R$_t$=4.21 min.

Step E: N-[3-Acetyl-7-(2-chlorophenyl)-6-(4-chlorophenyl)-1-methyl-2-oxo-1,2-dihydro-1,8-naphthyridin-4-yl]acetamide To the product of Step D (252 mg) in pyridine (4 mL) was added DMAP (104 mg) and acetic anhydride (1.34 mL). The reaction was heated to 90° C. for 5 hours before concentrating and dissolving the residue in CHCl$_3$. The solution was washed with 1.3 M aqueous HCl and then saturated aqueous NaHCO$_3$ solution. The concentrated residue was purified by flash chromatography on silica gel with a gradient elution of 10-70% EtOAc in hexane and then by preparative TLC (silica gel) eluted with 60% EtOAc in hexane affording the title compound. HPLC/MS: 480.0 (M+1), 482.0 (M+3); R$_t$=3.57 min.

EXAMPLE 27

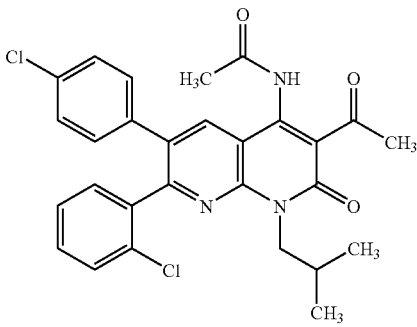

N-[3-Acetyl-7-(2-chlorophenyl)-6-(4-chlorophenyl)-1-isobutyl-2-oxo-1,2-dihydro-1,8-naphthyridin-4-yl]acetamide Step A: 6-(2-chlorophenyl)-5-(4-chlorophenyl)-2-(isobutylamino)pyridine-3-carbonitrile To the product of Step C EXAMPLE 26 (300 mg) in THF (3.3 mL) was added isobutylamine (0.83 mL). The reaction stirred at room temperature overnight at which point LC/MS indicated incomplete reaction. The temperature was elevated to 50° C. for 6 hours at which point the reaction was diluted with EtOAc and washed with saturated aqueous NaHCO$_3$ solution. The solution was concentrated and purified via flash chromatography on silica gel with a gradient elution of 0% to 15% EtOAc in hexane affording the title compound. HPLC/MS: 396.1 (M+1), 398.1 (M+3); R$_t$=4.77 min.

Step B: N-[3-Acetyl-7-(2-chlorophenyl)-6-(4-chlorophenyl)-1-methyl-2-oxo-1,2-dihydro-1,8-naphthyridin-4-yl]acetamide To the product of step A (269 mg) in pyridine (4 mL) was added DMAP (99.5 mg) and acetic anhydride (1.28 mL). The reaction was heated to 95° C. for 14 hours before quenching with MeOH and then concentrating. The residue was dissolved in CHCl$_3$. The solution was washed with 1 M aqueous HCl and then saturated aqueous NaHCO$_3$ solution before drying (Na$_2$SO$_4$). The concentrated residue was purified by flash chromatography on silica gel with a gradient elution of 5-60% EtOAc in hexane and then by preparative TLC (silica gel) eluted with 33% EtOAc in CH$_2$Cl$_2$ affording the title compound. HPLC/MS: 522.1 (M+1), 524.0 (M+3); R$_t$=4.13 min.

The following examples are reaction byproducts of EXAMPLE 23.

| | Name | HPLC/MS m/z (M + 1) m/z (M + 3) $R_t$ (min) | |
|---|---|---|---|
| EXAMPLE 28 | N-(1-(2,4-dimethoxybenzyl)-3-acetyl-7-(2,4-di-chlorophenyl)-6-(4-chloro-phenyl)-1,2-dihydro-2-oxo-1,8-naph-thyridin-4-yl)-N-acetylacetamide | 691.9 693.9 4.64 | |
| EXAMPLE 29 | N-(1-(2,4-dimethoxybenzyl)-7-(2,4-di-chlorophenyl)-6-(4-chlorophenyl)-1,2-dihydro-2-oxo-1,8-naphthyridin-4-yl)-N-acetyl-acetamide | 650.0 652.0 4.43 | |

EXAMPLE 30

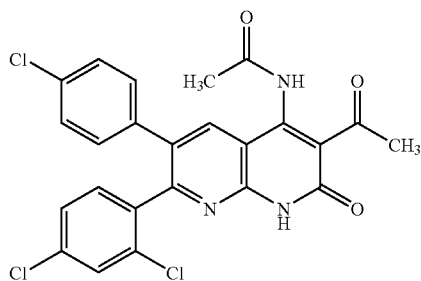

N-[3-acetyl-6-(4-chlorophenyl)-7-(2,4-dichlorophenyl)-2-oxo-1,2-dihydro-1,8-naphthyridin-4-yl]acetamide A solution of the product from EXAMPLE 23 (16 mg) in TFA (1 mL) was stirred about 48 hours. The reaction mixture was quenched with ice/water and extracted twice with $CH_2Cl_2$. The organic layer was washed with $NaHCO_3$ (aq), dried ($Na_2SO_4$), filtered and concentrated in vacuo. Purification on preparative silica TLC plate eluted with 10% methanol in $CH_2Cl_2$ afforded the title compound. HPLC/MS: 500.0 (M+1), 502.0 (M+3); $R_t$ =3.41 min.

EXAMPLE 31

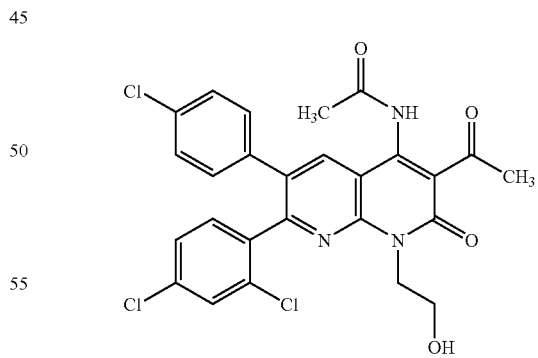

N-[3-acetyl-6-(4-chlorophenyl)-7-(2,4-dichlorophenyl)-1-(2-hydroxyethyl)-2-oxo-1,2-dihydro-1,8-naphthyridin-4-yl]acetamide To the product of EXAMPLE 22 (60 mg) in THF (2 mL) at room temperature was added $K_2CO_3$ (14 mg) and methanol (0.75 mL). After about 2 hours LC/MS indicated incomplete reaction. Cs₂CO₃ (10 mg) in methanol (2 mL) was added and the reaction stirred anther hour before it was partially concentrated. The solution was diluted with EtOAc and washed with brine before drying (Na₂SO₄). The concentrated residue was purified by preparative TLC (silica gel) eluted with 42% EtOAc in CH₂Cl₂ affording the title compound. HPLC/MS: 544.0 (M+1), 546.0 (M+3); R$_t$=4.02 min.

EXAMPLE 32

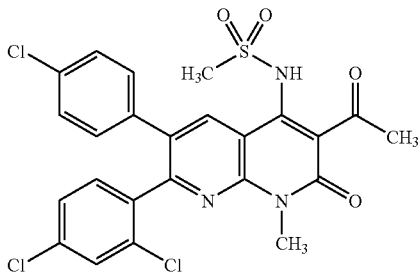

N-[3-acetyl-6-(4-chlorophenyl)-7-(2,4-dichlorophenyl)-1-methyl-2-oxo-1,2-dihydro-1,8-naphthyridin-4-yl]methanesulfonamide The product of Example 2 was reacted with methanesulfonyl chloride using the conditions of EXAMPLE 11 to afford the title compound. HPLC/MS: 549.9 (M+1), 551.9 (M+3); R$_t$=4.24 min.

EXAMPLE 33

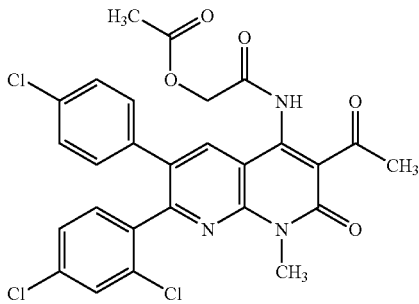

2-{[3-acetyl-6-(4-chlorophenyl)-7-(2,4-dichlorophenyl)-1-methyl-2-oxo-1,2-dihydro-1,8-naphthyridin-4-yl]amino}-2-oxoethyl acetate To the product of Example 2 (120 mg) in acetonitrile (2 mL) was added acetoxyacetyl chloride (0.2 mL). The reaction was heated to 90° C. in a CEM microwave reactor for a total of 34 minutes. The reaction was diluted with EtOAc and was washed with saturated aqueous NaHCO₃ solution. The concentrated residue was purified by flash chromatography on silica gel gradient eluted with 0-60% EtOAc in hexane affording the title compound. HPLC/MS: 572.1 (M+1), 574.1 (M+3); R$_t$=4.06 min.

EXAMPLE 34

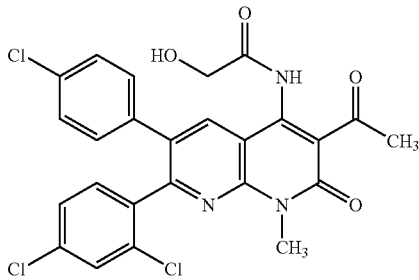

N-[3-acetyl-6-(4-chlorophenyl)-7-(2,4-dichlorophenyl)-1-methyl-2-oxo-1,2-dihydro-1,8-naphthyridin-4-yl]-2-hydroxyacetamide To the product of EXAMPLE 33 (77 mg) in CH₂Cl₂ (2 mL) was added Cs₂CO₃ (43.7 mg) in methanol (1 mL). The reaction stirred at room temperature for 2.5 hours before diluting with EtOAc. The reaction was washed with brine and 10% aqueous NaHSO₄ solution. The concentrated residue was purified by flash chromatography on silica gel gradient eluted with 0-65% EtOAc in hexane affording the title compound. HPLC/MS: 530.1 (M+1), 532.1 (M+3); R$_t$=3.85 min.

EXAMPLE 35

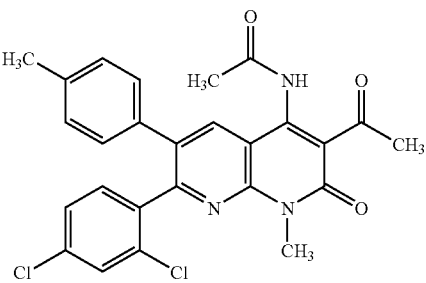

N-[3-Acetyl-7-(2,4-dichlorophenyl)-1-methyl-6-(4-methylphenyl)-2-oxo-1,2-dihydro-1,8-naphthyridin-4-yl]acetamide The title compound was prepared using a similar procedure to that described in Example 1 but substituting 6-(2,4-dichlorophenyl)-2-(methylamino)-5-p-tolylpyridine-3-carbonitrile (0.26 g), acetic anhydride (3 mL), DMAP (0.10 g) and pyridine (5 mL). The reaction was heated at 90° C. overnight. Purification by flash chromatography (silica gel) eluted with 20% EtOAc in CH$_2$Cl$_2$ afforded the title compound. HPLC/MS: 493.9 (M+1), 495.9 (M+3); R$_t$=3.89 min.

EXAMPLE 36

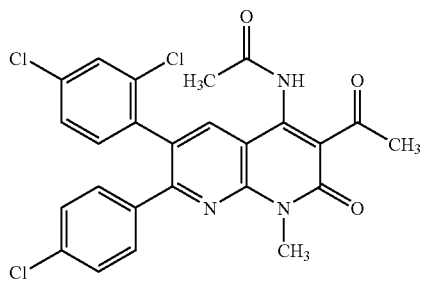

N-[3-acetyl-7-(4-chlorophenyl)-6-(2,4-dichlorophenyl)-1-methyl-2-oxo-1,2-dihydro-1,8-naphthyridin-4-yl]acetamide Using the general procedure of Example 1 Step E 5-(2,4-dichlorophenyl)-6-(4-chlorophenyl)-2-(methylamino)pyridine-3-carbonitrile was treated with acetic anhydride and DMAP in pyridine to afford the title compound. HPLC/MS: 514.0 (M+1), 516.0 (M+3); R$_t$=4.11 min.

EXAMPLE 37

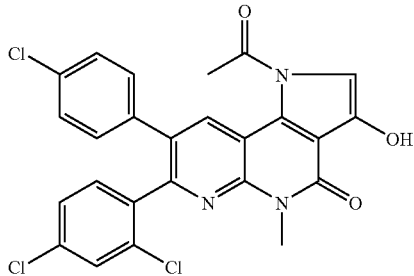

1-acetyl-8-(4-chlorophenyl)-7-(2,4-dichlorophenyl)-3-hydroxy-5-methyl-1,5-dihydro-4H-pyrrolo[3,2-c]-1,8-naphthyridin-4-one Step A: N-[3-(bromoacetyl)-6-(4-chlorophenyl)-7-(2,4-dichlorophenyl)-1-methyl-2-oxo-1,2-dihydro-1,8-naphthyridin-4-yl]acetamide To the product of Example 1 (250 mg) in 1,4-dioxane (3 mL) was added acetic acid (0.20 mL), and Br$_2$ (4 drops). The reaction was heated to 50° C. for 30 min and Br$_2$ (3 drops) was added. After about 90 minutes the reaction was diluted with EtOAc, washed with saturated aqueous NaHCO$_3$ solution and dried (Na$_2$SO$_4$). The concentrated residue was purified by flash chromatography on silica gel with a gradient elution of 0-75% EtOAc in hexane affording the title compound. HPLC/MS: 592.0 (M+1), 594.0 (M+3); R$_t$=4.26 min.

Step B: 1-acetyl-8-(4-chlorophenyl)-7-(2,4-dichlorophenyl)-3-hydroxy-5-methyl-1,5-dihydro-4H-pyrrolo[3,2-c]-1,8-naphthyridin-4-one To the product of Step A (25 mg) was added NaOAc (60 mg) in DMF (2.5 mL) and water (0.3 mL) at room temperature. The reaction stirred overnight and was diluted with EtOAc, washed with saturated aqueous NaHCO$_3$ and brine. The concentrated residue was purified by flash chromatography on silica gel with a gradient elution of 0-100% EtOAc in hexane affording the title compound. HPLC/MS: 512.0 (M+1), 514.0 (M+3); R$_t$=4.18 min.

EXAMPLE 38

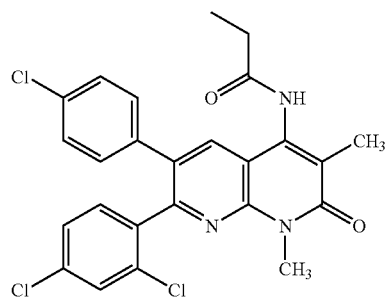

N-[6-(4-chlorophenyl)-7-(2,4-dichlorophenyl)-1,3-dimethyl-2-oxo-1,2-dihydro-1,8-naphthyridin-4-yl]propanamide Step A: N-(7-(2,4-dichlorophenyl)-6-(4-chlorophenyl)-1,2-dihydro-1,3-dimethyl-2-oxo-1,8-naphthyridin-4-yl)-N-propionylpropionamide To the product of step D Example 1 (1.25 g) in pyridine (15 mL) was added DMAP (393 mg) and propionic anhydride (6.19 mL). The reaction was heated to 90° C. for 6.75 hours and then 100° C. until LC/MS indicated that the main product of the reaction was now N-(7-(2,4-dichlorophenyl)-6-(4-chlorophenyl)-1,2-dihydro-1,3-dimethyl-2-oxo-1,8-naphthyridin-4-yl)-N-propionylpropionamide. The reaction was concentrated and the residue was dissolved in CHCl$_3$. The solution was washed with 2 M aqueous HCl/Brine (1:1) and then saturated aqueous NaHCO$_3$ solution before drying with Na$_2$SO$_4$. The concentrated residue was purified by flash chromatography on silica gel with an EtOAc/hexane gradient elution affording the title compound. HPLC/MS: 556.0 (M+1), 558.0 (M+3); R$_t$=4.46 min.

Step B: N-[6-(4-chlorophenyl)-7-(2,4-dichlorophenyl)-1,3-dimethyl-2-oxo-1,2-dihydro-1,8-naphthyridin-4-yl]propanamide To the product of step A (1.56 g) in THF (12 mL) was added methanol (3 mL) and Cs$_2$CO$_3$. The reaction stirred overnight at room temperature before it was diluted with EtOAc and washed with saturated aqueous NaHCO$_3$ solution. The concentrated residue was purified by flash chromatography on

EXAMPLE 39

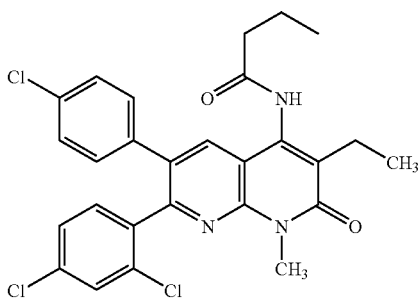

N-[6-(4-chlorophenyl)-7-(2,4-dichlorophenyl)-3-ethyl-1-methyl-2-oxo-1,2-dihydro-1,8-naphthyridin-4-yl]butanamide Using a procedure similar to that described in EXAMPLE 38, the product of step D Example 1 was reacted with butyric anhydride to afford the title compound. HPLC/MS: 528.0 (M+1), 530.0 (M+3); $R_t$=4.29 min.

EXAMPLE 40

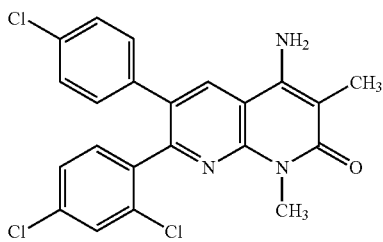

4-amino-6-(4-chlorophenyl)-7-(2,4-dichlorophenyl)-1,3-dimethyl-1,8-naphthyridin-2(1H)-one To N-(6-(2,4-dichlorophenyl)-5-(4-chlorophenyl)-3-cyanopyridin-2-yl)-N-methylpropionamide (92 mg, isolated as a reaction byproduct of EXAMPLE 38) in THF (5 mL) was added NaH (16 mg, 60% dispersion in mineral oil) and 15 minutes later an additional portion of NaH (29 mg, 60% dispersion in mineral oil). The reaction was then quenched with a few drops of acetic acid, diluted with EtOAc and washed with saturated aqueous NaHCO$_3$ solution/brine (1:1). The concentrated residue was purified by flash chromatography (silica gel) gradient eluted with 0-100% EtOAc in hexane affording the title compound. HPLC/MS: 444.0 (M+1), 446.0 (M+3); $R_t$=4.08 min.

EXAMPLE 41

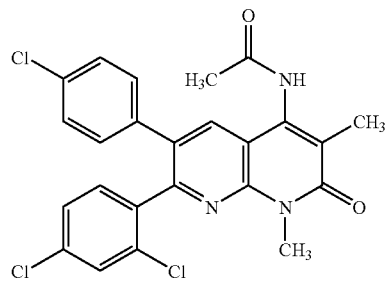

N-[6-(4-chlorophenyl)-7-(2,4-dichlorophenyl)-1,3-dimethyl-2-oxo-1,2-dihydro-1,8-naphthyridin-4-yl] acetamide To the product of EXAMPLE 40 (72 mg) in THF (3 mL) and DMF (0.2 mL) was added NaH (10 mg, 60% dispersion in mineral oil) followed by acetyl chloride (30 µL). After stirring 30 minutes at room temperature NEt$_3$ (45 µL) was added. After an additional hour of reaction time TLC indicated incomplete reaction. Acetyl chloride (15 µL) and NEt$_3$ (45 µL) was added to the reaction, however this generated the imide (N-acetyl-N-(7-(2,4-dichlorophenyl)-6-(4-chlorophenyl)-1,2-dihydro-1,3 dimethyl-2-oxo-1,8-naphthyridinyl)acetamide). The reaction was quenched with methanol and NaHCO$_3$, diluted with EtOAc and washed with 2 M aqueous HCl followed by 1 M aqueous NaOH solution. The solution was concentrated and the residue in 8 mL of 2:1 THF:methanol was treated with CS$_2$O$_3$ (80 mg). TLC indicated conversion of the imide to the amide after about 10 minutes at room temperature. The reaction was concentrated, dissolved in EtOAc and washed with brine. The concentrated solution was then purified by flash chromatography (silica gel) gradient eluted with 0-90% EtOAc in hexane affording the title compound. HPLC/MS: 486.0 (M+1), 488.0 (M+3); $R_t$=4.24 min.

EXAMPLE 42

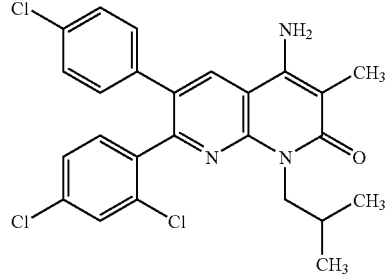

4-amino-6-(4-chlorophenyl)-7-(2,4-dichlorophenyl)-1-isobutyl-3-methyl-1,8-naphthyridin-2(1H)-one Step A: N-(6-(2,4-dichlorophenyl)-5-(4-chlorophenyl)-3-cyanopyridin-2-yl)-N-isobutylpropionamide To 6-(2,4-dichlorophenyl)-5-(4-chlorophenyl)-2-(isobutylamino)pyridine-3-carbonitrile [prepared by reacting the product of Example 1 step C with isobutyl amine] (0.26 g) in (silica gel with an EtOAc/hexane gradient elution affording the title compound. HPLC/MS: 499.8 (M+1), 501.8 (M+3); $R_t$=3.95 min.)

TH (2.5 mL) was added MeMgBr (0.47 mL, 1.4 M solution in toluene THF 3:1) followed by propionyl chloride. After 1 hour 45 minutes the reaction was quenched with 2 M aqueous HCl, diluted with EtOAc and washed with saturated aqueous $NaHCO_3$ solution. The dried solution ($Na_2SO_4$) was concentrated and purified via flash chromatography on silica gel eluted with 20% EtOAc in hexane affording the title compound. HPLC/MS: 486.2(M+1), 488.2 (M+3); $R_t$=4.60 min.

Step B: 4-amino-6-(4-chlorophenyl)-7-2,4-dichlorophenyl)-1-isobutyl-3-methyl-1,8-naphthyridin-2(1H)-one Using the general procedure of EXAMPLE 40 the product of Step A was treated with NaH to afford the title compound. HPLC/MS: 486.2(M+1), 488.2 (M+3); $R_t$=4.56 min.

EXAMPLE 43

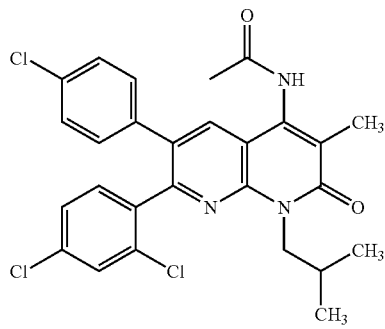

N-[6-(4-chlorophenyl)-7-(2,4-dichlorophenyl)-1-isobutyl-3-methyl-2-oxo-1,2-dihydro-1,8-naphthyridin-4-yl]acetamide To the product of EXAMPLE 42 (28 mg) in THF (0.5 mL) at 0° C. was added NaH (5 mg, 60% dispersion in mineral oil). The reaction stirred 10 minutes before acetyl chloride (7 μL) was added. Two hours later an additional 20 μL portion of acetyl chloride was added and again after an additional 90 minutes. After an additional hour of reaction time the reaction was diluted with EtOAc and washed with saturated aqueous $NaHCO_3$ solution and dried ($Na_2SO_4$). The concentrated residue was purified by preparative TLC on silica gel eluted with 70% EtOAc in hexane affording the title compound. HPLC/MS: 528.0 (M+1), 530.0 (M+3); $R_t$=4.27 min.

EXAMPLE 44

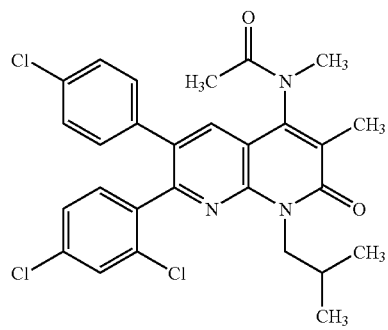

N-[6-(4-chlorophenyl)-7-(2,4-dichlorophenyl)-1-isobutyl-3-methyl-2-oxo-1,2-dihydro-1,8-naphthyridin-4-yl]-N-methylacetamide Using the general procedure of EXAMPLE 12 the product of EXAMPLE 43 was reacted with iodomethane to afford the title compound. HPLC/MS: 542.2 (M+1), 544.2 (M+3); $R_t$=4.40 min.

Using the product of EXAMPLE 42 and treating with NaH and the appropriate acid chloride or ethylisocyante (last example) the following examples were prepared using similar procedures described in reaction Schemes 1 to 11 and in the preceding examples.

EXAMPLE 45-EXAMPLE 48

|  | Name | HPLC/MS m/z (M + 1) m/z (M + 3) $R_t$ (min) |  |
| --- | --- | --- | --- |
| EXAMPLE 45 | 2-{[6-(4-chlorophenyl)-7-(2,4-dichlorophenyl)-1-isobutyl-3-methyl-2-oxo-1,2-dihydro-1,8-naphthyridin-4-yl]amino}-2-oxoethyl acetate | 586.1 588.1 4.13 | 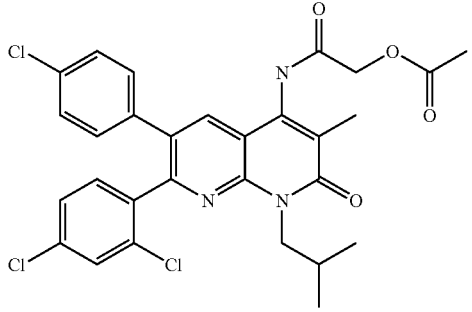 |

| Name | HPLC/MS m/z (M + 1) m/z (M + 3) $R_t$ (min) | |
|---|---|---|
| EXAMPLE 46 | 2-chloro-N-[6-(4-chlorophenyl)-7-(2,4-di-chlorophenyl)-1-isobutyl-3-methyl-2-oxo-1,2-di-hydro-1,8-naphthyridin-4-yl]acet-amide | 561.9<br>563.9<br>4.43 |
| EXAMPLE 47 | N-[6-(4-chlorophenyl)-7-(2,4-di-chlorophenyl)-1-isobutyl-3-methyl-2-oxo-1,2-di-hydro-1,8-naphthyridin-4-yl]-2-meth-oxyacetamide | 558.0<br>560.0<br>4.42 |
| EXAMPLE 48 | N-[6-(4-chlorophenyl)-7-(2,4-di-chlorophenyl)-1-isobutyl-3-methyl-2-oxo-1,2-di-hydro-1,8-naphthyridin-4-yl]-N'-eth-ylurea | 556.9<br>558.9<br>4.32 |

EXAMPLE 49

N-[3-chloro-6-(4-chlorophenyl)-7-(2,4-dichlorophenyl)-1-isobutyl-2-oxo-1,2-dihydro-1,8-naphthyridin-4-yl]-2-hydroxyacetamide Using the general deprotection procedure of EXAMPLE 31 the product of EXAMPLE 45 was reacted with $Cs_2CO_3$ and methanol to cleave the acetate affording the title compound. HPLC/MS: 544.1 (M+1), 546.1 (M+3); $R_t$=4.16 min.

EXAMPLE 50

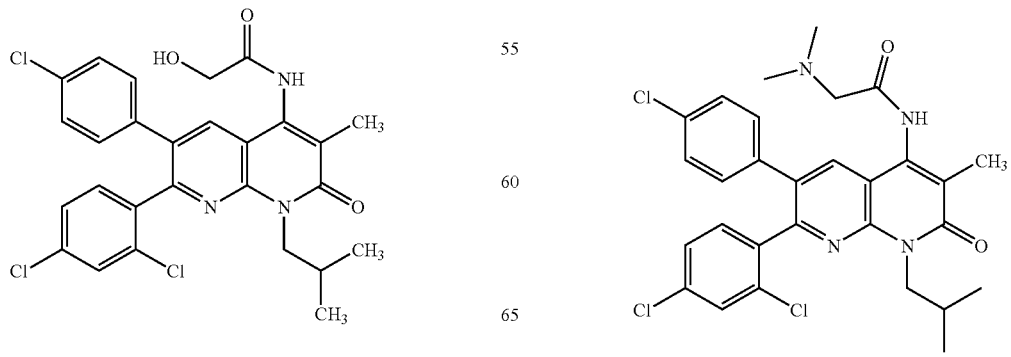

N1-[6-(4-chlorophenyl)-7-2,4-dichlorophenyl)-1-isobutyl-3-methyl-2-oxo-1,2-dihydro-1,8-naphthyridin-4-yl]-N²,N²-dimethylglycinamide

EXAMPLE 53

To the product of EXAMPLE 46 (46 mg) in THF (1 mL) was added HN(CH₃)₂ (0.50 mL, 2 M solution in THF) and KI (50 mg). After 3h the reaction was diluted with EtOAc and washed with saturated aqueous NaHCO₃ solution. The dried solution (Na₂SO₄) was concentrated and purified via flash chromatography on silica gel gradient eluted with 50-100% EtOAc in hexane affording the title compound. HPLC/MS: 571.0 (M+1), 572.9 (M+3); $R_t$=3.56 min.

Using the product of EXAMPLE 46 and treating with the either NH₃ or H₂NCH₃ the following examples were prepared using similar procedures to that described in EXAMPLE 50

EXAMPLE 51-EXAMPLE 52

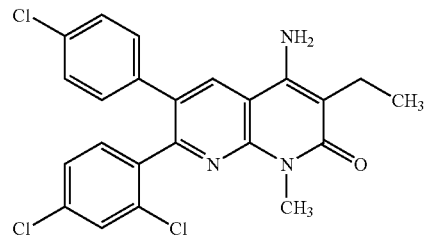

|  | Name | HPLC/MS<br>m/z (M + 1)<br>m/z (M + 3)<br>$R_t$ (min) |
|---|---|---|
| EXAMPLE 51 | N¹-[6-(4-chlorophenyl)-7-(2,4-dichlorophenyl)-1-isobutyl-3-methyl-2-oxo-1,2-dihydro-1,8-naphthyridin-4-yl]-N²-methylglycinamide | 557.0<br>558.9<br>3.53 |

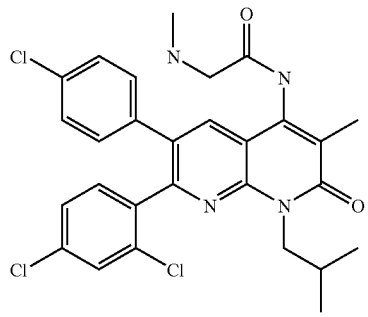

| EXAMPLE 52 | N¹-[6-(4-chlorophenyl)-7-(2,4-dichlorophenyl)-1-isobutyl-3-methyl-2-oxo-1,2-dihydro-1,8-naphthyridin-4-yl]glycinamide | 543.0<br>544.9<br>3.48 |

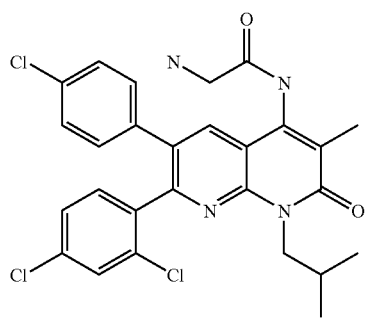

4-amino-6-(4-chlorophenyl)-7-(2,4-dichlorophenyl)-3-ethyl-1-methyl-1,8-naphthyridin-2(1H)-one Step A: N-(6-(2,4-dichlorophenyl)-5-(4-chlorophenyl)-3-cyanopyridin-2-yl)-N-methylbutyramide The product of Step D Example 1 was reacted with MeMgBr followed by butyryl chloride using the procedure of EXAMPLE 42 Step A to afford the title compound.

Step B: 4-amino-6-(4-chlorophenyl)-7-(2,4-dichlorophenyl)-3-ethyl-1-methyl-1,8-naphthyridin-2(1H)-one Using the procedure described in EXAMPLE 40, the product of Step A was reacted with NaH to afford the title compound. HPLC/MS: 457.9 (M+I), 459.9 (M+3); $R_t$=4.29 min.

EXAMPLE 54

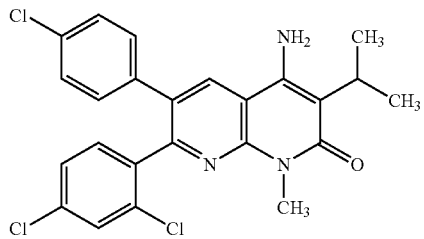

4-amino-6-(4-chlorophenyl)-7-(2,4-dichlorophenyl)-3-isopropyl-1-methyl-1,8-naphthyridin-2(1H)-one Step A: N-(6-(2,4-dichlorophenyl)-5-(4-chlorophenyl)-3-cyanopyridin-2-yl)-N,3-dimethylbutanamide The product of Step D Example 1 was reacted with MeMgBr followed by 3-methylbutanoyl chloride using the procedure of EXAMPLE 42 Step A to afford the title compound. HPLC/MS: 472.2 (M+1), 474.2 (M+3); $R_t$=4.43 min.

Step B: 4-amino-6-(4-chlorophenyl)-7-(2,4-dichlorophenyl)-3-isopropyl-1-methyl-1,8-naphthyridin-2(1H)-one Using the procedure described in EXAMPLE 40, the product of Step A was reacted with NaH to afford the title compound. HPLC/MS: 472.2 (M+1), 474.2 (M+3); $R_t$=4.45 min.

EXAMPLE 55

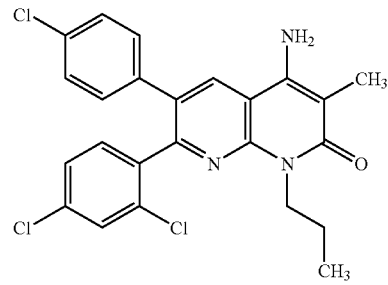

4-amino-6-(4-chlorophenyl)-7-(2,4-dichlorophenyl)-3-methyl-1-propyl-1,8-naphthyridin-2(1H)-one Step A: N-(6-(2,4-dichlorophenyl)-5-(4-chlorophenyl)-3-cyanopyridin-2-yl)-N-propylpropionamide 6-(2,4-dichlorophenyl)-5-(4-chlorophenyl)-2-(propylamino)pyridine-3-carbonitrile (prepared by reaction of the product of Step C Example 1 with propylamine using the procedure of Step D EXAMPLE 26) was reacted with MeMgBr followed by propionyl chloride using the procedure of EXAMPLE 42 Step A to afford the title compound. HPLC/MS: 472.1 (M+1), 474.1 (M+3); $R_t$=4.40 min.

Step B: 4-amino-6-(4-chlorophenyl)-7-2,4-dichlorophenyl)-3-methyl-1-propyl-1,8-naphthyridin-2(1H)-one Using the procedure described in EXAMPLE 40, the product of Step A was reacted with NaH to afford the title compound. HPLC/MS: 472.0 (M+1), 474.0 (M+3); $R_t$=4.43 min.

Using the products of Example 53, EXAMPLE 54, EXAMPLE 55 and reacting them with acetyl chloride the following examples were prepared using similar procedures to that described in EXAMPLE 43.

|  | Name | HPLC/MS<br>m/z (M + 1)<br>m/z (M + 3)<br>$R_t$ (min) |
|---|---|---|
| EXAMPLE 56 | N-[6-(4-chlorophenyl)-7-(2,4-dichlorophenyl)-3-ethyl-1-methyl-2-oxo-1,2-dihydro-1,8-naphthyridin-4-yl]acetamide | 500.0<br>502.0<br>4.55 |
| EXAMPLE 57 | N-[6-(4-chlorophenyl)-7-(2,4-dichlorophenyl)-3-isopropyl-1-methyl-2-oxo-1,2-dihydro-1,8-naphthyridin-4-yl]acetamide | 514.0<br>516.0<br>4.13 |

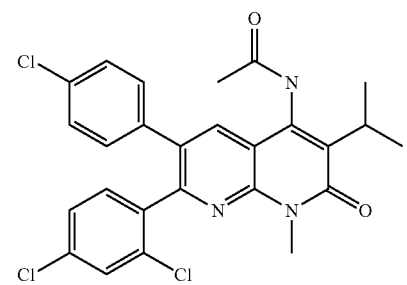

| | Name | HPLC/MS m/z (M + 1) m/z (M + 3) R$_t$(min) | |
|---|---|---|---|
| EXAMPLE 58 | N-[6-(4-chlorophenyl)-7-(2,4-dichlorophenyl)-3-methyl-2-oxo-1-propyl-1,2-dihydro-1,8-naphthyridin-4-yl]acetamide | 514.0<br>516.0<br>4.19 | |
| EXAMPLE 59 | N-[6-(4-chlorophenyl)-7-(2,4-dichlorophenyl)-3-ethyl-1-isobutyl-2-oxo-1,2-dihydro-1,8-naphthyridin-4-yl]acetamide | 542.2<br>544.2<br>4.37 | |

EXAMPLE 60

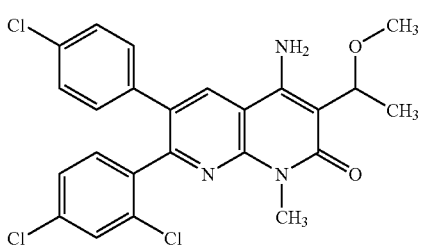

4-amino-6-(4-chlorophenyl)-7-(2,4-dichlorophenyl)-3-(1-methoxyethyl)-1-methyl-1,8-naphthyridin-2(1H)-one The product of Example 3 (50 mg) in THF (1 mL) was combined with methansulfonyl chloride (15 µL) and triethylamine (27 µL) at 0° C. The reaction stirred 15 minutes at which point methanol (2 mL) was added. The reaction stirred 4.5 hours before it was diluted with EtOAc and washed with water. The organic layer was dried (Na$_2$SO$_4$), filtered and concentrated in vacuo. Purification by flash chromatography on silica eluted with 0-20% EtOAc in hexane afforded the title compound. HPLC/MS: 488.0 (M+1), 490.0 (M+3); R$_t$=4.45 min.

EXAMPLE 61

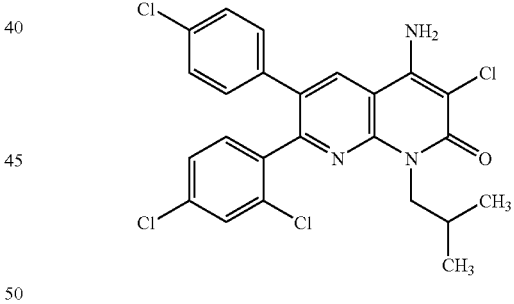

4-amino-3-chloro-6-(4-chlorophenyl)-7-(2,4-dichlorophenyl)-1-isobutyl-1,8-naphthyridin-2(1H)-one To 2-chloro-N-6-(2,4-dichlorophenyl)-5-(4-chlorophenyl)-3-cyanopyridin-2-yl)-N-isobutylacetamide (305 mg) [prepared by the reaction of the product of Step A EXAMPLE 27 with chloroacetyl chloride using the method of EXAMPLE 42 Step A] in THF (2 mL) was added NaH (48 mg, 60% dispersion in mineral oil). The reaction stirred at room temperature for 20 minutes before it was quenched with a few drops of acetic acid. The reaction was diluted with EtOAc, and washed with saturated aqueous NaHCO$_3$ solution. The concentrated residue was purified by flash chromatography on silica gel gradient eluted with 25-50% EtOAc in hexane and further purified by recrystallization from EtOAc to afford the title compound. HPLC/MS: 506.0 (M+1), 508.0 (M+3); $R_t$=4.56 min.

EXAMPLE 62

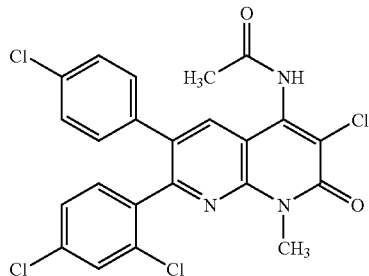

N-[3-chloro-6-(4-chlorophenyl)-7-(2,4-dichlorophenyl)-1-methyl-2-oxo-1,2-dihydro-1,8-naphthyridin-4-yl]acetamide Step A: 2-chloro-N-6-(2,4-dichlorophenyl)-5-(4-chlorophenyl)-3-cyanopyridin-2-yl)-N-methylacetamide To the product of Step D Example 1 (543 mg) in THF (6.3 mL) was added MeMgBr (1.10 mL, 1.4 M solution in toluene/TH 3:1) at 0° C. The reaction stirred for 5 minutes before adding chloroacetyl chloride (0.122 mL). The reaction stirred 1 hour and was diluted with EtOAc, washed with 2 M aqueous HCl and brine. The dried solution ($Na_2SO_4$) was concentrated and purified via flash chromatography on silica gel gradient eluted with 0-50% EtOAc in hexane affording the title compound. HPLC/MS: 464.1 (M+1), 466.1 (M+3); $R_t$=4.69 min.

Step B: N-[3-chloro-6-(4-chlorophenyl)-7-(2,4-dichlorophenyl)-1-methyl-2-oxo-1,2-dihydro-1,8-naphthyridin-4-yl]acetamide To the product to Step A (100 mg) in THF (1.5 mL) and DMF (0.3 mL) was added NaH (13 mg, 60% dispersion in mineral oil) at 0° C. After about 10 minutes acetyl chloride (61.4 µL) was added. An additional portion of acetyl chloride (30 µL) was added. Analysis of the reaction solution indicated a distribution between the 4-amino, 4-N-acetamide and 4-di-N-acetamide. The imide was cleaved by adding a solution of $Cs_2CO_3$ (about 200 mg) in methanol (about 5 mL). The reaction was diluted with EtOAc and washed with saturated aqueous $NaHCO_3$ solution and then brine. The concentrated residue was purified by flash chromatography on silica gel gradient eluted with 0-100% EtOAc in hexane affording the title compound. HPLC/MS: 506.0 (M+1), 508.0 (M+3); $R_t$=4.50 min.

EXAMPLE 63

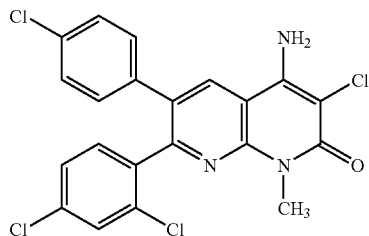

4-amino-3-chloro-6-(4-chlorophenyl)-7-(2,4-dichlorophenyl)-1-methyl-1,8-naphthyridin-2(1H)-one The title compound was isolated as a side product of EXAMPLE 62. HPLC/MS: 464.0 (M+1), 466.0 (M+3); $R_t$=4.13 min.

EXAMPLE 64

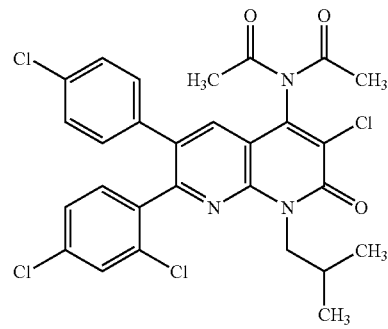

N-acetyl-N-(3-chloro-7-(2,4-dichlorophenyl)-6-(4-chlorophenyl)-1,2-dihydro-1-isobutyl-2-oxo-1,8-naphthyridin-4-yl)acetamide To the product of EXAMPLE 61 (70 mg) in 1,4-dioxane (1 mL) was added acetic anhydride (2 mL) and DMAP (25 mg). The reaction was heated to 60° C. After about 1 hour the reaction was cooled to room temperature and quenched with methanol (1 mL) the reaction was diluted with EtOAc and washed with saturated aqueous $NaHCO_3$/1 M aqueous NaOH solution (1:1). The organic layer was dried ($Na_2SO_4$). The concentrated residue was purified by flash chromatography on silica gel gradient eluted with 0-100% EtOAc in hexane affording the title compound. HPLC/MS: 590.0 (M+1), 592.0 (M+3); $R_t$=4.59 min.

EXAMPLE 65

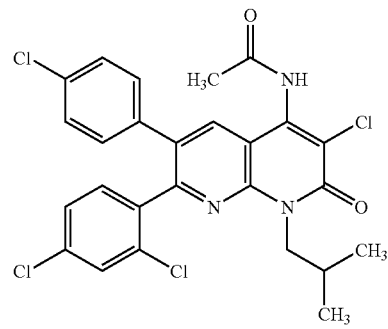

N-[3-chloro-6-(4-chlorophenyl)-7-(2,4-dichlorophenyl)-1-isobutyl-2-oxo-1,2-dihydro-1,8-naphthyridin-4-yl]acetamide The product of EXAMPLE 64 (40 mg) was combined with methanol (8 mL), THF (2.5 mL) water (0.4 mL) and triethylamine (0.5 mL) at room temperature. After 1 hour the reaction was concentrated and the residue dissolved in EtOAc. The solution was washed with saturated aqueous NaHCO₃ and brine. The organic layer was dried (Na₂SO₄). The concentrated residue was purified by preparative TLC on silica gel eluted with 75% EtOAc in hexane affording the title compound. HPLC/MS: 547.9 (M+1), 549.9 (M+3); $R_t$=4.32 min.

Starting with the product of EXAMPLE 61 and using the procedures described in reaction Schemes 1 through 11 and in the preceding Examples, the following additional compounds were prepared.

| | Name | HPLC/MS m/z (M + 1) m/z (M + 3) $R_t$ (min) |
|---|---|---|
| EXAMPLE 66 | $N^1$-[3-chloro-6-(4-chlorophenyl)-7-(2,4-dichlorophenyl)-1-isobutyl-2-oxo-1,2-dihydro-1,8-naphthyridin-4-yl]-$N^2$,$N^2$-dimethylglycinamide | 591.0 593.0 3.60 |
| EXAMPLE 67 | 2-{[3-chloro-6-(4-chlorophenyl)-7-(2,4-dichlorophenyl)-1-isobutyl-2-oxo-1,2-dihydro-1,8-naphthyridin-4-yl]amino}-2-oxo-ethyl acetate | 606.1 608.0 4.37 |
| EXAMPLE 68 | N-[3-chloro-6-(4-chlorophenyl)-7-(2,4-dichlorophenyl)-1-isobutyl-2-oxo-1,2-dihydro-1,8-naphthyridin-4-yl]-2-hydroxyacetamide | 563.9 565.9 4.16 |

EXAMPLE 69

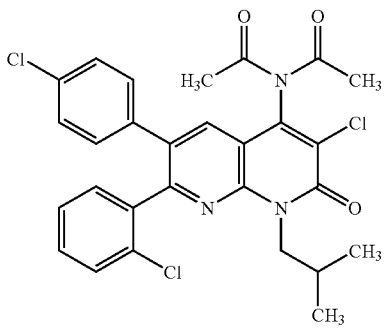

N-acetyl-N-(3-chloro-7-(2-chlorophenyl)-6-(4-chlorophenyl)-1,2-dihydro-1-isobutyl-2-oxo-1,8-naphthyridin-4-yl)acetamide Step A: 2-chloro-N-(6-(2-chlorophenyl)-5-(4-chlorophenyl)-3-cyanopyridin-2-yl)-N-isobutylacetamide To the product of Step A EXAMPLE 27 (300 mg) in THF (5.0 mL) was added MeMgBr (0.92 mL, 1.4 M solution in toluene/THF 3:1) at 0° C. The reaction stirred for 5 minutes before adding chloroacetyl chloride (0.08 mL). The reaction stirred about 7 hours and was diluted with EtOAc, washed with 2 M aqueous HCl and brine. The dried solution ($Na_2SO_4$) was concentrated and purified via flash chromatography on silica gel gradient eluted with 0-15% EtOAc in hexane affording the title compound. HPLC/MS: 471.9 (M+1), 473.9 (M+3); $R_t$=4.32 min.

Step B: N-acetyl-N-(3-chloro-7-(2-chlorophenyl)-6-(4-chlorophenyl)-1,2-dihydro-1-isobutyl-2-oxo-1,8-naphthyridin-4-yl)acetamide To the product to Step A (160 mg) in THF (5.0 mL) and DMF (0.5 mL) was added NaH (20 mg, 60% dispersion in mineral oil) at room temperature. After 20 minutes acetic anhydride (0.5 mL) and DMAP (30 mg) was added. The reaction was heated to 60° C. for about 2.5 hours. The reaction was quenched with methanol (1 mL) and diluted with EtOAc. It was washed with saturated aqueous $NaHCO_3$ solution. The concentrated residue was purified by flash chromatography on silica gel gradient eluted with 0-20% EtOAc in hexane affording the title compound. HPLC/MS: 555.9 (M+1), 557.8 (M+3); $R_t$=4.37 min.

EXAMPLE 70

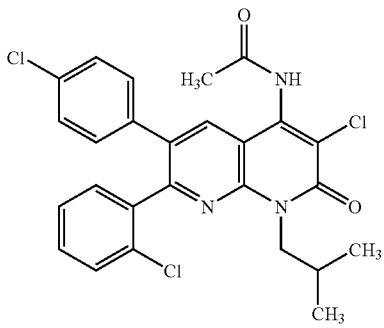

N-[3-chloro-7-(2-chlorophenyl)-6-(4-chlorophenyl)-1-isobutyl-2-oxo-1,2-dihydro-1,8-naphthyridin-4-yl]acetamide The product of EXAMPLE 69 (85 mg) was combined with methanol (7 mL), THF (4 mL) water (2 mL) and triethylamine (2 mL) at room temperature. After 1.5 hours the reaction was concentrated and the residue dissolved in EtOAc. The solution was washed with saturated aqueous $NaHCO_3$ and brine. The organic layer was dried ($Na_2SO_4$). The concentrated residue was purified by flash chromatography on silica gel eluted with 0-50% EtOAc in hexane affording the title compound. HPLC/MS: 513.9 (M+I), 515.9 (M+3); $R_t$=4.05 min.

EXAMPLE 71

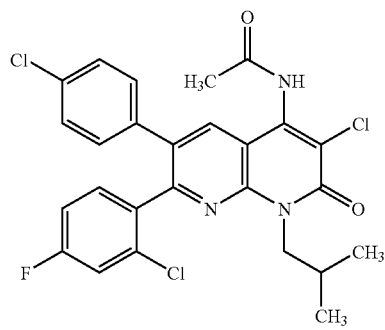

N-[3-chloro-7-(2-chloro-4-fluorophenyl)-6-(4-chlorophenyl)-1-isobutyl-2-oxo-1,2-dihydro-1,8-naphthyridin-4-yl]acetamide Step A: 6-(2-chloro-4-fluorophenyl)-5-(4-chlorophenyl)-2-(isobutylamino)pyridine-3-carbonitrile 2-chloro-6-(2-chloro-4-fluorophenyl)-5-(4-chlorophenyl)pyridine-3-carbonitrile (prepared from 6-(2-chloro-4-fluorophenyl)-5-(4-chlorophenyl)-1,2-dihydro-2-oxopyridine-3-carbonitrile using conditions similar to Step C Example 1) was reacted with isobutylamine using the conditions of Step A EXAMPLE 27 to afford the title compound. HPLC/MS: 414.1 (M+1), 415.9 (M+3); $R_t$=4.68 min.

Step B: 2-chloro-N-(6-(2-chloro-4-fluorophenyl)-5-(4-chlorophenyl)-3-cyanopyridin-2-yl)-N-isobutylacetamide The product of Step A was reacted with chloroacetyl chloride using conditions similar to EXAMPLE 62 Step A to afford the title compound. HPLC/MS: 489.9 (M+1), 491.8 (M+3); $R_t$=4.40 min.

Step C: N-[3-chloro-7-(2-chloro-4-fluorophenyl)-6-(4-chlorophenyl)-1-isobutyl-2-oxo-1,2-dihydro-1,8-naphthyridin-4-yl]acetamide To the product to Step B (80 mg) in THF (2.5 mL) and DMF (0.3 mL) was added NaH (8 mg, 60% dispersion in mineral oil) at room temperature. After about 20 minutes acetic anhydride (0.17 mL) and DMAP (18 mg) was added. The reaction was heated to 55° C. LC/MS indicates N-acetyl-N-3-chloro-7-(2-chloro-4-fluorophenyl)-6-(4-chlorophenyl)-1,2-dihydro-1-isobutyl-2-oxo-1,8-naphthyridin-4-yl)acetamide had formed. The reaction was diluted with EtOAc. It was washed with saturated aqueous $NaHCO_3$ solution. The concentrated residue was purified by flash chromatography on silica gel gradient eluted with 0-100% EtOAc in hexane. The purified material was subject to conditions similar to EXAMPLE 65 to afford the title compound. HPLC/MS: 531.9 (M+1), 533.8 (M+3); $R_t$=4.13 min.

EXAMPLE 72

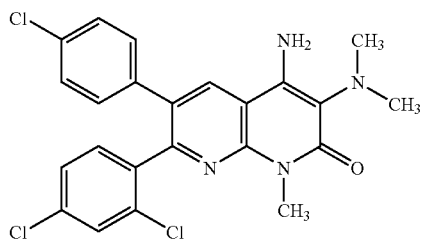

4-amino-6-(4-chlorophenyl)-7-(2,4-dichlorophenyl)-3-(dimethylamino)-1-methyl-1,8-naphthyridin-2(1H)-one Step A: N-(6-(2,4-dichlorophenyl)-5-(4-chlorophenyl)-3-cyanopyridin-2-yl)-2-(dimethylamino)-N-methylacetamide To the product of Step A EXAMPLE 62 (80 mg) in DMF (1.5 mL) was added HN(CH$_3$)$_2$ (1.50 mL, 2 M solution in THF) and KI (29 mg). After 1 hour the reaction was concentrated and then diluted with EtOAc. The solution was washed with 2 M aqueous HCl/brine (1:1) followed by saturated aqueous NaHCO$_3$ solution. The dried solution (Na$_2$SO$_4$) was concentrated affording the title compound. HPLC/MS: 473.0 (M+1), 475.0 (M+3); $R_t$=2.70 min.

Step B: 4-amino-6-(4-chlorophenyl)-7-(2,4-dichlorophenyl)-3-dimethylamino)-1-methyl-1,8-naphthyridin-2(1H)-one To the product to Step A (76.3 mg) in THF (3 mL) and DMF (0.3 mL) was added NaH (10 mg, 60% dispersion in mineral oil). After 45 minutes the reaction was complete. The reaction was diluted with EtOAc and washed with saturated aqueous NaHCO$_3$ solution and then brine. The concentrated residue was purified by flash chromatography on silica gel gradient eluted with 0-100% EtOAc in hexane affording the title compound. HPLC/MS: 473.1 (M+1), 475.1 (M+3); $R_t$=0.88 min (using an ultrafast LC/MS method).

EXAMPLE 73

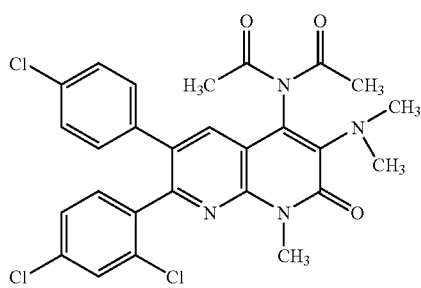

N-acetyl-N-(7-(2,4-dichlorophenyl)-6-(4-chlorophenyl)-3-(dimethylamino)-1,2-dihydro-1-methyl-2-oxo-1,8-naphthyridin-4-yl)acetamide To the product of EXAMPLE 72 (48.8 mg) in 1,4-dioxane (1 mL) was added acetic anhydride (2 mL) and DMAP (20 mg). The reaction was heated to 105° C. After about 1 hour the reaction was cooled to room temperature and diluted with EtOAc. The solution washed with saturated aqueous NaHCO$_3$/1 M aqueous NaOH solution (1:1). The organic layer was dried (Na$_2$SO$_4$). The concentrated residue was purified by flash chromatography on silica gel gradient eluted with 0-100% EtOAc in hexane affording the title compound. HPLC/MS: 557.1 (M+1), 559.1 (M+3); $R_t$=4.40 min.

EXAMPLE 74

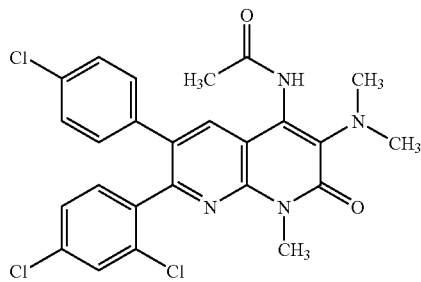

N-[6-(4-chlorophenyl)-7-(2,4-dichlorophenyl)-3-(dimethylamino)-1-methyl-2-oxo-1,2-dihydro-1,8-naphthyridin-4-yl]acetamide The product of EXAMPLE 73 (44 mg) was combined with methanol (6 mL), water (0.65 mL) and triethylamine (0.8 mL) at room temperature. After 2.5 hours the reaction was concentrated and the residue dissolved in EtOAc. The solution was washed with saturated aqueous NaHCO$_3$ and brine. The concentrated residue was purified by flash chromatography on silica gel eluted with 0-100% EtOAc in hexane affording the title compound. HPLC/MS: 515.0 (M+1), 517.0 (M+3); $R_t$=3.55 min.

Starting with the product of Step A EXAMPLE 62 and using the procedures described in reaction Schemes 1 to 11 and in the preceding Examples, the following additional compounds were prepared by initial reaction with either pyrrolidine or N-methylpropan-2-amine.

| | Name | HPLC/MS m/z (M + 1) m/z (M + 3) R_t (min) | |
|---|---|---|---|
| EXAMPLE 75 | 4-amino-6-(4-chlorophenyl)-7-(2,4-dichlorophenyl)-3-[isopropyl(methyl)amino]-1-methyl-1,8-naphthyridin-2(1H)-one | 501.1<br>503.1<br>3.60 | |
| EXAMPLE 76 | N-(3-(N-isopropyl-N-methylamino)-7-(2,4-dichlorophenyl)-6-(4-chlorophenyl)-1,2-dihydro-1-methyl-2-oxo-1,8-naphthyridin-4-yl)-N-acetylamide | 585.0<br>587.0<br>4.59 | |
| EXAMPLE 77 | N-{6-(4-chlorophenyl)-7-(2,4-dichlorophenyl)-3-[isopropyl(methyl)amino]-1-methyl-2-oxo-1,2-dihydro-1,8-naphthyridin-4-yl}acetamide | 543.0<br>545.0<br>3.81 | |
| EXAMPLE 78 | N-acetyl-N-(7-(2,4-dichlorophenyl)-6-(4-chlorophenyl)-1,2-dihydro-1-methyl-2-oxo-3-(pyrrolidin-1-yl)-1,8-naphthyridin-4-yl)acetamide | 583.0<br>585.0<br>4.53 | |
| EXAMPLE 79 | N-[6-(4-chlorophenyl)-7-(2,4-dichlorophenyl)-1-methyl-2-oxo-3-pyrrolidin-1-yl-1,2-dihydro-1,8-naphthyridin-4-yl]acetamide | 541.0<br>543.0<br>3.60 | |

EXAMPLE 80

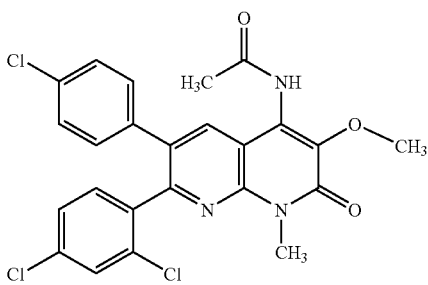

N-[6-(4-chlorophenyl)-7-(2,4-dichlorophenyl)-3-methoxy-1-methyl-2-oxo-1,2-dihydro-1,8-naphthyridin-4-yl]acetamide N-(6-(2,4-dichlorophenyl)-5-(4-chlorophenyl)-3-cyanopyridin-2-yl)-2-methoxy-N-methylacetamide (368.5 mg, prepared by the reaction of the product of Step A Example 1 with 2-methoxyacetyl chloride using the conditions of EXAMPLE 62 Step A) was combined with THF (5 mL), DMF (0.5 mL) and NaH (48 mg, 60% dispersion in mineral oil). After 15 minutes the reaction was quenched with acetic acid (0.2 mL). The reaction was diluted with EtOAc and washed with saturated aqueous NaHCO$_3$ solution and brine. The concentrated residue was suspended in THF (4 mL), DMF (0.5 mL) and acetyl chloride (0.5 mL). Once LC/MS indicated the acylation was complete, the reaction was diluted with EtOAc and washed with saturated aqueous NaHCO$_3$ solution and brine. The concentrated residue was purified by flash chromatography on silica gel gradient eluted with 0-100% EtOAc in hexane affording the title compound. HPLC/MS: 502.0 (M+1), 504.00 (M+3); R$_t$=3.92 min.

EXAMPLE 81

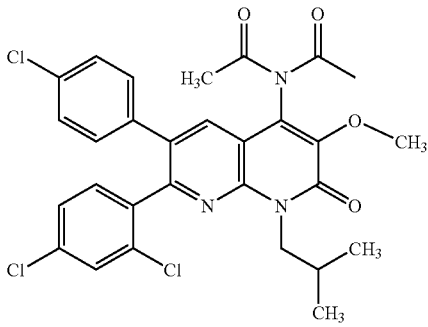

N-acetyl-N-(7-(2,4-dichlorophenyl)-6-(4-chlorophenyl)-1,2-dihydro-1-isobutyl-3-methoxy-2-oxo-1,8-naphthyridin-4-yl)acetamide N-(6-(2,4-dichlorophenyl)-5-(4-chlorophenyl)-3-cyanopyridin-2-yl)-N-isobutyl-2-methoxyacetamide (prepared by the reaction of 6-(2,4-dichlorophenyl)-5-(4-chlorophenyl)-2-(isobutylamino)pyridine-3-carbonitrile with 2-methoxyacetyl chloride using the conditions of EXAMPLE 62 Step A) was reacted with NaH using the conditions of EXAMPLE 80 affording 4-amino-7-(2,4-dichlorophenyl)-6-(4-chlorophenyl)-1-isobutyl-3-methoxy-1,8-naphthyridin-2(1H)-one which was acylated according to the procedure of EXAMPLE 64 affording the title compound. HPLC/MS: 586.0 (M+1), 5587.8 (M+3); R$_t$=4.64 min.

EXAMPLE 82

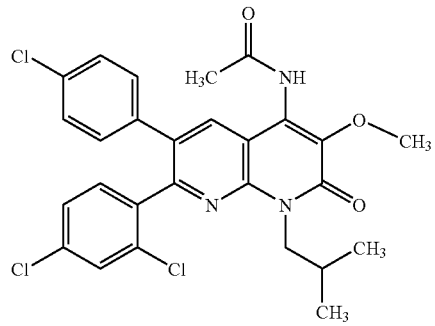

N-[6-(4-chlorophenyl)-7-(2,4-dichlorophenyl)-1-isobutyl-3-methoxy-2-oxo-1,2-dihydro-1,8-naphthyridin-4-yl]acetamide The product of EXAMPLE 81 was treated to the conditions of EXAMPLE 65 affording the title compound. HPLC/MS: 544.0 (M+1), 545.9 (M+3); R$_t$=4.36 min.

EXAMPLE 83

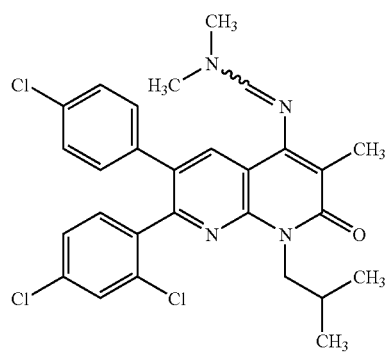

N'-[6-(4-chlorophenyl)-7-(2,4-dichlorophenyl)-1-isobutyl-3-methyl-2-oxo-1,2-dihydro-1,8-naphthyridin-4-yl]-N,N-dimethylimidoformamide The title compound (E/Z mixture of isomers) was isolated as a side product of EXAMPLE 43. HPLC/MS: 541.2 (M+1), 543.2 (M+3); $R_t$=3.65 min.

EXAMPLE 84

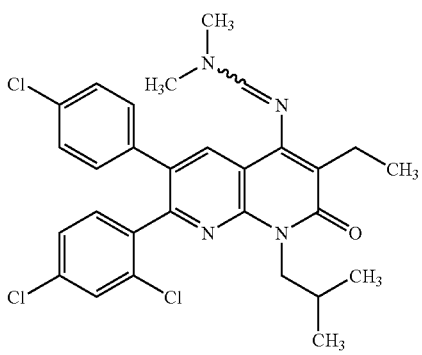

N'-[6-(4-chlorophenyl)-7-(2,4-chlorophenyl)-3-ethyl-1-isobutyl-2-oxo-1,2-dihydro-1,8-naphthyridin-4-yl]-N,N-dimethylimidoformamide The title compound (E/Z mixture of isomers) was isolated as a side product of EXAMPLE 59. HPLC/MS: 555.2 (M+1), 557.2 (M+3); $R_t$=3.73 min.

EXAMPLE 85

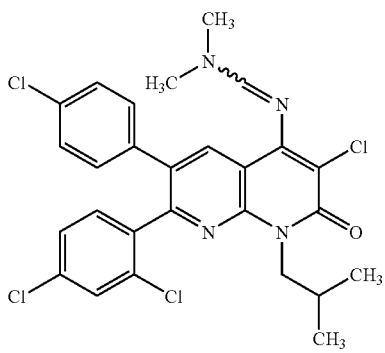

N'-[3-chloro-6-(4-chlorophenyl)-7-(2,4-dichlorophenyl)-1-isobutyl-2-oxo-1,2-dihydro-1,8-naphthyridin-4-yl]-N,N-dimethylimidoformamide The product of EXAMPLE 61 (50 mg) was combined with N,N-dimethylformamide dimethylacetal (4 mL). The reaction was heated to 95° C. and stirred for 90 minutes at which the solution was concentrated in vacuo. Purification by flash chromatography on silica eluted with 0-30% EtOAc in hexane afforded the title compound (E/Z mixture of isomers). HPLC/MS: 560.9 (M+1), 562.9 (M+3); $R_t$=4.48 min.

EXAMPLE 86

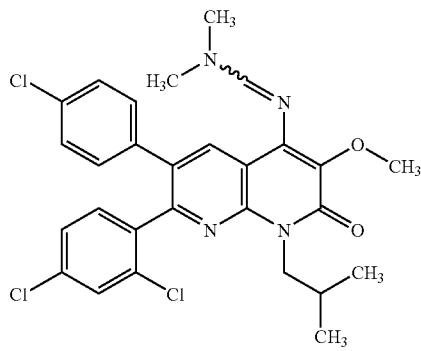

N'-[6-(4-chlorophenyl)-7-(2,4-dichlorophenyl)-1-isobutyl-3-methoxy-2-oxo-1,2-dihydro-1,8-naphthyridin-4-yl]-N,N-dimethylimidoformamide N-(6-(2,4-dichlorophenyl)-5-(4-chlorophenyl)-3-cyanopyridin-2-yl)-N-isobutyl-2-methoxyacetamide (prepared by the reaction of the product of Step A EXAMPLE 27 with 2-methoxyacetyl chloride using the conditions of EXAMPLE 62 Step A) was reacted with NaH using the conditions of EXAMPLE 80 affording 4-amino-7-(2,4-dichlorophenyl)-6-(4-chlorophenyl)-1-isobutyl-3-methoxy-1,8-naphthyridin-2(1H)-one which was treated to the conditions of EXAMPLE 85 to afford the title compound (E/Z mixture of isomers). HPLC/MS: 557.0 (M+1), 558.9 (M+3); $R_t$=3.70 min.

EXAMPLE 87

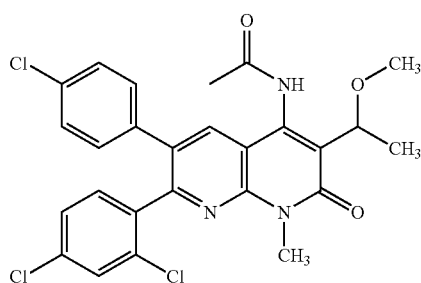

N-[6-(4-chlorophenyl)-7-(2,4-dichlorophenyl)-3-(1-methoxyethyl)-1-methyl-2-oxo-1,2-dihydro-1,8-naphthyridin-4-yl]acetamide The product of EXAMPLE 60 was treated to the conditions of EXAMPLE 64 and subsequently EXAMPLE 65 to afford the title compound. HPLC/MS: 529.9 (M+1), 531.9 (M+3); $R_t$=4.15 min.

EXAMPLE 88

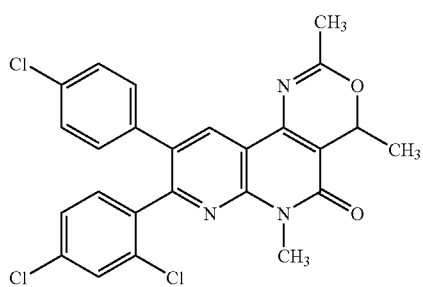

9-(4-chlorophenyl)-8-(2,4-dichlorophenyl)-2,4,6-trimethyl-4,6-dihydro-5H-[1,3]oxazino[5,4-c]-1,8-naphthyridin-5-one The title compound was isolated as a side product of EXAMPLE 60. HPLC/MS: 498.0 (M+1), 500.0 (M+3); $R_t$=4.83 min.

EXAMPLE 89

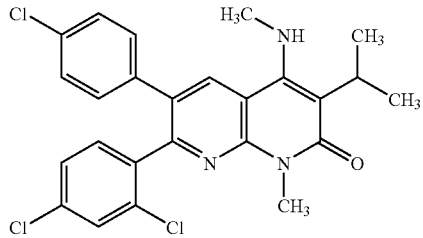

6-(4-chlorophenyl)-7-(2,4-dichlorophenyl)-3-isopropyl-1-methyl-4-(methylamino)-1,8-naphthyridin-2(1H)-one The product of EXAMPLE 54 (30 mg) in THF (2.5 mL) was combined with sodium hydride (5 mg, 60% in mineral oil). The suspension was stirred for 10 min were upon iodomethane (37 uL) was added. The reaction was stirred for about 6.5 hours at room temperature. The reaction mixture was quenched with saturated aqueous NaHCO$_3$ and diluted with EtOAc. The EtOAc solution was dried (Na$_2$SO$_4$). The concentrated residue was purified by preparative TLC on silica gel eluted with 35% EtOAc in hexane affording the title compound. HPLC/MS: 486.2 (M+1), 488.2 (M+3); $R_t$=4.72 min.

EXAMPLE 90

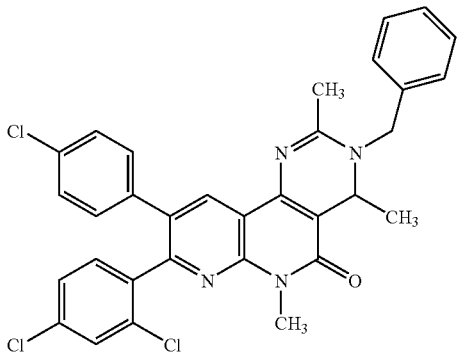

3-benzyl-9-(4-chlorophenyl)-8-(2,4-dichlorophenyl)-2,4,6-trimethyl-4,6-dihydropyrimido[5,4-c]-1,8-naphthyridin-5(3H)-one The product of Example 1 (80 mg) in 1,2-dichlorethane (1.5 mL) was combined with benzyl amine (16 μL), sodium triacetoxyborohydride (32 mg) and acetic acid (8.5 μL). The reaction was stirred for two days at room temperature. The reaction mixture was diluted with CH$_2$Cl$_2$ and washed with aqueous NaOH (1 M) and brine. The concentrated residue was purified by preparative TLC on silica gel eluted with 30% EtOAc in CH$_2$Cl$_2$ affording the title compound. HPLC/MS: 587.1 (M+1), 589.1 (M+3); $R_t$=3.86 min.

EXAMPLE 91

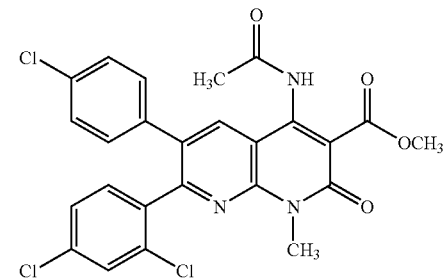

Methyl 4-(acetylamino)-6-(4-chlorophenyl)-7-(2,4-dichlorophenyl)-1-methyl-2-oxo-1,2-dihydro-1,8-naphthyridine-3-carboxylate Step A: Methyl 2-(N-(6-(2,4-dichlorophenyl)-5-(4-chlorophenyl)-3-cyanopyridin-2-yl)-N-methylcarbamoyl)acetate To the product of Step A Example 1 (1 g) in THF (7.5 mL) was added NaH (123.5 mg, 60% in mineral oil) followed by methyl 2-(chlorocarbonyl)acetate (0.414 mL) at 0° C. The reaction warmed to room temperature and stirred for about three hours. The reaction was diluted with EtOAc and washed with brine. The solution was dried (Na$_2$SO$_4$). The concentrated residue was purified by flash chromatography on silica gel gradient eluted with 0-45% EtOAc in hexane affording the title compound. HPLC/MS: 487.9 (M+1), 490.0 (M+3); R$_t$=4.27 min.

Step B: Methyl 4-(acetylamino)-6(4-chlorophenyl)-7-(2,4-dichlorophenyl)-1-methyl-2-oxo-1,2-dihydro-1,8-naphthyridine-3-carboxylate The product of step A was treated to the conditions of Step E Example 1 to afford the title compound. HPLC/MS: 530.0 (M+1), 532.0 (M+3); R$_t$=3.76 min.

EXAMPLE 92

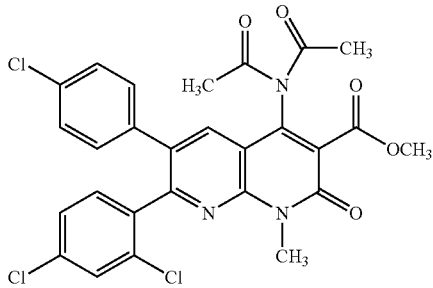

Methyl 4-(N-acetylacetamido)-7-(2,4-dichlorophenyl)-6-(4-chlorophenyl)-1,2-dihydro-1-methyl-2-oxo 1,8-naphthyridine-3-carboxylate The title compound was isolated as a side product of EXAMPLE 91. HPLC/MS: 572.0 (M+1), 574.0 (M+3); R$_t$=4.12 min.

EXAMPLE 93

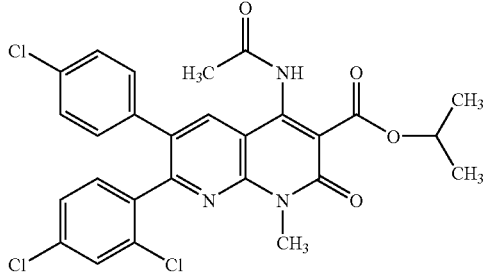

Isopropyl 4-(acetylamino)-6-(4-chlorophenyl)-7-(2,4-dichlorophenyl)-1-methyl-2-oxo-1,2-dihydro-1,8-naphthyridine-3-carboxylate To the product of EXAMPLE 91 (10 mg) in isopropanol (4 mL) and THF (1 mL) was added Cs$_2$CO$_3$ (10 mg). The reaction stirred for about 14 hours at 50° C. LC/MS indicated incomplete reaction and the solution was then heated to 90° C. in a pressure tube for three hours. The reaction was concentrated and then diluted with EtOAc. After washing with saturated aqueous NaHCO$_3$ the solution was dried (Na$_2$SO$_4$). The concentrated residue was purified by preparative TLC on silica gel eluted with 5% methanol in CH$_2$Cl$_2$ affording the title compound. HPLC/MS: 558.0 (M+1), 560.0 (M+3); R$_t$=4.93 min.

EXAMPLE 94

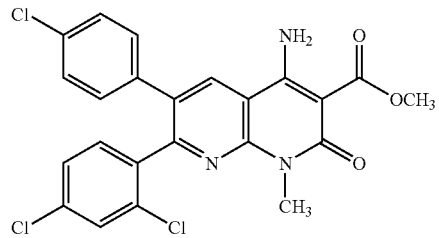

methyl 4-amino-6-(4-chlorophenyl)-7-(2,4-dichlorophenyl)-1-methyl-2-oxo-1,2-dihydro-1,8-naphthyridine-3-carboxylate To the product of Step A EXAMPLE 91 (100 mg) in THF (1 mL) was added 2 mL of NH$_3$ in methanol (7 M). The reaction stirred for 3.5 hours at room temperature before it was concentrated. The residue was dissolved in CH$_2$Cl$_2$ and washed with saturated aqueous NaHCO$_3$. The solution was dried (Na$_2$SO$_4$) and concentrated to afford the title compound. HPLC/MS: 488.0 (M+1), 490.0 (M+3); R$_t$=4.05 min.

EXAMPLE 95

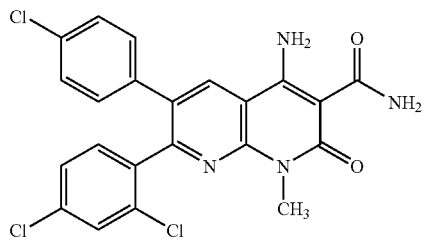

4-amino-6-(4-chlorophenyl)-7-(2,4-dichlorophenyl)-1-methyl-2-oxo-1,2-dihydro-1,8-naphthyridine-3-carboxamide To the product of EXAMPLE 91 (30 mg) in THF (1 mL) was added 3 mL of NH$_3$ in methanol (7 M). The reaction stirred for about 15 hours at room temperature before it was concentrated. The residue was dissolved in CH$_2$Cl$_2$ and washed with water. The solution was dried (Na$_2$SO$_4$) and concentrated. The concentrated residue was purified by preparative TLC on silica gel eluted with 100% EtOAc affording the title compound. HPLC/MS: 473.0 (M+1), 475.0 (M+3); R$_t$=4.19 min.

EXAMPLE 96

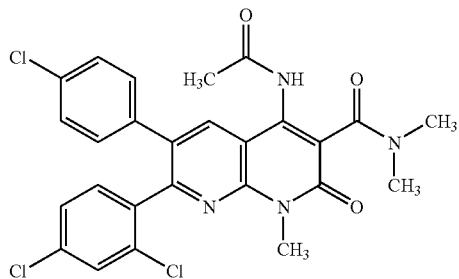

4-(acetylamino)-6-(4-chlorophenyl)-7-(2,4-dichlorophenyl)-N,N,1-trimethyl-2-oxo-1,2-dihydro-1,8-naphthyridine-3-carboxamide To dimethylamine hydrochloride (26.1 mg) in toluene (2 mL) was added Al(CH$_3$)$_3$ (0.16 mL) at 0° C. The reaction stirred for about 30 minutes before adding the product of EXAMPLE 91 (85 mg) in toluene (1 mL). The reaction stirred for 3.5 hours at 50° C. and was quenched with aqueous 1 M HCl. The reaction was diluted with EtOAc washed with aqueous 1 M HCl. The solution was dried (Na$_2$SO$_4$) and concentrated. The concentrated residue was purified by preparative TLC on silica gel eluted with 6% methanol in CH$_2$Cl$_2$ affording the title compound. HPLC/MS: 543.0 (M+1), 545.0 (M+3); R$_t$=3.51 min.

EXAMPLE 97

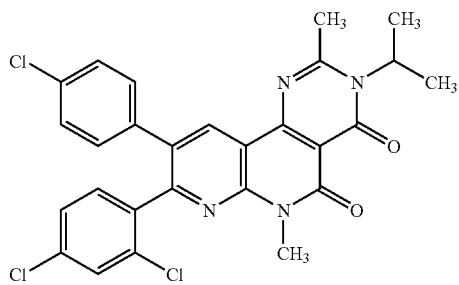

9-(4-chlorophenyl)-8-(2,4-dichlorophenyl)-3-isopropyl-2,6-dimethylpyrimido[5,4-c]-1,8-naphthyridine-4,5(3H,6H)-dione To isopropylamine (27.3 µL) in toluene (0.75 mL) was added Al(CH$_3$)$_3$ (0.16 mL) at 0° C. The reaction stirred for about 15 minutes before adding the product of EXAMPLE 91 (85 mg) in toluene (1 mL). The reaction stirred for 3.5 hours at 50° C. and was quenched with aqueous 1 M HCl. The reaction was diluted with EtOAc washed with aqueous 1 M HCl. The solution was dried (Na$_2$SO$_4$) and concentrated. The concentrated residue was purified by preparative TLC on silica gel eluted with 8% methanol in CH$_2$Cl$_2$ affording the title compound. HPLC/MS: 539.0541.0 (M+1), 545.0 (M+3); R$_t$=4.47 min.

EXAMPLE 98

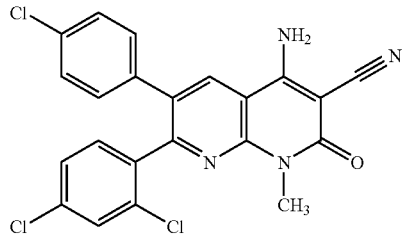

4-amino-6-(4-chlorophenyl)-7-(2,4-dichlorophenyl)-1-methyl-2-oxo-1,2-dihydro-1,8-naphthyridine-3-carbonitrile To the product of Step A EXAMPLE 62 (80 mg) in DMF (4 mL) was added NaCN (84 mg) and tetrabutylammonium bromide (55.4 mg). The reaction stirred for 1 hour at room temperature before it was diluted with EtOAc. The solution was washed with saturated aqueous NaHCO$_3$ and brine. The solution was dried (Na$_2$SO$_4$) and concentrated. The residue was purified by flash chromatography on silica gel gradient eluted with 0-100% EtOAc in hexane affording the title compound. HPLC/MS: 455.0 (M+1), 457.0 (M+3); R$_t$=4.00 min.

EXAMPLE 99

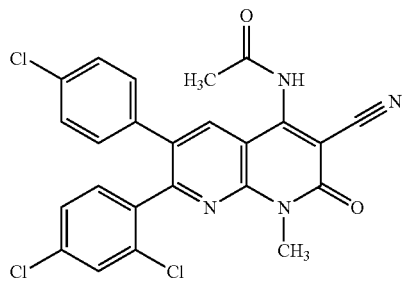

N-[6-(4-chlorophenyl)-3-cyano-7-(2,4-dichlorophenyl)-1-methyl-2-oxo-1,2-dihydro-1,8-naphthyridin-4-yl]acetamide To the product of EXAMPLE 98 (43 mg) in DMF (0.5 mL) and THF (1 mL) was added acetyl chloride (65 µL) and triethylamine (0.13 mL). The reaction stirred about 4 hours at room temperature before it was diluted with EtOAc. The solution was washed with saturated aqueous NaHCO$_3$ and brine. The solution was dried (Na$_2$SO$_4$) and concentrated. The residue was purified by flash chromatography on silica gel gradient eluted with 0-85% EtOAc in hexane affording N-acetyl-N-(7-(2,4-dichlorophenyl)-6-(4-chlorophenyl)-3-cyano-1,2-dihydro-1-methyl-2-oxo-1,8-naphthyridin-4-yl) acetamide which was subjected to the conditions of EXAMPLE 65 to afford the title compound. HPLC/MS: 496.8 (M+1), 498.8 (M+3); R$_t$=3.94 min.

BIOLOGICAL EXAMPLE 1

Cannabinoid Receptor-1 (CB 1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μL (240 μL CB1 receptor membrane solution plus 5 μL test compound solution plus 5 μL [3H]CP-55940 solution). Final concentration of [3H]CP-55940 is 0.6 nM. Binding buffer contains 50 mM Tris-HCl, pH7.4, 2.5 mM EDTA, 5 mM $MgCl_2$, 0.5 mg/mL fatty acid free bovine serum albumin and protease inhibitors (Cat#P8340, from Sigma). To initiate the binding reaction, 5 μL of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from $IC_{50}$ values (DeBlasi et al., Trends Pharmacol Sci 10: 227-229, 1989).

The binding assay for CB2 receptor is done similarly with recombinant human CB2 receptor expressed in CHO cells.

CB1 antagonist/inverse agonist compounds of the present invention have $IC_{50}$s of less than 1 micromolar in the CB1 binding assay. Selective CB1 antagonist/inverse agonist compounds have IC50s 100-fold greater in the CB2 binding assay than in the CB1 assay, and generally have IC50s of greater than one micromolar in the CB2 binding assay.

BIOLOGICAL EXAMPLE 2

Cannabinoid Receptor-1 (CB1) Functional Activity Assay.

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 μL of CB1-CHO cell suspension are mixed with test compound and 70 uL assay buffer containing 0.34 mM 3-isobutyl-1-methylxanthine and 5.1 μM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 30 μl/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

CB1 antagonist/inverse agonist compounds of the present invention generally have EC50s of less than 10 micromolar in the CB1 functional assay and preferred CB1 antagonist/inverse agonist compound of the present invention generally have EC50s of less than 1 micromolar in the CB1 functional assay. Preferred selective CB1 antagonist/inverse agonists have generally have EC50s of greater than 1 micromolar in the CB2 functional assay.

BIOLOGICAL EXAMPLE 3

Acute Food Intake Studies in Rats or Mice: General Procedure

Adult rats or mice are used in these studies. After at least 2 days of acclimation to the vivarium conditions (controlled humidity and temperature, lights on for 12 hours out of 24 hours) food is removed from rodent cages. Experimental compounds or their vehicles are administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the compounds are compared to the effect of vehicle. In these experiments many strains of mouse or rat, and several standard rodent chows can be used.

BIOLOGICAL EXAMPLE 4

Chronic Weight Reduction Studies in Rats or Mice: General Procedure

Adult rats or mice are used in these studies. Upon or soon after weaning, rats or mice are made obese due to exclusive access to diets containing fat and sucrose in higher proportions than in the control diet. The rat strains commonly used include the Sprague Dawley bred through Charles River Laboratories. Although several mouse strains may be used, c57B1/6 mice are more prone to obesity and hyperinsulinemia than other strains. Common diets used to induce obesity include: Research Diets D12266B (32% fat) or D12451 (45% fat) and BioServ S3282 (60% fat). The rodents ingest chow until they are significantly heavier and have a higher proportion of body fat than control diet rats, often 9 weeks. The rodents receive injections (1 to 4 per day) or continuous infusions of experimental compounds or their vehicles either orally, intraperitoneally, subcutaneously or intravenously. Food intake and body weights are measured daily or more frequently. Food intake is calculated as grams of food eaten per gram of body weight within each time interval and the appetite-suppressant and weight loss effects of the compounds are compared to the effects of vehicle.

BIOLOGICAL EXAMPLE 5

Tail Suspension Test

The tail suspension test has been widely used for screening antidepressant-like effects of compounds in mice (Steru et al., 1987), rats (Izumi et al, 1997) and gerbils (Varty et al., 2003). It is based on the principle that helplessness takes place when the animal is exposed to a sustained aversive situation. Briefly, when the animal is suspended by its tail it exhibits several escape-oriented behaviors intercalated with bouts of immobility that evolve with time into complete immobility. Pretreatment with a wide range of antidepressants, such as tricyclic compounds, monoamine uptake blockers, or serotonin reuptake inhibitors (SSRIs), significantly decrease duration of immobility throughout the test, while anxiolytics or antipsychotics do not (Wong et al., 2000; Oxenkrug 1999).

Subjects

Male mice are housed in a colony room maintained at constant temperature (22° C.) and humidity (30-70%), with food (Harlan Teklad Diet #7012, 5% fat; 3.75 kcal/gm) and water available ad libitum. For the behavioral experiments, mice are group housed (10/cage) under a reversed light/dark cycle (lights on at 21:00 h, off at 09:00 h) and tests occurred between 10:00 h and 14:00 h.

Drugs

The compounds of formula (I) are solubilized into 1% Tween80-saline solution, addition of DMSO may be employed to increase solubility. Compounds are dosed intraperitonieally in a volume of 0.1 mL.

Tail Suspension Test

An automated tail-suspension apparatus (TSE Systems, Bad Homburg, Germany) with a tail hanger connected to a precision linear load cell is used. One centimeter of the mouse's tail is inserted into the tail hanger and secured with non-irritating adhesive tape. Mice are suspended by the tail, at a height of 35 cm from the tabletop for 6 minutes. During this time the load cell records the mouse's movements and transmits the information to a central computer, which then records the rate of immobility within the course of the session, and calculates total duration of immobility.

Total duration of immobility is used as the dependent variable in one-way Analysis of Variance (ANOVA) on treatment.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

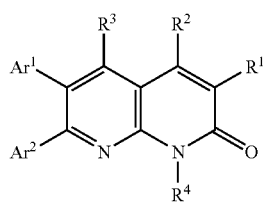

(I)

and pharmaceutically acceptable salts thereof, wherein:
$R^1$ is selected from:
(1) hydrogen,
(2) halogen,
(3) $C_{1-4}$alkyl,
(4) —CN,
(5) —C(O)$R^7$,
(6) —O$R^d$,
(7) —N$R^5R^6$, and
(8) pyrrolidinyl,
wherein: alkyl moieties are unsubstituted or substituted with one substituent independently selected from $R^a$;
$R^2$ is selected from: —N$R^5R^6$, and $C_{1-6}$alkyl;
$R^3$ is hydrogen;
$R^4$ is selected from:
(1) hydrogen, and
(2) —CH$_2$—$R^8$;
$R^5$ is selected from:
(1) hydrogen,
(2) $C_{1-6}$alkyl,
(3) trifluoromethyl, and
(4) methylcarbonyl,
$R^6$ is each selected from:
(1) hydrogen,
(2) $C_{1-6}$alkyl,
(3) phenyl,
(4) benzyl,
(5) trifluoromethyl,
(6) —C(O)—$R^c$,
(7) —CO$_2R^c$, and
(8) —S(O)$_2$CH$_3$,
or $R^5$ and $R^6$ together form =CH—N(CH$_3$)$_2$;
$R^7$ is selected from:
(1) hydrogen,
(2) $C_{1-3}$alkyl,
(3) —O$R^e$, and
(4) —N$R^dR^e$,
wherein the alkyl moieties are unsubstituted or substituted with one, two, or three substituents independently selected from $R^a$;
$R^8$ is selected from:
(1) hydrogen,
(2) —(CH$_2$)$_n$OC(O)CH$_3$,
(3) $C_{1-6}$alkyl,
(4) $C_{3-6}$cycloalkyl,
(5) tetrahydrofuranyl,
(6) phenyl, and
(7) pyridyl;
wherein the alkyl moieties are unsubstituted or substituted with one substituent independently selected from —O$R^e$, and the tetrahydrofuranyl, phenyl, and pyridyl moieties are unsubstituted or substituted with one, or two substituents independently selected from O$R^e$, halogen, —N$R^eR^f$, —COCH$_3$, —C(O)OCH$_3$, —CN, and $C_{1-3}$ alkyl;
$Ar^1$ and $Ar^2$ are each phenyl, unsubstituted or substituted with one or two substituents independently selected from $R^b$;
each $R^a$ is independently selected from: —O$R^e$, halogen, —N$R^eR^f$, —C(O)$R^c$, —CO$_2R^c$, —OC(O)$R^c$, —CN, CF$_3$, and —OCF$_3$;
each $R^b$ is independently selected from:
(1) $R^a$, and
(2) $C_{1-10}$alkyl;
each $R^c$ is independently selected from: hydrogen, $C_{1-6}$alkyl, and —N$R^dR^d$; wherein each alkyl moiety may be substituted with one or two substituents selected from $R^h$ and oxo;
each $R^d$ is independently selected from hydrogen, and $C_{1-6}$alkyl;
$R^e$ and $R^f$ are is independently selected from hydrogen and $C_{1-3}$alkyl;
each $R^h$ is independently selected from:
(1) halogen,
(2) $C_{1-10}$alkyl, (3) —OR$^i$,
(4) —NR$^i$R$^i$, and
(5) —OC(O)R$^i$,
each R$^i$ is independently selected from:
(1) hydrogen,
(2) C$_{1-3}$alkyl,
(3) trifluoromethyl, and
(4) cyclopropyl;
wherein each alkyl and cycloalkyl moiety is unsubstituted or substituted with one substituent selected from oxo, hydroxy, methoxy, acetoxy, halogen, cyano, and trifluoromethyl;
and
n is 1;
or a pharmaceutically acceptable salt thereof.

2. The compound according to claim 1, wherein;
each R$^a$ is independently selected from: hydroxy, methoxy-, halogen, methylcarbonyl-, —CO$_2$R$^c$, —OC(O)R$^c$, —CN, CF$_3$, and —OCF$_3$;
each R$^d$ is independently selected from hydrogen, methyl, and ethyl;
each R$^h$ is independently selected from:
(1) halogen;
(2) C$_{1-3}$alkyl;
(3) hydroxy;
(4) methoxy-; and
(5) —NR$^i$R$^i$,
wherein R$^i$ is selected from hydrogen and methyl; methylcarbonyloxy- ; —CF$_3$; and —OCF$_3$;
or a pharmaceutically acceptable salt thereof.

3. The compound according to claim 2, wherein R$^1$ is selected from:
(1) halogen;
(2) C$_{1-3}$alkyl, unsubstituted or substituted with hydroxy or methoxy;
(3) —CN;
(4) methyloxycarbonyl-;
(5) methylcarbonyl-;
(6) isopropyloxycarbonyl-;
(7) bromomethylcarbonyl-;
(8) —C(O)NH$_2$;
(9) methoxy-; and
(10) —NR$^5$R$^6$, wherein R$^5$ is methyl and R$^6$ is C$_{1-3}$alkyl;
each R$^i$ is independently selected from: hydrogen, and methyl;
and pharmaceutically acceptable salts thereof.

4. The compound according to claim 2, wherein R$^5$ is selected from: hydrogen, methyl, and methlcarbonyl-, and
R$^6$ is hydrogen, C$_{1-3}$alkyl, methyl benzyl, —C(=O)R$^c$, or —SO$_2$CH$_3$;
R$^7$ is selected from:
(1) C$_{1-3}$alkyl, unsubstituted or substituted with halogen;
(2) —OR$^e$; and
(3) —NR$^d$R$^e$;
wherein R$^d$ is selected from hydrogen and methyl, and R$^e$ is selected from hydrogen and C$_{1-3}$alkyl;
and pharmaceutically acceptable salts thereof.

5. The compound according to claim 4, wherein:
R$^1$ is selected from:
(1) —C(O)CH$_3$,
(2) —CH(OH)CH$_3$,
(3) —CH$_3$,
(4) —CH$_2$CH$_3$,
(5) —CH(CH$_3$)$_2$,
(6) —CH(OCH$_3$)(CH$_3$),
(7) —C(O)—OCH$_3$,
(8) —C(O)OCH(CH$_3$)$_2$,
(9) —CN, —C(O)NH$_2$,
(10) —C(O)N(CH$_3$)$_2$,—
(11) Cl
(12) —N(CH$_3$)$_2$,
(13) —N(CH$_3$)(CH(CH$_3$)$_2$), and
(14) pyrrolidinyl;
R$^2$ is or C$_{1-6}$alkyl or NR$^5$R$^6$, wherein R$^5$ is selected from: hydrogen, methyl, and methylcarbonyl-, and R$^6$ is selected from, hydrogen, methyl benzyl, —C(=O)R$^c$, and —SO$_2$CH$_3$;
R$^5$ is selected from: hydrogen, methyl, and methlcarbonyl-, and
R$^6$ is hydrogen, C$_{1-3}$alkyl, methyl benzyl, or —C(=O)R$^c$;
Ar$^1$ is phenyl, substituted with one or two substituents independently selected from halogen and methyl;
Ar$^2$ is phenyl, either unsubstituted or substituted with one or two halogen substituents;
or a pharmaceutically acceptable salt thereof.

6. The compound according to claim 1, of structural formula IA:

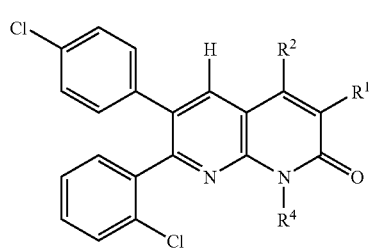

IA wherein R$^1$, R$^2$, and R$^4$ are as defined in claim 1;
and pharmaceutically acceptable salts thereof.

7. A compound selected from:
N-[3-acetyl-6-(4-chlorophenyl)-7-(2,4-dichlorophenyl)-1-methyl-2-oxo-1,2-dihydro-1,8-naphthyridin-4-yl]acetamide;
3-acetyl-4-amino-6-(4-chlorophenyl)-7-(2,4-dichlorophenyl)-1-methyl-1,8-naphthyridin-2(1H)-one;
N-[6-(4-chlorophenyl)-7-(2,4-dichlorophenyl)-3-(1-hydroxyethyl)-1-methyl-2-oxo-1,2-dihydro-1,8-naphthyridin-4-yl]acetamide;
4-amino-6-(4-chlorophenyl)-7-(2,4-dichlorophenyl)-1-methyl-1,8-naphthyridin-2(1H)-one;
N-[6-(4-chlorophenyl)-7-(2,4-dichlorophenyl)-1-methyl-2-oxo-1,2-dihydro-1,8-naphthyridin-4-yl]acetamide;
N-[3-acetyl-6-(4-chlorophenyl)-7-(2,4-dichlorophenyl)-1-ethyl-2-oxo-1,2-dihydro-1,8-naphthyridin-4-yl]acetamide;
3-acetyl-4-(benzylamino)-6-(4-chlorophenyl)-7-(2,4-dichlorophenyl)-1-methyl-1,8-naphthyridin-2(1H)-one;
3-acetyl-6-(4-chlorophenyl)-7-(2,4-dichlorophenyl)-4-(dimethylamino)-1-methyl-1,8-naphthyridin-2(1H)-one;
N'-[3-acetyl-6-(4-chlorophenyl)-7-(2,4-dichlorophenyl)-1-methyl-2-oxo-1,2-dihydro-1,8-naphthyridin-4-yl]-N,N-dimethylurea;
N-[3-acetyl-6-(4-chlorophenyl)-7-(2,4-dichlorophenyl)-1-methyl-2-oxo-1,2-dihydro-1,8-naphthyridin-4-yl]-N-methylacetamide;
N-[3-acetyl-6-(4-chlorophenyl)-7-(2,4-dichlorophenyl)-1-methyl-2-oxo-1,2-dihydro-1,8-naphthyridin-4-yl]-2-methoxyacetamide;

N-[3-acetyl-1-benzyl-6-(4-chlorophenyl)-7-(2,4-dichlorophenyl)-2-oxo-1,2-dihydro-1,8-naphthyridin-4-yl]acetamide;

N-[3-acetyl-6-(4-chlorophenyl)-1-(cyclopropylmethyl)-7-(2,4-dichlorophenyl)-2-oxo-1,2-dihydro-1,8-naphthyridin-4-yl]acetamide;

N-[3-acetyl-1-butyl-6-(4-chlorophenyl)-7-(2,4-dichlorophenyl)-2-oxo-1,2-dihydro-1,8-naphthyridin-4-yl]acetamide;

N-[3-acetyl-6-(4-chlorophenyl)-7-(2,4-dichlorophenyl)-1-isobutyl-2-oxo-1,2-dihydro-1,8-naphthyridin-4-yl]acetamide;

N-[3-acetyl-6-(4-chlorophenyl)-7-(2,4-dichlorophenyl)-1-(2-methoxyethyl)-2-oxo-1,2-dihydro-1,8-naphthyridin-4-yl]acetamide;

N-[3-acetyl-6-(4-chlorophenyl)-7-(2,4-dichlorophenyl)-2-oxo-1-(tetrahydrofuran-2-ylmethyl)-1,2-dihydro-1,8-naphthyridin-4-yl]acetamide;

2-{[3-acetyl-4-(acetylamino)-6-(4-chlorophenyl)-7-(2,4-dichlorophenyl)-2-oxo-1,8-naphthyridin-1(2H)-yl]methyl}pyridinium trifluoroacetate;

3-{[3-acetyl-4-(acetylamino)-6-(4-chlorophenyl)-7-(2,4-dichlorophenyl)-2-oxo-1,8-naphthyridin-1(2H)-yl]methyl}pyridinium trifluoroacetate;

2-[3-acetyl-4-(acetylamino)-6-(4-chlorophenyl)-7-(2,4-dichlorophenyl)-2-oxo-1,8-naphthyridin-1(2H)-yl]ethyl acetate;

N-[3-acetyl-6-(4-chlorophenyl)-7-(2,4-dichlorophenyl)-1-(2,4-dimethoxybenzyl)-2-oxo-1,2-dihydro-1,8-naphthyridin-4-yl]acetamide;

4-{[3-acetyl-4-(acetylamino)-6-(4-chlorophenyl)-7-(2,4-dichlorophenyl)-2-oxo-1,8-naphthyridin-1(2H)-yl]methyl}pyridinium trifluoroacetate;

N-[3-acetyl-6-(4-chlorophenyl)-7-(2,4-dichlorophenyl)-2-oxo-1-propyl-1,2-dihydro-1,8-naphthyridin-4-yl]acetamide;

N-[3-acetyl-7-(2-chlorophenyl)-6-(4-chlorophenyl)-1-methyl-2-oxo-1,2-dihydro-1,8-naphthyridin-4-yl]acetamide;

N-[3-acetyl-7-(2-chlorophenyl)-6-(4-chlorophenyl)-1-isobutyl-2-oxo-1,2-dihydro-1,8-naphthyridin-4-yl]acetamide;

N-(1-(2,4-dimethoxybenzyl)-3-acetyl-7-(2,4-dichlorophenyl)-6-(4-chlorophenyl)-1,2-dihydro-2-oxo-1,8-naphthyridin-4-yl)-N-acetylacetamide;

N-(1-(2,4-dimethoxybenzyl)-7-(2,4-dichlorophenyl)-6-(4-chlorophenyl)-1,2-dihydro-2-oxo-1,8-naphthyridin-4-yl)-N-acetylacetamide;

N-[3-acetyl-6-(4-chlorophenyl)-7-(2,4-dichlorophenyl)-2-oxo-1,2-dihydro-1,8-naphthyridin-4-yl]acetamide;

N-[3-acetyl-6-(4-chlorophenyl)-7-(2,4-dichlorophenyl)-1-(2-hydroxyethyl)-2-oxo-1,2-dihydro-1,8-naphthyridin-4-yl]acetamide;

N-[3-acetyl-6-(4-chlorophenyl)-7-(2,4-dichlorophenyl)-1-methyl-2-oxo-1,2-dihydro-1,8-naphthyridin-4-yl]methanesulfonamide;

2-{[3-acetyl-6-(4-chlorophenyl)-7-(2,4-dichlorophenyl)-1-methyl-2-oxo-1,2-dihydro-1,8-naphthyridin-4-yl]amino}-2-oxoethyl acetate;

N-[3-acetyl-6-(4-chlorophenyl)-7-(2,4-dichlorophenyl)-1-methyl-2-oxo-1,2-dihydro-1,8-naphthyridin-4-yl]-2-hydroxyacetamide;

N-[3-acetyl-7-(2,4-dichlorophenyl)-1-methyl-6-(4-methylphenyl)-2-oxo-1,2-dihydro-1,8-naphthyridin-4-yl]acetamide;

N-[3-acetyl-7-(4-chlorophenyl)-6-(2,4-dichlorophenyl)-1-methyl-2-oxo-1,2-dihydro-1,8-naphthyridin-4-yl]acetamide;

N-[6-(4-chlorophenyl)-7-(2,4-dichlorophenyl)-1,3-dimethyl-2-oxo-1,2-dihydro-1,8-naphthyridin-4-yl]propanamide;

N-[6-(4-chlorophenyl)-7-(2,4-dichlorophenyl)-3-ethyl-1-methyl-2-oxo-1,2-dihydro-1,8-naphthyridin-4-yl]butanamide;

4-amino-6-(4-chlorophenyl)-7-(2,4-dichlorophenyl)-1,3-dimethyl-1,8-naphthyridin-2(1H)-one;

N-[6-(4-chlorophenyl)-7-(2,4-dichlorophenyl)-1,3-dimethyl-2-oxo-1,2-dihydro-1,8-naphthyridin-4-yl]acetamide;

4-amino-6-(4-chlorophenyl)-7-(2,4-dichlorophenyl)-1-isobutyl-3-methyl-1,8-naphthyridin-2(1H)-one;

N-[6-(4-chlorophenyl)-7-(2,4-dichlorophenyl)-1-isobutyl-3-methyl-2-oxo-1,2-dihydro-1,8-naphthyridin-4-yl]acetamide;

N-[6-(4-chlorophenyl)-7-(2,4-dichlorophenyl)-1-isobutyl-3-methyl-2-oxo-1,2-dihydro-1,8-naphthyridin-4-yl]-N-methylacetamide;

2-{[6-(4-chlorophenyl)-7-(2,4-dichlorophenyl)-1-isobutyl-3-methyl-2-oxo-1,2-dihydro-1,8-naphthyridin-4-yl]amino}-2-oxoethyl acetate;

2-chloro-N-[6-(4-chlorophenyl)-7-(2,4-dichlorophenyl)-1-isobutyl-3-methyl-2-oxo-1,2-dihydro-1,8-naphthyridin-4-yl]acetamide;

N-[6-(4-chlorophenyl)-7-(2,4-dichlorophenyl)-1-isobutyl-3-methyl-2-oxo-1,2-dihydro-1,8-naphthyridin-4-yl]-2-methoxyacetamide;

N-[6-(4-chlorophenyl)-7-(2,4-dichlorophenyl)-1-isobutyl-3-methyl-2-oxo-1,2-dihydro-1,8-naphthyridin-4-yl]-N'-ethylurea;

N-[3-chloro-6-(4-chlorophenyl)-7-(2,4-dichlorophenyl)-1-isobutyl-2-oxo-1,2-dihydro-1,8-naphthyridin-4-yl]-2-hydroxyacetamide;

$N^1$-[6-(4-chlorophenyl)-7-(2,4-dichlorophenyl)-1-isobutyl-3-methyl-2-oxo-1,2-dihydro-1,8-naphthyridin-4-yl]-$N^2,N^2$-dimethylglycinamide;

$N^1$-[6-(4-chlorophenyl)-7-(2,4-dichlorophenyl)-1-isobutyl-3-methyl-2-oxo-1,2-dihydro-1,8-naphthyridin-4-yl]-$N^2$-methylglycinamide;

$N^1$-[6-(4-chlorophenyl)-7-(2,4-dichlorophenyl)-1-isobutyl-3-methyl-2-oxo-1,2-dihydro-1,8-naphthyridin-4-yl]glycinamide;

4-amino-6-(4-chlorophenyl)-7-(2,4-dichlorophenyl)-3-ethyl-1-methyl-1,8-naphthyridin-2(1H)-one;

4-amino-6-(4-chlorophenyl)-7-(2,4-dichlorophenyl)-3-isopropyl-1-methyl-1,8-naphthyridin-2(1H)-one;

4-amino-6-(4-chlorophenyl)-7-(2,4-dichlorophenyl)-3-methyl-1-propyl-1,8-naphthyridin-2(1H)-one;

N-[6-(4-chlorophenyl)-7-(2,4-dichlorophenyl)-3-ethyl-1-methyl-2-oxo-1,2-dihydro-1,8-naphthyridin-4-yl]acetamide;

N-[6-(4-chlorophenyl)-7-(2,4-dichlorophenyl)-3-isopropyl-1-methyl-2-oxo-1,2-dihydro-1,8-naphthyridin-4-yl]acetamide;

N-[6-(4-chlorophenyl)-7-(2,4-dichlorophenyl)-3-methyl-2-oxo-1-propyl-1,2-dihydro-1,8-naphthyridin-4-yl]acetamide;

N-[6-(4-chlorophenyl)-7-(2,4-dichlorophenyl)-3-ethyl-1-isobutyl-2-oxo-1,2-dihydro-1,8-naphthyridin-4-yl]acetamide;

4-amino-6-(4-chlorophenyl)-7-(2,4-dichlorophenyl)-3-(1-methoxyethyl)-1-methyl-1,8-naphthyridin-2(1H)-one;

4-amino-3-chloro-6-(4-chlorophenyl)-7-(2,4-dichlorophenyl)-1-isobutyl-1,8-naphthyridin-2(1H)-one;

N-[3-chloro-6-(4-chlorophenyl)-7-(2,4-dichlorophenyl)-1-methyl-2-oxo-1,2-dihydro-1,8-naphthyridin-4-yl]acetamide;

4-amino-3-chloro-6-(4-chlorophenyl)-7-(2,4-dichlorophenyl)-1-methyl-1,8-naphthyridin-2(1H)-one;

N-acetyl-N-(3-chloro-7-(2,4-dichlorophenyl)-6-(4-chlorophenyl)-1,2-dihydro-1-isobutyl-2-oxo-1,8-naphthyridin-4-yl)acetamide;

N-[3-chloro-6-(4-chlorophenyl)-7-(2,4-dichlorophenyl)-1-isobutyl-2-oxo-1,2-dihydro-1,8-naphthyridin-4-yl]acetamide;

$N^1$-[3-chloro-6-(4-chlorophenyl)-7-(2,4-dichlorophenyl)-1-isobutyl-2-oxo-1,2-dihydro-1,8-naphthyridin-4-yl]-$N^2,N^2$-dimethylglycinamide;

2-{[3-chloro-6-(4-chlorophenyl)-7-(2,4-dichlorophenyl)-1-isobutyl-2-oxo-1,2-dihydro-1,8-naphthyridin-4-yl]amino}-2-oxoethyl acetate;

N-[3-chloro-6-(4-chlorophenyl)-7-(2,4-dichlorophenyl)-1-isobutyl-2-oxo-1,2-dihydro-1,8-naphthyridin-4-yl]-2-hydroxyacetamide;

N-acetyl-N-(3-chloro-7-(2-chlorophenyl)-6-(4-chlorophenyl)-1,2-dihydro-1-isobutyl-2-oxo-1,8-naphthyridin-4-yl)acetamide;

N-[3-chloro-7-(2-chlorophenyl)-6-(4-chlorophenyl)-1-isobutyl-2-oxo-1,2-dihydro-1,8-naphthyridin-4-yl]acetamide;

N-[3-chloro-7-(2-chloro-4-fluorophenyl)-6-(4-chlorophenyl)-1-isobutyl-2-oxo-1,2-dihydro-1,8-naphthyridin-4-yl]acetamide;

4-amino-6-(4-chlorophenyl)-7-(2,4-dichlorophenyl)-3-(dimethylamino)-1-methyl-1,8-naphthyridin-2(1H)-one;

N-acetyl-N-(7-(2,4-dichlorophenyl)-6-(4-chlorophenyl)-3-(dimethylamino)-1,2-dihydro-1-methyl-2-oxo-1,8-naphthyridin-4-yl)acetamide;

N-[6-(4-chlorophenyl)-7-(2,4-dichlorophenyl)-3-(dimethylamino)-1-methyl-2-oxo-1,2-dihydro-1,8-naphthyridin-4-yl]acetamide;

4-amino-6-(4-chlorophenyl)-7-(2,4-dichlorophenyl)-3-[isopropyl(methyl)amino]-1-methyl-1,8-naphthyridin-2(1H)-one;

N-(3-(N-isopropyl-N-methylamino)-7-(2,4-dichlorophenyl)-6-(4-chlorophenyl)-1,2-dihydro-1-methyl-2-oxo-1,8-naphthyridin-4-yl)-N-acetylacetamide;

N-{6-(4-chlorophenyl)-7-(2,4-dichlorophenyl)-3-[isopropyl(methyl)amino]-1-methyl-2-oxo-1,2-dihydro-1,8-naphthyridin-4-yl}acetamide;

N-acetyl-N-(7-(2,4-dichlorophenyl)-6-(4-chlorophenyl)-1,2-dihydro-1-methyl-2-oxo-3-(pyrrolidin-1-yl)-1,8-naphthyridin-4-yl)acetamide;

N-[6-(4-chlorophenyl)-7-(2,4-dichlorophenyl)-1-methyl-2-oxo-3-pyrrolidin-1-yl-1,2-dihydro-1,8-naphthyridin-4-yl]acetamide;

N-[6-(4-chlorophenyl)-7-(2,4-dichlorophenyl)-3-methoxy-1-methyl-2-oxo-1,2-dihydro-1,8-naphthyridin-4-yl]acetamide;

N-acetyl-N-(7-(2,4-dichlorophenyl)-6-(4-chlorophenyl)-1,2-dihydro-1-isobutyl-3-methoxy-2-oxo-1,8-naphthyridin-4-yl)acetamide;

N-[6-(4-chlorophenyl)-7-(2,4-dichlorophenyl)-1-isobutyl-3-methoxy-2-oxo-1,2-dihydro-1,8-naphthyridin-4-yl]acetamide;

N'-[6-(4-chlorophenyl)-7-(2,4-dichlorophenyl)-1-isobutyl-3-methyl-2-oxo-1,2-dihydro-1,8-naphthyridin-4-yl]-N,N-dimethylimidoformamide;

N'-[6-(4-chlorophenyl)-7-(2,4-dichlorophenyl)-3-ethyl-1-isobutyl-2-oxo-1,2-dihydro-1,8-naphthyridin-4-yl]-N,N-dimethylimidoformamide;

N'-[3-chloro-6-(4-chlorophenyl)-7-(2,4-dichlorophenyl)-1-isobutyl-2-oxo-1,2-dihydro-1,8-naphthyridin-4-yl]-N,N-dimethylimidoformamide;

N'-[6-(4-chlorophenyl)-7-(2,4-dichlorophenyl)-1-isobutyl-3-methoxy-2-oxo-1,2-dihydro-1,8-naphthyridin-4-yl]-N,N-dimethylimidoformamide;

N-[6-(4-chlorophenyl)-7-(2,4-dichlorophenyl)-3-(1-methoxyethyl)-1-methyl-2-oxo-1,2-dihydro-1,8-naphthyridin-4-yl]acetamide;

6-(4-chlorophenyl)-7-(2,4-dichlorophenyl)-3-isopropyl-1-methyl-4-(methylamino)-1,8-naphthyridin-2(1H)-one;

methyl 4-(acetylamino)-6-(4-chlorophenyl)-7-(2,4-dichlorophenyl)-1-methyl-2-oxo-1,2-dihydro-1,8-naphthyridine-3-carboxylate;

methyl 4-(N-acetylacetamido)-7-(2,4-dichlorophenyl)-6-(4-chlorophenyl)-1,2-dihydro-1-methyl-2-oxo-1,8-naphthyridine-3-carboxylate;

isopropyl 4-(acetylamino)-6-(4-chlorophenyl)-7-(2,4-dichlorophenyl)-1-methyl-2-oxo-1,2-dihydro-1,8-naphthyridine-3-carboxylate;

ethyl 4-amino-6-(4-chlorophenyl)-7-(2,4-dichlorophenyl)-1-methyl-2-oxo-1,2-dihydro-1,8-naphthyridine-3-carboxylate;

4-amino-6-(4-chlorophenyl)-7-(2,4-dichlorophenyl)-1-methyl-2-oxo-1,2-dihydro-1,8-naphthyridine-3-carboxamide;

4-(acetylamino)-6-(4-chlorophenyl)-7-(2,4-dichlorophenyl)-N,N,1-trimethyl-2-oxo-1,2-dihydro-1,8-naphthyridine-3-carboxamide;

4-amino-6-(4-chlorophenyl)-7-(2,4-dichlorophenyl)-1-methyl-2-oxo-1,2-dihydro-1,8-naphthyridine-3-carbonitrile;

N-[6-(4-chlorophenyl)-3-cyano-7-(2,4-dichlorophenyl)-1-methyl-2-oxo-1,2-dihydro-1,8-naphthyridin-4-yl]acetamide;

and pharmaceutically acceptable salts thereof.

8. A composition comprising a compound according to claim 1 and a pharmaceutically acceptable carrier.

\* \* \* \* \*